United States Patent
Ra et al.

(10) Patent No.: US 9,576,391 B2
(45) Date of Patent: Feb. 21, 2017

(54) TOMOGRAPHY APPARATUS AND METHOD OF RECONSTRUCTING A TOMOGRAPHY IMAGE BY THE TOMOGRAPHY APPARATUS

(71) Applicants: SAMSUNG ELECTRONICS CO., LTD., Suwon-si (KR); KOREA ADVANCED INSTITUTE OF SCIENCE AND TECHNOLOGY, Daejeon (KR)

(72) Inventors: Jong Beom Ra, Daejeon (KR); Seungeon Kim, Bucheon-si (KR); Kyoung-yong Lee, Hwaseong-si (KR); Toshihiro Rifu, Suwon-si (KR); Jong-hyon Yi, Yongin-si (KR); Iljun Ahn, Daejeon (KR); Yongjin Chang, Incheon (KR)

(73) Assignees: SAMSUNG ELECTRONICS CO., LTD., Suwon-si (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 14/629,078

(22) Filed: Feb. 23, 2015

(65) Prior Publication Data

US 2015/0243070 A1  Aug. 27, 2015

Related U.S. Application Data

(60) Provisional application No. 61/942,717, filed on Feb. 21, 2014.

(30) Foreign Application Priority Data

Oct. 13, 2014  (KR) .......................... 10-2014-0137849

(51) Int. Cl.
 *G06K 9/00* (2006.01)
 *G06T 15/08* (2011.01)
 (Continued)

(52) U.S. Cl.
 CPC .............. *G06T 15/08* (2013.01); *A61B 6/032* (2013.01); *A61B 6/4085* (2013.01); *A61B 6/463* (2013.01);
 (Continued)

(58) Field of Classification Search
 CPC ................................. A61B 6/504; G06T 15/08
 See application file for complete search history.

(56) References Cited

U.S. PATENT DOCUMENTS

| | | | |
|---|---|---|---|
| 6,621,889 B1 | 9/2003 | Mostafavi | |
| 6,934,357 B2 | 8/2005 | Boyd et al. | |

(Continued)

FOREIGN PATENT DOCUMENTS

JP  2009-233025 A  10/2009

OTHER PUBLICATIONS

Zheng et al (Evalulation of Interpolation method for surface-based motion compensated tomographic reconstruction for cardiac angiographic C-arm data, NIH, Med. Phys. 40 (3), Mar. 2013, 0094-2405/2013/40(3)/031107/12).*

(Continued)

*Primary Examiner* — Oneal R Mistry
(74) *Attorney, Agent, or Firm* — Sughrue Mion, PLLC

(57) ABSTRACT

A tomography apparatus includes a data acquirer which acquires a first image which corresponds to a first time point and a second image which corresponds to a second time point by performing a tomography scan on an object; an image reconstructor which acquires first information which relates to a relationship between a motion amount of the object and the time based on a motion amount between the (Continued)

first image and the second image, predicts a third image which corresponds to a third time point between the first and second time points based on the first information, corrects the first information by using the predicted third image and measured data which corresponds to the third time point, and reconstructs the third image by using the corrected first information; and a display which displays the reconstructed third image.

37 Claims, 30 Drawing Sheets

(51) Int. Cl.
*A61B 6/03* (2006.01)
*A61B 6/00* (2006.01)
*G06T 7/00* (2006.01)
*G06T 7/20* (2006.01)
*G06T 13/20* (2011.01)
*G06T 11/00* (2006.01)

(52) U.S. Cl.
CPC .............. *A61B 6/466* (2013.01); *A61B 6/469* (2013.01); *A61B 6/486* (2013.01); *A61B 6/503* (2013.01); *A61B 6/504* (2013.01); *A61B 6/5205* (2013.01); *A61B 6/5217* (2013.01); *A61B 6/5264* (2013.01); *A61B 6/5288* (2013.01); *A61B 6/541* (2013.01); *G06T 7/0022* (2013.01); *G06T 7/20* (2013.01); *G06T 11/005* (2013.01); *G06T 13/20* (2013.01); *A61B 6/4078* (2013.01); *A61B 6/563* (2013.01); *G06T 2207/10081* (2013.01); *G06T 2215/16* (2013.01)

(56) References Cited

U.S. PATENT DOCUMENTS

| 7,630,528 | B2* | 12/2009 | Kohler | G06T 11/006 378/4 |
|---|---|---|---|---|
| 8,478,013 | B2 | 7/2013 | Nakanishi et al. | |
| 2002/0025017 | A1 | 2/2002 | Stergiopoulos et al. | |
| 2007/0092055 | A1 | 4/2007 | Vives et al. | |
| 2009/0242776 | A1 | 10/2009 | Kobashi et al. | |
| 2011/0092793 | A1 | 4/2011 | Thomson et al. | |
| 2013/0303898 | A1* | 11/2013 | Kinahan | A61B 6/527 600/425 |
| 2013/0315459 | A1* | 11/2013 | Wollenweber | A61B 6/032 382/131 |
| 2014/0024916 | A1* | 1/2014 | Hautvast | A61B 5/7285 600/407 |
| 2014/0355855 | A1* | 12/2014 | Miao | A61B 5/721 382/131 |
| 2014/0357980 | A1* | 12/2014 | Hayes | A61B 5/0044 600/411 |
| 2015/0093001 | A1* | 4/2015 | Wang | G06T 7/0012 382/131 |
| 2016/0042537 | A1* | 2/2016 | Ng | G06T 11/005 382/131 |

OTHER PUBLICATIONS

Ota, Takamasa et al., "Clinical usefulness of automatic phase selection in coronary CT angiography (CTA)", Proc. of SPIE, vol. 6510, 65102N, 2007, 9 pages total.

Schafer, Dirk et al., "Motion-Compensated and Gated Cone Beam Filtered Back-Projection for 3-D Rotational Z-Ray Angiography", IEEE Transactions on Medical Imagining, vol. 25, No. 7, Jul. 2006, pp. 898-906.

Parker, Dennis L., "Optimal short scan convolution reconstruction for fan beam CT", Medical Physics 9, 254, Mar./Apr. 1982, pp. 254-257.

International Search Report dated May 26, 2015 issued by International Searching Authority in counterpart International Application No. PCT/KR2015/001689.

Written Opinion dated May 26, 2015 issued by International Searching Authority in counterpart International Application No. PCT/KR2015/001689.

* cited by examiner

Sinogram     CT Image

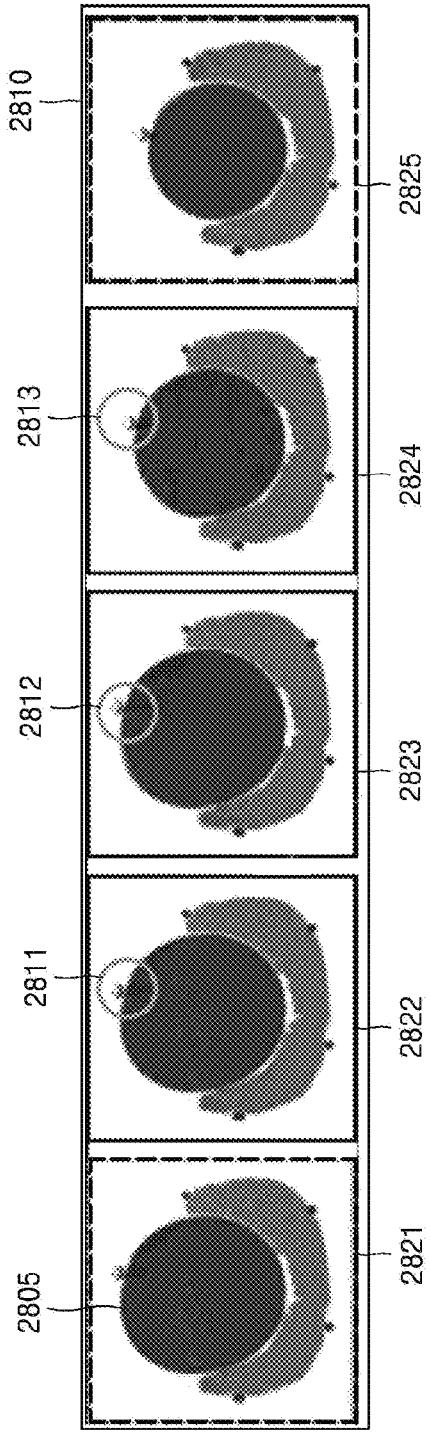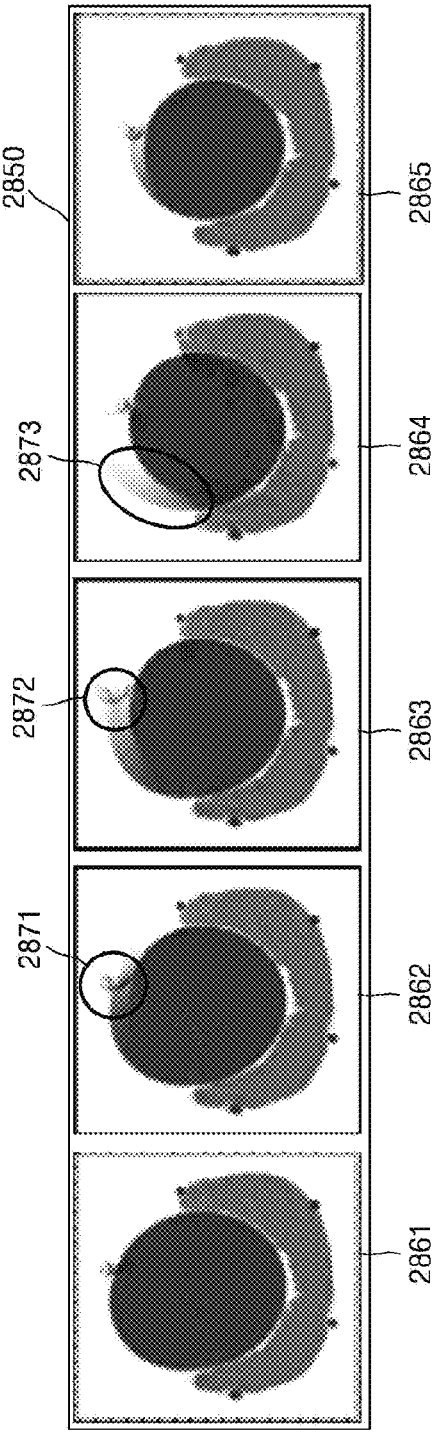

TOMOGRAPHY APPARATUS AND METHOD OF RECONSTRUCTING A TOMOGRAPHY IMAGE BY THE TOMOGRAPHY APPARATUS

CROSS-REFERENCE TO RELATED APPLICATION

This application claims the benefit of U.S. Provisional Patent Application No. 61/942,717, filed on Feb. 21, 2014, in the U.S. Patent and Trademark Office, and priority from Korean Patent Application No. 10-2014-0137849, filed on Oct. 13, 2014, in the Korean Intellectual Property Office, the disclosures of which are incorporated herein by reference in their entireties.

BACKGROUND

1. Field

One or more exemplary embodiments relate to a tomography apparatus and a method for reconstructing a tomography image by the tomography apparatus.

More specifically, one or more exemplary embodiments relate to a tomography apparatus that constructs a tomography image by performing a tomography scan on a moving object, and a method for reconstructing a tomography image which is performable by the tomography apparatus.

2. Description of the Related Art

Medical imaging apparatuses are equipment configured for acquiring an internal structure of an object as an image. Medical image processing apparatuses are noninvasive examination apparatuses that capture images of the structural details of a human body, internal tissue thereof, and fluid flow within a human body, process the images, and show the processed images. A user such as a doctor may diagnose a health state and a disease of a patient by using a medical image output from a medical image processing apparatus.

Representative examples of apparatuses for radiating X-rays onto a patient to scan an object include tomography apparatuses. Examples of the tomography apparatuses include a computed tomography (CT) apparatus.

Among medical image processing apparatuses, CT apparatuses are capable of providing a cross-sectional image of an object and distinctively expressing inner structures (e.g., organs such as a kidney, a lung, etc.) of the object, as compared with general X-ray apparatuses. Thus, CT apparatuses are widely used for accurately diagnosing a disease. Hereinafter, a medical image acquired by a tomography apparatus is referred to as a tomography image. In detail, a medical image acquired by a CT apparatus is referred to as a CT image.

To acquire a tomography image, a tomography scan is performed on an object using a tomography apparatus, and thus raw data is acquired. The tomography image is reconstructed using the acquired raw data. The raw data may be projection data acquired by projecting X-rays to the object, or a sinogram that is a collection of pieces of the projection data.

For example, in order to acquire a CT image, image reconstruction should be performed using a sinogram acquired by a CT scan. Reconstruction of a CT image will now be described in detail with reference to FIG. 1.

FIGS. 1A and 1B are a schematic diagram and images which illustrate a CT scan and reconstruction of a CT image, respectively.

In detail, FIG. 1A is a schematic diagram which illustrates a CT scan that is performed by a CT apparatus that performs a CT scan while rotating around an object 25 and acquires raw data which corresponds to the CT scan. FIG. 1B illustrates a sinogram acquired by a CT scan and a reconstructed CT image.

The CT apparatus generates X-rays, radiates the X-rays toward the object 25, and detects X-rays that have passed through the object 25 by using an X-ray detector (not shown). The X-ray detector produces raw data which corresponds to the detected X-rays.

In detail, referring to FIG. 1A, an X-ray generator 20 included in the CT apparatus radiates X-rays toward the object 25. When the CT apparatus performs a CT scan, the X-ray generator 20 rotates around the object 25 and acquires a plurality of pieces of raw data, for example, first raw data 30, second raw data 31, and third raw data 32, corresponding to angles to which the X-ray generator 20 rotates, respectively. In detail, the X-ray detector (not shown) detects X-rays applied to the object 25 at a position P1 to thereby acquire the first raw data 30, and detects X-rays applied to the object 25 at a position P2 to thereby acquire the second raw data 31. The X-ray detector (not shown) detects X-rays applied to the object 25 at a position P3 to thereby acquire the third raw data 32. The raw data may include projection data.

In order to generate one cross-sectional CT image, the X-ray generator 20 should perform a CT scan while rotating at least 180° with respect to the object.

Referring to FIG. 1B, a single sinogram 40 may be acquired by combining the first, second, and third raw data 30, 31, and 32 acquired while the X-ray generator 20 is moving at intervals of a predetermined angle as described above with reference to FIG. 1A. The sinogram 40 is acquired via a CT scan performed while the X-ray generator 20 rotates during one cycle. The sinogram 40 corresponding to one cyclic rotation may be used for generation of one cross-sectional CT image. One cyclic rotation may be about more than a half turn or one full turn, according to the specifications of a CT system.

A CT image 50 is reconstructed by performing back-projection with respect to the sinogram 40.

In general, it takes about 0.2 seconds for the X-ray generator 20 to rotate a half turn.

When an object that is a target of a CT scan moves at a relatively fast speed, motion of the object occurs during one cycle. Due to the motion of the object, motion artifacts may occur in the reconstruction of a CT image.

A three-dimensional (3D) CT image may be reconstructed from a plurality of cross-sectional CT images. Thus, while raw data necessary for reconstructing a 3D CT image is being acquired, motion of an object occurs more frequently.

When motion artifacts are present in the reconstructed CT image, an edge of an object may be blurred, or an image may be unclear. The motion artifacts in a CT image degrade the quality of the CT image, and thus when a user, for example, a medical doctor, reads the CT image and diagnoses a disease, the user is unable to accurately read the CT image and diagnose the disease.

Thus, when a CT scan is performed on a moving object, it is important to reconstruct a CT image in which image blurring caused by motion artifacts is reduced.

SUMMARY

One or more exemplary embodiments include a tomography apparatus which is capable of reducing an occurrence of motion artifacts within a reconstructed tomography image, and a tomography image reconstructing method performed by the tomography apparatus.

Additional aspects will be set forth in part in the description which follows and, in part, will be apparent from the description, or may be learned by practice of the presented exemplary embodiments.

According to one or more exemplary embodiments, a tomography apparatus includes a data acquirer configured to acquire a first image which corresponds to a first time point and to acquire a second image which corresponds to a second time point by performing a tomography scan on an object; an image reconstructor configured to acquire first information which relates to a relationship between a time amount and a motion amount of the object based on the acquired first image and the acquired second image, to predict a third image which corresponds to a third time point between the first and second time points based on the first information, to correct the first information by using the predicted third image and measured data which corresponds to the third time point, and to reconstruct a final third image which corresponds to the third time point by using the corrected first information; and a display configured to display the reconstructed final third image.

The first information may include information which indicates a relationship between a time amount and a motion amount of the object which correspond to a motion vector field (MVF) between the first image and the second image.

The image reconstructor may be further configured to correct the first information based on predicted data acquired by forward projecting the predicted third image with respect to the measured data.

The image reconstructor may be further configured to compare the predicted data with the measured data and to correct the first information such that a difference between the predicted data and the measured data decreases.

The image reconstructor may be further configured to compare a predicted sinogram acquired by forward projecting the predicted third image with a measured sinogram acquired by detecting X-rays that have been projected by the object within a time section which corresponds to the third time point, and to correct the first information such that a difference between the predicted sinogram and the measured sinogram decreases.

The image reconstructor may be further configured to compare a fourth image obtained by back-projecting measured data acquired at the third time point with the predicted third image and to correct the first information such that a difference between the predicted third image and the fourth image decreases.

The image reconstructor may be further configured to correct the first information at the third time point which is a time point apart from the first time point toward the second time point by a first time period.

The image reconstructor may be further configured to correct the first information at the third time point which is a time point apart from the second time point toward the first time point by a first time period.

The image reconstructor may be further configured to acquire second information by correcting the first information at a time point apart from the first time point toward the second time point by a first time period, to acquire third information by correcting the first information at a time point apart from the second time point toward the first time point by the first time period, and to generate corrected first information, based on the second information and the third information.

The image reconstructor may be further configured to warp a center of a voxel which indicates the object based on the corrected first information and to reconstruct the final third image by back-projecting a position of the warped center of the voxel.

The data acquirer may be further configured to select two time points at which a motion of the object is minimized within a predetermined time section as the first time point and the second time point.

The data acquirer may be further configured to reconstruct an image at intervals of a second time period within the predetermined time section, to measure a difference between an image reconstructed at a fourth time point and an image reconstructed at fifth time point which is adjacent to the fourth time point, and to select two time points at which a motion of the object is minimized, as the first time point and the second time point based on the measured difference.

The data acquirer may be further configured to acquire projection data at intervals of a second time period within the predetermined time section, to measure a difference between projection data reconstructed at a fourth time point and projection data reconstructed at a fifth time point which is adjacent to the fourth time point, and to select two time points at which a motion of the object is minimized as the first time point and the second time point based on the measured difference.

The display may be configured to display a user interface (UI) screen image which relates to selecting the first time point and the second time point.

The display may be configured to display a UI screen image which relates to selecting the third time point between the first time point and the second time point.

The image reconstructor may be further configured to reconstruct a plurality of images which respectively correspond to a plurality of time points between the first time point and the second time point by using the corrected first information.

The display may be configured to display a screen image which includes the plurality of images.

The image reconstructor may be further configured to generate a moving picture by using the plurality of images.

The display may be configured to display a UI image which relates to playing back the moving picture.

The image reconstructor may be further configured to perform motion correction with respect to the first image and the second image by using the corrected first information and to re-acquire the first information by using the motion-corrected first image and the motion-corrected second image.

According to one or more exemplary embodiments, a method for reconstructing a tomography image includes acquiring a first image which corresponds to a first time point and a second image which corresponds to a second time point by performing a tomography scan on an object; acquiring first information which relates to a relationship between a motion amount of the object and a time amount based on the acquired first image and the acquired second image, predicting a third image which corresponds to a third time point between the first time point and the second time point based on the first information, and correcting the first information by using the predicted third image and measured data which corresponds to the third time point; and reconstructing a final third image which corresponds to the third time point by using the corrected first information.

BRIEF DESCRIPTION OF THE DRAWINGS

These and/or other aspects will become apparent and more readily appreciated from the following description of exemplary embodiments, taken in conjunction with the accompanying drawings in which:

FIGS. 28A and 28B are views which illustrate motion artifacts existing in a reconstructed tomography image;

DETAILED DESCRIPTION

Figure 1A:
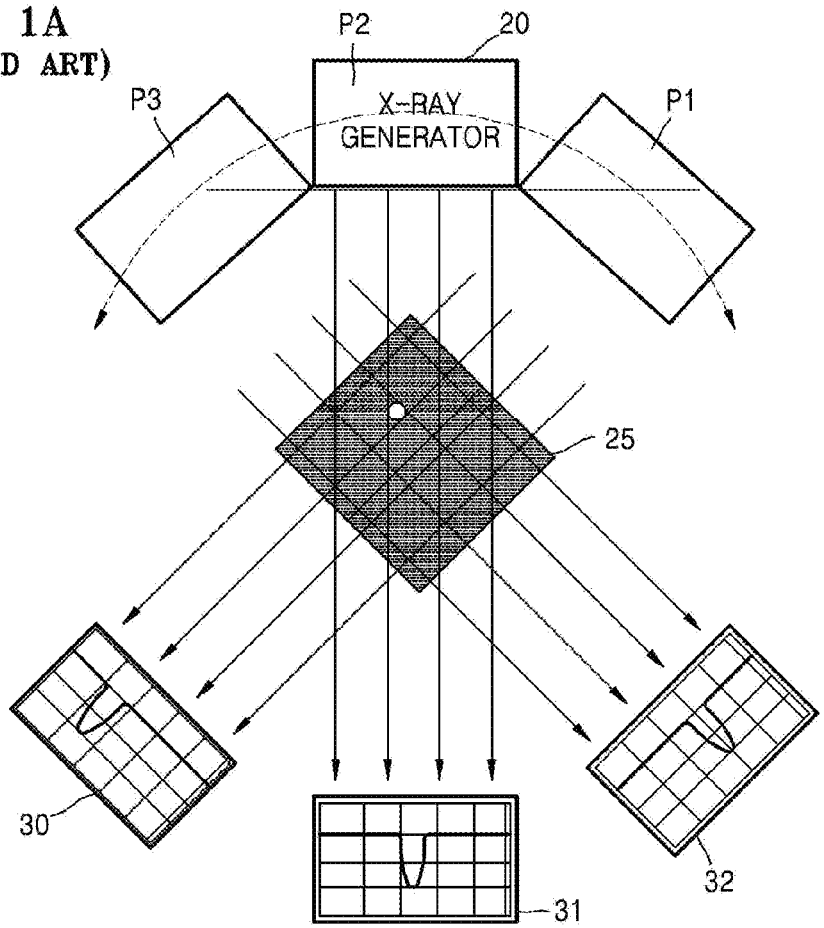
FIGS. 1A and 1B are a schematic diagram and images which illustrate a computed tomography (CT) scan and reconstruction of a CT image, respectively.
Figure 1B:
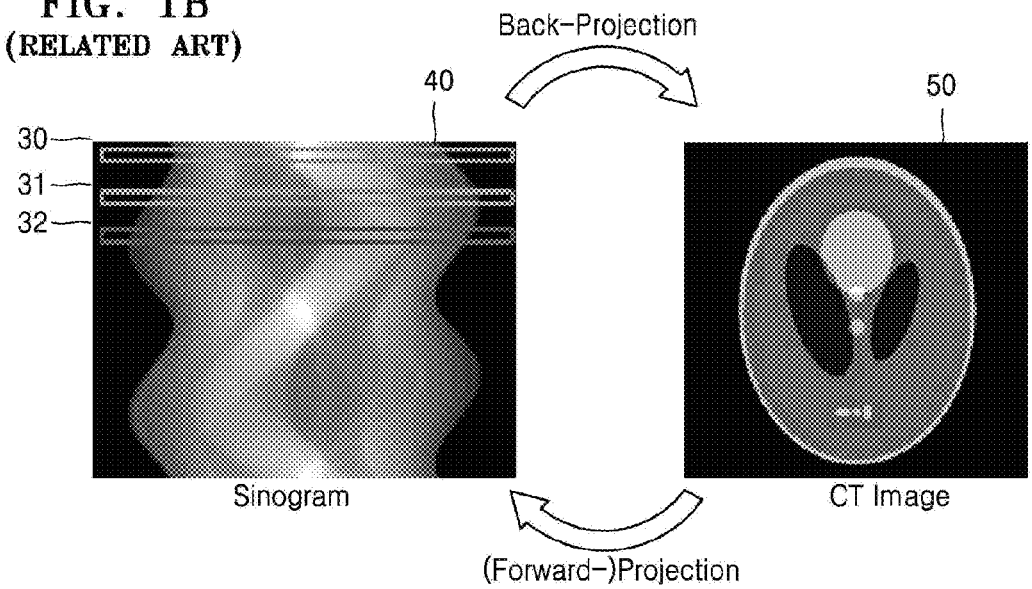

Advantages and features of one or more exemplary embodiments and methods for accomplishing the same may be understood more readily by reference to the following detailed description of the exemplary embodiments and the accompanying drawings. In this regard, the present exemplary embodiments may have different forms and should not be construed as being limited to the descriptions set forth herein. Rather, these exemplary embodiments are provided so that this disclosure will be thorough and complete and will fully convey the concept of the present exemplary embodiments to one of ordinary skill in the art, and the present inventive concept will only be defined by the appended claims. Like reference numerals refer to like elements throughout the specification.

Hereinafter, the terms used in the specification will be briefly defined, and the exemplary embodiments will be described in detail.

All terms including descriptive or technical terms which are used herein should be construed as having meanings that are well-known to one of ordinary skill in the art. However, the terms may have different meanings according to the intention of one of ordinary skill in the art, precedent cases, or the appearance of new technologies. Also, some terms may be arbitrarily selected by the applicant, and in this case, the meaning of the selected terms will be described in detail in the detailed description. Thus, the terms used herein have to be defined based on the meaning of the terms together with the description throughout the specification.

When a part "includes" or "comprises" an element, unless there is a particular description contrary thereto, the part can further include other elements, not excluding the other elements. Also, the term "unit" in the exemplary embodiments refers to a software component or a hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, and/or variables. A function provided by the components and "units" may be associated with the smaller number of components and "units", or may be divided into additional components and "units".

Reference will now be made in detail to exemplary embodiments, examples of which are illustrated in the accompanying drawings, wherein like reference numerals refer to the like elements throughout. In this regard, the present exemplary embodiments may have different forms and should not be construed as being limited to the descriptions set forth herein. In the following description, well-known functions or constructions are not described in detail so as not to obscure the exemplary embodiments with unnecessary detail.

Throughout the specification, an "image" may refer to multi-dimensional data formed of discrete image elements, e.g., pixels in a two-dimensional (2D) image and voxels in a three-dimensional (3D) image. For example, the image may include a medical image of an object which is captured by a computed tomography (CT) imaging apparatus.

A tomography apparatus is a typical apparatus among apparatuses configured for capturing an image of an object by projecting X-rays toward a patient. In detail, a tomography system may include all tomography apparatuses, such as a computed tomography (CT) apparatus, an optical coherence tomography (OCT), or a positron emission tomography (PET)-CT apparatus. In the following description, a CT system is exemplified as the tomography system.

Throughout the specification, a "CT image" may refer to an image generated by synthesizing a plurality of X-ray images that are obtained by photographing an object while a CT imaging apparatus rotates around at least one axis with respect to the object.

Furthermore, in the present specification, an "object" may be a human, an animal, or a part of a human or animal. For example, the object may include an organ (e.g., the liver, the heart, the womb, the brain, a breast, or the abdomen), a blood vessel, and/or a combination thereof. Furthermore, the "object" may be a phantom. The phantom means a material having a density, an effective atomic number, and a volume that are approximately the same as those of an organism. For example, the phantom may be a spherical phantom having properties similar to the physical body.

Throughout the specification, a "user" may be, but is not limited to, a medical expert including a medical doctor, a nurse, a medical laboratory technologist, a medial image expert, or a technician who repairs a medical apparatus.

Since a CT system is capable of providing a cross-sectional image of an object, the CT system may distinctively express an inner structure, e.g., an organ such as a kidney or a lung, of the object, as compared with a general X-ray imaging apparatus.

The CT system may obtain a plurality of pieces of image data with a thickness of not more than 2 mm several tens to several hundred times per second, and then may process the plurality of pieces of image data, so that the CT system may provide a relatively accurate cross-sectional image of the object. According to the related art, only a horizontal cross-sectional image of the object can be obtained, but this issue has been overcome due to various image reconstruction methods. Examples of 3D image reconstruction methods are as below:

Shade surface display (SSD)—an initial 3D imaging method for displaying only voxels having a predetermined Hounsfield Units (HU) value.

Maximum intensity projection (MIP)/minimum intensity projection (MinIP)—a 3D imaging method for displaying only voxels having the greatest or smallest HU value from among voxels that construct an image.

Volume rendering (VR)—an imaging method capable of adjusting a color and transmittance of voxels that constitute an image, according to areas of interest.

Virtual endoscopy—a method that enables endoscopy observation in a 3D image that is reconstructed by using the VR method or the SSD method.

Multi-planar reformation (MPR)—a method for reconstructing an image into a different cross-sectional image. A user may reconstruct an image in any desired direction.

Editing—a method for editing adjacent voxels so as to enable a user to easily observe an area of interest in volume rendering.

Voxel of interest (VOI)—a method for displaying only a selected area in volume rendering.

This proposed exemplary embodiment will now be described with reference to FIG. 2. The CT system 100 may include any of various types of devices.

Figure 2:
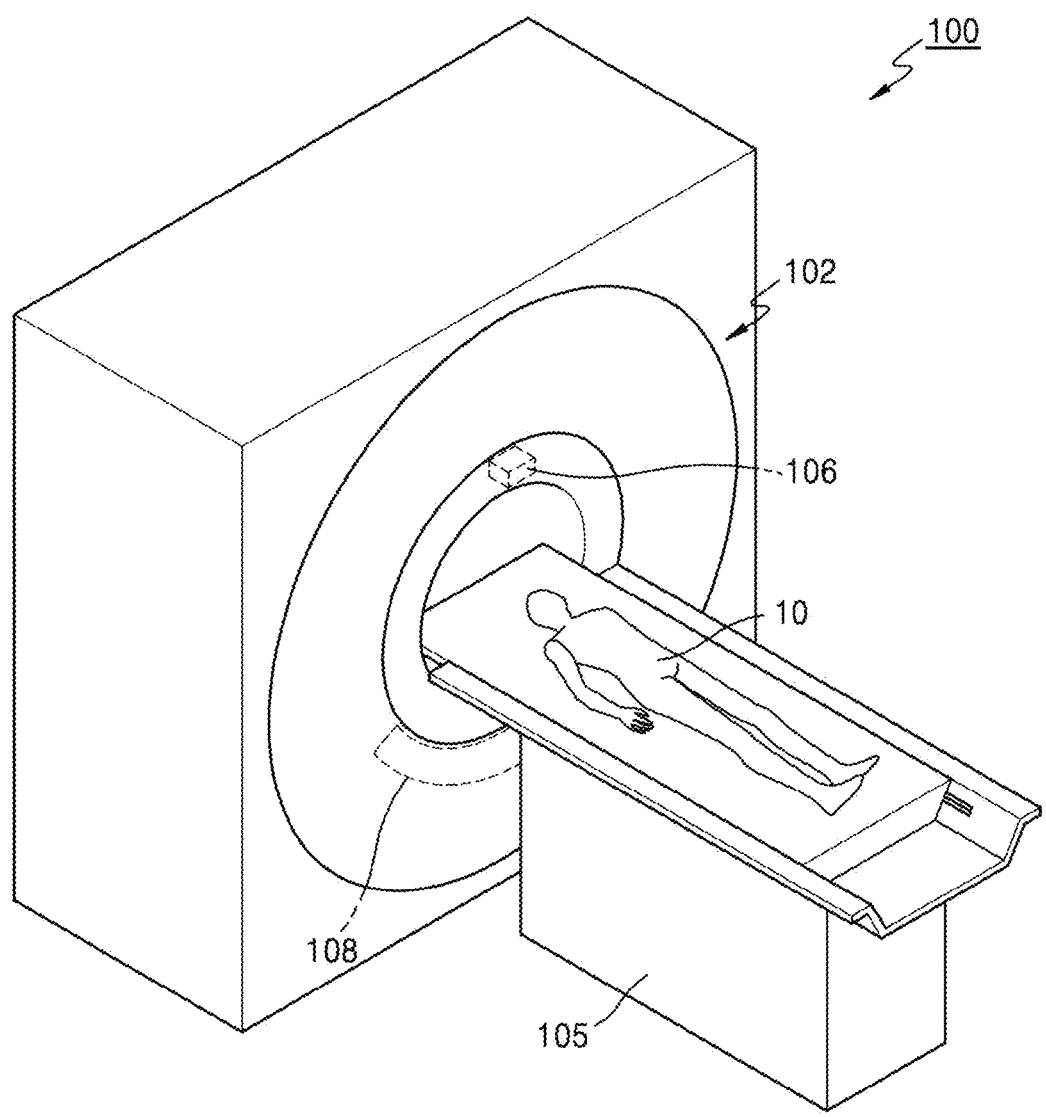
FIG. 2 is a schematic diagram of a tomography system.

FIG. 2 schematically illustrates the CT system 100. Referring to FIG. 2, the CT system 100 may include a gantry 102, a table 105, an X-ray generator 106, and an X-ray detecting unit (also referred to herein as an "X-ray detector") 108.

The gantry 102 may include the X-ray generator 106 and the X-ray detecting unit 108.

An object 10 may be positioned on the table 105.

The table 105 may move in a predetermined direction (e.g., at least one of up, down, right, and left directions) during a CT imaging procedure. In addition, the table 105 may tilt and/or rotate by a predetermined angle in a predetermined direction.

The gantry 102 may also tilt by a predetermined angle in a predetermined direction.

Figure 3:
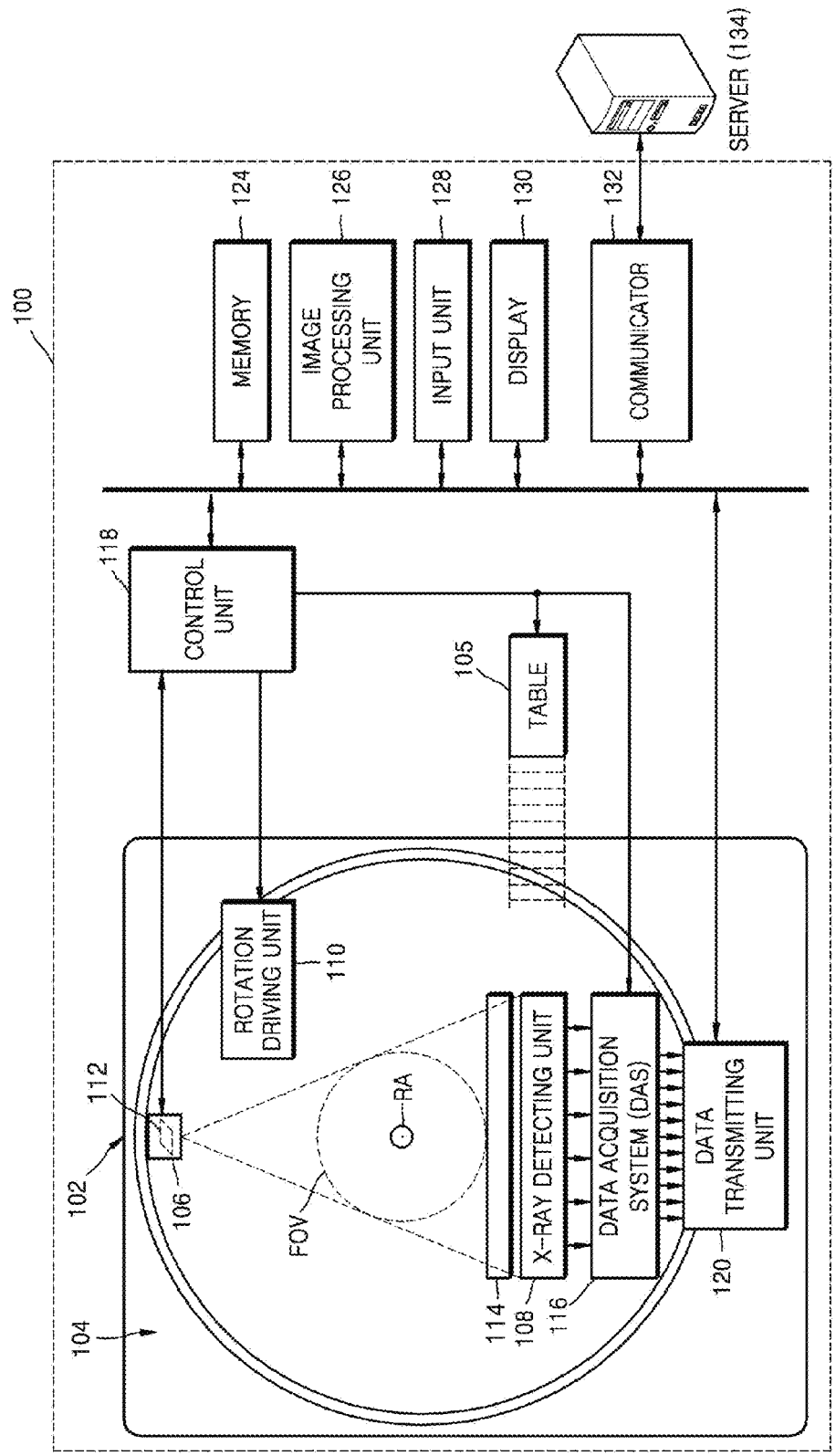
FIG. 3 illustrates a structure of the tomography system of FIG. 2.

FIG. 3 is a block diagram illustrating a structure of the CT system 100.

The CT system 100 may include the gantry 102, the table 105, a control unit (also referred to herein as a "controller") 118, a storage unit (also referred to herein as a "storage" and/or as a "memory") 124, an image processing unit (also referred to herein as an "image processor") 126, an input unit (also referred to herein as an "input device") 128, a display unit (also referred to herein as a "display device" and/or as a "display") 130, and a communication unit (also referred to herein as a "communicator") 132.

As described above, the object 10 may be positioned on the table 105. In the present exemplary embodiment, the table 105 may move in a predetermined direction (e.g., at least one of up, down, right, and left directions), and a movement of the table 105 may be controlled by the control unit 118.

The gantry 102 may include a rotating frame 104, the X-ray generator 106, the X-ray detecting unit 108, a rotation driving unit (also referred to herein as a "rotation driver") 110, a data acquisition system (DAS) 116, and a data transmitting unit (also referred to herein as a "data transmitter") 120.

The gantry 102 may include the rotating frame 104, which has a loop shape, and which is capable of rotating with respect to a predetermined rotation axis RA. Alternatively, the rotating frame 104 may have a disc shape.

The rotating frame 104 may include the X-ray generator 106 and the X-ray detecting unit 108 that are arranged to face each other so as to have predetermined fields of view (FOV). The rotating frame 104 may also include an anti-scatter grid 114. The anti-scatter grid 114 may be positioned between the X-ray generator 106 and the X-ray detecting unit 108.

Although FIG. 3 illustrates that the rotating frame 104 includes one X-ray generator 106, the rotating frame 104 may include a plurality of X-ray generators. When the rotating frame 104 includes a plurality of X-ray generators, the rotating frame 104 includes a plurality of X-ray detectors which respectively correspond to the plurality of X-ray generators. In detail, one X-ray generator 106 is one X-ray source. For example, when the rotating frame 104 includes two X-ray generators 106, it may be stated that the rotating frame 104 includes a dual source. In the following description, when the rotating frame 104 includes one X-ray generator 106, the one X-ray generator 106 included in the rotating frame 104 is referred to as a single source. When the rotating frame 104 includes two X-ray generators (not shown), the two X-ray generators included in the rotating frame 104 is referred to as a dual source. In the circumstance in which two X-ray generators form a dual source, one X-ray generator is referred to as a first source and the other X-ray generator is referred to as a second source. The CT system 100 in which one X-ray generator 106 is included in the rotating frame 104 is referred to as a single source tomography apparatus, and the CT system 100 in which two X-ray generators are included in the rotating frame 104 is referred to as a dual source tomography apparatus. In a medical imaging system, X-ray radiation that reaches a detector (or a photosensitive film) includes not only attenuated primary radiation that forms a valuable image, but also scattered radiation that deteriorates the quality of an image. In order to transmit most of the primary radiation and to attenuate the scattered radiation, the anti-scatter grid 114 may be positioned between a patient and the detector (or the photosensitive film).

For example, the anti-scatter grid 114 may be formed by alternately stacking lead foil strips and an interspace material, such as any of a solid polymer material, solid polymer, and/or a fiber composite material. However, formation of the anti-scatter grid 114 is not limited thereto.

The rotating frame 104 may receive a driving signal from the rotation driving unit 110 and may rotate the X-ray generator 106 and the X-ray detecting unit 108 at a predetermined rotation speed. The rotating frame 104 may receive the driving signal and power from the rotation driving unit 110 while the rotating frame 104 contacts the rotation driving unit 110 via a slip ring (not shown). Further, the rotating frame 104 may receive the driving signal and power from the rotation driving unit 110 via wireless communication.

The X-ray generator 106 may receive a voltage and a current from a power distribution unit (PDU) (not shown) via a slip ring (not shown) and then a high voltage generating unit (also referred to herein as a "high voltage generator") (not shown), and may generate and emit an X-ray. When the high voltage generating unit applies a predetermined voltage (hereinafter, referred to as a tube voltage) to the X-ray generator 106, the X-ray generator 106 may generate X-rays having a plurality of energy spectra that correspond to the tube voltage.

The X-ray generated by the X-ray generator 106 may be emitted in a predetermined form due to a collimator 112.

The X-ray detecting unit 108 may be positioned to face the X-ray generator 106. The X-ray detecting unit 108 may be positioned to face the X-ray generator 106. Each of the plurality of X-ray detecting devices may establish one channel, but one or more exemplary embodiments are not limited thereto.

The X-ray detecting unit 108 may detect the X-ray that is generated by the X-ray generator 106 and that propagates through the object 10, and may generate an electrical signal which corresponds to an intensity of the detected X-ray.

The X-ray detecting unit 108 may include an indirect-type X-ray detector which is configured for detecting radiation after converting the radiation into light, and a direct-type X-ray detector which is configured for detecting radiation after directly converting the radiation into electric charges. The indirect-type X-ray detector may use a scintillator. Further, the direct-type X-ray detector may use a photon counting detector. The DAS 116 may be connected to the X-ray detecting unit 108. Electrical signals generated by the X-ray detecting unit 108 may be collected by wire or wirelessly by the DAS 116. Electrical signals generated by the X-ray detecting unit 108 may be collected by wire or wirelessly by the DAS 116. In addition, the electrical signals generated by the X-ray detecting unit 108 may be provided to an analog-to-digital converter (not shown) via an amplifier (not shown).

According to a slice thickness or the number of slices, only some of a plurality of pieces of data collected by the X-ray detecting unit 108 may be provided to the image processing unit 126 via the data transmitting unit 120, or the image processing unit 126 may select only some of the plurality of pieces of data.

Such a digital signal may be provided to the image processing unit 126 via the data transmitting unit 120. The digital signal may be provided to the image processing unit 126 by wire or wirelessly.

The control unit 118 may control an operation of each of the elements in the CT system 100. For example, the control unit 118 may control operations of the table 105, the rotation driving unit 110, the collimator 112, the DAS 116, the storage unit 124, the image processing unit 126, the input unit 128, the display unit 130, the communication unit 132, and/or the like.

The image processing unit 126 may receive data acquired by the DAS 116 (e.g., pure data that is data before processing), via the data transmitting unit 120, and may perform pre-processing upon the received data.

The pre-processing may include, for example, any of a process of correcting a sensitivity irregularity between channels and a process of correcting signal loss due to a rapid decrease in signal strength or due to the presence of an X-ray absorbing material such as a metal.

Data output from the image processing unit 126 may be referred to as raw data and/or as projection data. The projection data may be stored in the storage unit 124 in conjunction with information relating to imaging conditions (e.g., the tube voltage, an imaging angle, etc.) which exist during the acquisition of data.

The projection data may be a group of data values that correspond to the intensity of the X-ray that has propagated through the object 10. For convenience of description, a group of a plurality of pieces of projection data that are simultaneously obtained from all channels at the same imaging angle is referred to as a projection data set.

The storage unit 124 may include at least one storage medium from among a flash memory-type storage medium, a hard disk-type storage medium, a multimedia card microtype storage medium, card-type memories (e.g., an SD card, an XD memory, and the like), random access memory (RAM), static random access memory (SRAM), read-only memory (ROM), electrically erasable programmable ROM (EEPROM), programmable ROM (PROM), magnetic memory, a magnetic disc, and an optical disc.

The image processing unit 126 may reconstruct a cross-sectional image of the object 10 by using the acquired projection data set. The cross-sectional image may be a 3D image. In particular, the image processing unit 126 may reconstruct a 3D image of the object 10 by using a cone beam reconstruction method or the like, based on the acquired projection data set.

The input unit 128 may receive an external input with respect to any of an X-ray tomography imaging condition, an image processing condition, and/or the like. For example, the X-ray tomography imaging condition may include any of tube voltages, an energy value setting with respect to a plurality of X-rays, a selection of an imaging protocol, a selection of an image reconstruction method, a setting of a FOV area, the number of slices, a slice thickness, a parameter setting with respect to image post-processing, and/or the like. Further, the image processing condition may include any of a resolution of an image, an attenuation coefficient setting for the image, setting for an image combining ratio, and/or the like.

The input unit 128 may include a device which is configured for receiving a predetermined input from an external source. For example, the input unit 128 may include any of a microphone, a keyboard, a mouse, a joystick, a touch pad, a touch pen, a voice recognition device, a gesture recognition device, and/or the like.

The display unit 130 may display an X-ray image reconstructed by the image processing unit 126.

Exchanges of data, power, or the like between the aforementioned elements may be performed by using at least one of wired communication, wireless communication, and optical communication.

The communication unit 132 may perform communication with any of an external device, an external medical apparatus, etc. via a server 134, and/or the like. The communication will now be described with reference to FIG. 4.

Figure 4:
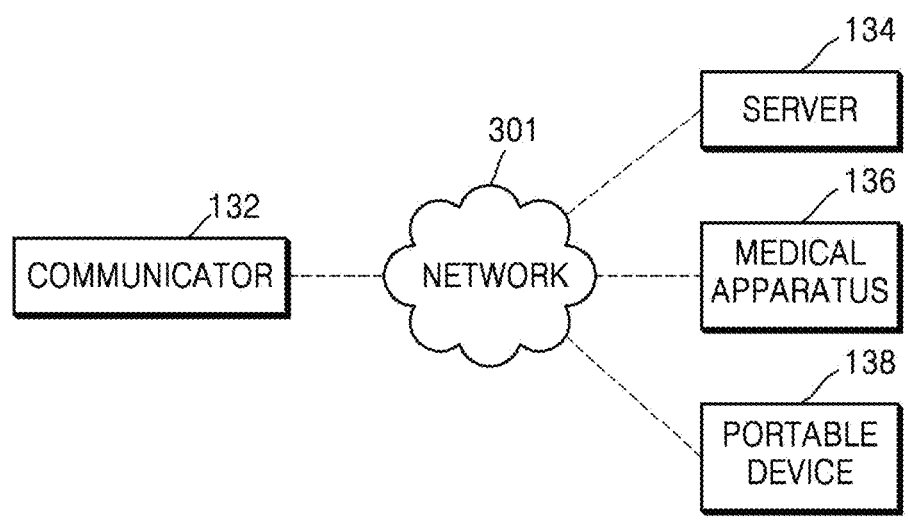
FIG. 4 is a block diagram illustrating the communication performed by a communication unit included in the tomography system of FIG. 2.

FIG. 4 is a block diagram illustrating the communication performed by the communication unit 132.

The communication unit 132 may be wiredly or wirelessly connected to a network 301 and thus may perform communication with an external device, such as any of the server 134, a medical apparatus 136, and/or a portable device 138. The communication unit 132 may exchange data with a hospital server and/or with other medical apparatuses in a hospital connected via a picture archiving and communication system (PACS).

The communication unit 132 may perform data communication with the external device and/or the like, according to a Digital Imaging and Communications in Medicine (DICOM) standard.

The communication unit 132 may transmit and receive data related to diagnosing the object 10, via the network 301. The communication unit 132 may transmit and/or receive a medical image obtained from the medical apparatus 136 such as any of a magnetic resonance imaging (MRI) apparatus, an X-ray apparatus, and/or the like.

Furthermore, the communication unit 132 may receive a diagnosis history and/or a medical treatment schedule about a patient from the server 134, and may use the diagnosis history and/or the medical treatment schedule to diagnose the patient. Further, the communication unit 132 may perform data communication not only with the server 134 or the medical apparatus 136 in a hospital, but also with the portable device 138 of a user or patient.

In addition, the communication unit 132 may transmit information about a device error, information about a quality control status, or the like to a system manager or a service manager via the network 301, and may receive a feedback regarding the information from the system manager or service manager.

Figure 5:
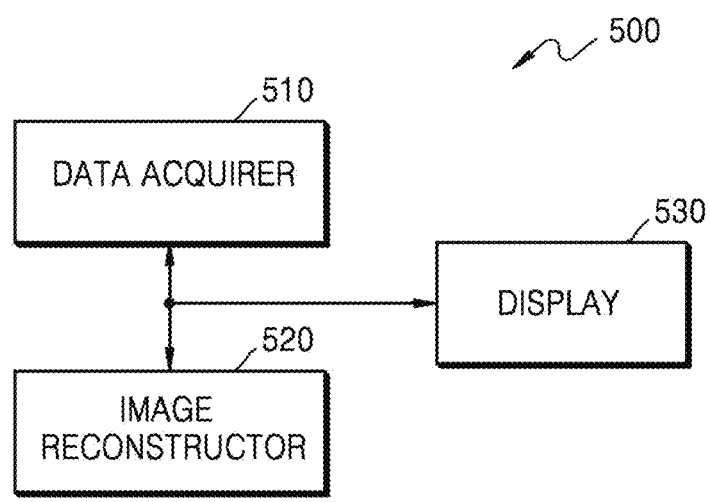
FIG. 5 is a block diagram of a tomography apparatus, according to an exemplary embodiment.

FIG. 5 is a block diagram of a tomography apparatus 500, according to an exemplary embodiment.

Referring to FIG. 5, the tomography apparatus 500 includes a data acquirer 510 and an image reconstructor 520. The tomography apparatus 500 may further include a display 530.

The tomography apparatus 500 may be included in the tomography system described above with reference to FIGS. 3 and 4. Alternatively, the tomography apparatus 500 may be included in the medical apparatus 136 or the portable device 138 of FIG. 4 and may be connected to the CT system 100 in order to operate. In detail, the tomography apparatus 500 may include any or all medical imaging apparatuses that reconstruct images by using the data acquired by using a light beam that has propagated through an object. In particular, the tomography apparatus 500 may be all medical imaging apparatuses that reconstruct images by using projection data obtained by using a light beam that has passed through an object. In detail, the tomography apparatus 500 may include any of a computed Tomography (CT) apparatus, an optical coherence tomography (OCT) apparatus, and/or a positron emission tomography (PET)-CT apparatus. Accordingly, a tomography image obtained by the tomography apparatus 500 according to the present exemplary embodiment may include any of a CT image, an OCT image, and/or a PET image. In the drawings referred to the following descriptions, a CT image is exemplified as the tomography image. When the tomography apparatus 500 is included in the CT system 100 of FIG. 2 or FIG. 3, the data acquirer 510 and the image reconstructor 520 of FIG. 5 may be included in the image processing unit 126 or the control unit 118 of FIG. 3. The display 530 may correspond to the display 130 of FIG. 3. Accordingly, descriptions of the CT apparatus 500 that are the same as those made with reference to FIGS. 2 and 3 are not repeated herein.

The data acquirer 510 acquires a first image which corresponds to a first time point and a second image which corresponds to a second time point by performing a tomography scan on an object. In detail, the data acquirer 510 may receive raw data and reconstruct the first image corresponding to the first time point and the second image corresponding to the second time point by using the raw data. The first image and the second image may be two-dimensional (2D) tomography images or 3D tomography images.

The object may include a predetermined organ. In detail, the object may include at least one selected from among the heart, the abdomen, the womb, the brain, breasts, and the liver. For example, the object may include a heart that is expressed by a surface thereof. A heart may include at least one of tissues having different brightness values in a predetermined area.

In detail, the data acquirer 510 may include the X-ray generator 106 of FIG. 3. The X-ray generator 106 may acquire raw data by performing a tomography scan while rotating around the object. The data acquirer 510 may receive the raw data from the X-ray generator 106.

The raw data may include projection data acquired by projecting radiation to the object, or a sinogram that is a collection of pieces of the projection data. The raw data may also include an image that is generated by performing filtered back-projection on the projection data or the sinogram. In detail, when the X-ray generator 106 at a predetermined position projects X-rays toward the object, a viewpoint or a direction in which the X-ray generator 106 faces the object is referred to as a view. The projection data is raw data acquired in correspondence with a view, and the sinogram denotes raw data acquired by sequentially listing a plurality of pieces of projection data.

In detail, when the X-ray generator 106 emits a cone beam while rotating around the object that is moving, the data acquirer 510 may acquire raw data which corresponds to the cone beam, and may convert the acquired raw data to raw data which corresponds to a parallel beam by rearranging the acquired raw data. First information may be acquired by using the raw data which corresponds to the parallel beam. In so doing, the cone beam is converted into the parallel beam, which is referred to as rebinning, and the first information may be acquired by using the raw data which corresponds to the parallel beam. The rebinning of the cone beam is described below in detail with reference to FIGS. 9A and 9B.

The image reconstructor 520 acquires first information which indicates a relationship between a motion amount of the object and the corresponding time amount, based on a motion amount between the first image and the second image. In detail, the first information indicates a motion amount of the object according to the lapse of time, and the first information may include information which indicates a motion of a surface forming the object at a predetermined time point. The image reconstructor 520 predicts a third image which corresponds to a third time point between the first and second time points based on the first information, and corrects the first information by using the predicted third image and measured data which corresponds to the third time point. The measured data acquired at the third time point denotes raw data acquired in a time section which corresponds to the third time point or an image reconstructed by using the raw data acquired in the time section which corresponds to the third time point, when the raw data is generated using X-rays that have passed through the object and have been detected. In particular, the measured data acquired at the third time point denotes raw data actually acquired in order to create an image of the object at the third time point or an image reconstructed using the actually acquired raw data. Data predicted using the first information denotes raw data or an image that corresponds to a state of an object at a predetermined time point that has been predicted based on a motion amount of the object that is indicated by the first information. The data predicted using the first information will be hereinafter referred to as predicted data.

A tomography image reconstructed by the image reconstructor 520 may be a 2D tomography image or a 3D tomography image. A case where projection data is used as the raw data will now be illustrated. Raw data necessary for reconstructing the first image corresponding to the first time point is referred to as first projection data, and raw data necessary for reconstructing the second image corresponding to the second time point is referred to as second projection data. Raw data necessary for reconstructing the third image corresponding to the third time point is referred to as third projection data.

A result of correcting the first information by using the predicted third image is hereinafter referred to as corrected first information. The image reconstructor 520 reconstructs the third image by using the corrected first information. A third image that is reconstructed using the corrected first information and corresponds to the third time point is hereinafter referred to as a final third image.

The motion amount may be a difference between at least one selected from among the shape, size, and position of a predetermined object included in the first image and that of a predetermined object included in the second image, which is generated due to the motion of the object.

The display 530 displays the third image. Since the display 530 corresponds to the display 130 of FIG. 3, a repeated description thereof will be omitted.

A detailed operation of the tomography apparatus 500 will now be described in detail with reference to FIGS. 6-20.

Figure 6:
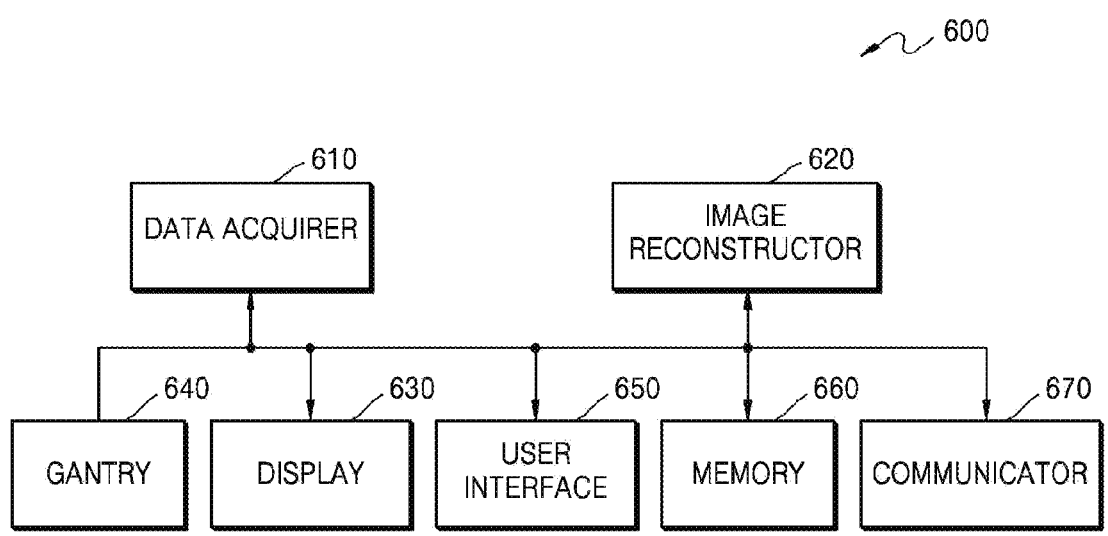
FIG. 6 is a block diagram of a tomography apparatus, according to another exemplary embodiment.

FIG. 6 is a block diagram of a tomography apparatus 600, according to another exemplary embodiment.

Since a data acquirer 610 and an image reconstructor 620 of FIG. 6 identically correspond to the data acquirer 510 and the image reconstructor 520 of FIG. 5, redundant descriptions thereof are omitted.

Referring to FIG. 6, the tomography apparatus 600 includes the data acquirer 610 and the image reconstructor 620. The tomography apparatus 600 may further include at least one selected from among a display 630, a gantry 640, a user interface 650, a memory 660, and a communicator 670. Since the display 630, the gantry 640, the user interface 650, the memory 660, and the communicator 670, which are included in the tomography apparatus 600, respectively have the same operations and structures as the display 130, the gantry 102, the input unit 128, the storage unit 124, and the communication unit 132 of the CT system 100 of FIG. 3, redundant descriptions thereof are omitted.

The data acquirer 610 acquires a first image which corresponds to a first time point and a second image which corresponds to a second time point by performing a tomography scan on an object. The first image and the second image may be 3D tomography images. The first image and the second image may be 2D tomography images which are 2D cross-sectional images. In detail, the first image and the second image may be cardiac images acquired by performing a tomography scan on a heart, which is a moving object, or may be four-dimensional (4D) cardiac images.

The image reconstructor 620 acquires first information which indicates a relationship between a motion amount of the object and a corresponding time amount, based on a motion amount between the first image and the second image. The image reconstructor 620 predicts a third image which corresponds to a third time point between the first and second time points based on the first information, and corrects the first information by using the predicted third image and measured data which corresponds to the third time point. The image reconstructor 620 reconstructs a final third image by using the corrected first information. Raw data may include projection data acquired by projecting X-rays to an object, and/or a sinogram that is a collection of pieces of the projection data. Raw data may be acquired by the gantry 640. Alternatively, the raw data may be acquired by an external tomography system (not shown) and received via the communicator 670.

In detail, the first information may be a value which corresponds to a motion vector field (MVF) between the first and second images. In particular, the first information may include information which indicates a relationship between a motion amount of the object corresponding to the MVF and the time. The first information will be described below in more detail with reference to FIGS. 12A, 12B, and 12C.

In detail, the image reconstructor 620 may compare information predicted in correspondence with the third time point by using the first information with information measured in correspondence with the third time point, and correct the first information such that a difference between the two pieces of information decreases. The correction of the first information by the image reconstructor 620 will be described in detail with reference to FIGS. 16 and 17.

The image reconstructor 620 may reconstruct a final third image by warping the measured data corresponding to the third time point, by using the corrected first information. The term "warping" signifies an adjustment of the object included in the image to fit to an expected state of the object via a change of the state of the object included in the image, such as, for example, expanding, contracting, moving, and/or shape transformation. In detail, the image reconstructor 620 may acquire a final third image that is a motion-corrected image, by performing motion correction such that the third image accurately shows a state of the object at the third time point by using the corrected first information.

The display 630 displays a predetermined screen image. In detail, the display 630 may display a user interface screen image which is useful for performing a tomography scan or a reconstructed tomography image. Screen images that are displayed on the display 630 according to exemplary embodiments will be described in detail below with reference to FIGS. 18-20B.

The gantry 640 may include the X-ray generator 106 of FIG. 3, the X-ray detecting unit 108 of FIG. 3, and the DAS 116 of FIG. 3. The gantry 640 projects X-rays toward the object, detects X-rays that have propagated through the object, and generates raw data which corresponds to the detected X-rays.

In detail, the X-ray generator 106 generates the X-rays. The X-ray generator 106 projects the generated X-rays toward the object while rotating around the object. Then, the X-ray detector 108 detects the X-rays which have propagated through the object. The DAS 116 produces the raw data which corresponds to the detected X-rays. The raw data may include projection data acquired by projecting radiation to the object, and/or a sinogram that is a collection of pieces of the projection data.

In the following description, reconstructing one cross-sectional tomography image by using the raw data acquired as the X-ray generator 106 rotates a half turn is referred to as a half reconstruction method, and reconstructing one cross-sectional tomography image by using the raw data acquired as the X-ray generator 106 rotates one turn is referred to as a full reconstruction method. Further, in the following description, a rotation time, angle, or phase of the X-ray generator 106 that rotates to acquire raw data needed to reconstruct one cross-sectional tomography image is referred to as "one cycle".

In addition, the term "one-cycle angular section" may denote an angular section during which the X-ray generator 106 rotates in order to acquire raw data needed for the reconstruction of one cross-sectional tomography image. Alternatively, the one-cycle angular section may denote a section of projection data needed to reconstruct one cross-sectional tomography image. In this case, the one-cycle angular section may be referred to as a one-cycle angular section of projection data.

For example, one cycle in the half reconstruction method may be 180° or more, and one cycle in the full reconstruction method may be 360°. For example, the one-cycle angular section of projection data in the half reconstruction method that uses the rebinned parallel beam may be an angle of 180°+fan angle by adding a fan angle to 180°. For example, when the fan angle is about 60°, the one-cycle angular section of projection data in the half reconstruction method may be about 240° (180°+60°). The one-cycle angular section in the full reconstruction method may be 420° (360°+60°) by adding the fan angle to 360°.

Reconstructing a tomography image by using raw data acquired in an angular section that is less than one cycle is referred to as a partial angle reconstruction (PAR) method.

The tomography apparatuses 500 and 600, according to exemplary embodiments, may be employed for all of the PAR method, the full reconstruction method, and the half reconstruction method.

In detail, the gantry 640 may acquire the raw data by performing a tomography scan according to at least one selected from among the PAR method, the full reconstruction method, and the half reconstruction method. The data acquirer 610 reconstructs the first and second images by using the raw data received from the gantry 640 or from an externally connected tomography system.

The user interface 650 produces and outputs a user interface (UI) image which relates to receiving a command or data from a user, and receives command or data from the user via the UI image. The UI image output by the user interface 650 is output to the display 630. Then, the display 630 may display the UI image. The user may recognize some information from the UI image displayed on the display 630 and may input a command or data via the UI mage.

For example, the user interface 650 may include any of a mouse, a keyboard, and/or an input device which includes hard keys for inputting predetermined data. For example, the user may input data or a command by manipulating at least one selected from among a mouse, a keyboard, and other input devices included in the user interface 650.

The user interface 650 may include a touch pad. In detail, the user interface 650 includes a touch pad (not shown) coupled with a display panel (not shown) included in the display 630 and outputs the UI image to the display panel. When a command is input via the UI image, the touch pad may sense the input operation and recognize the command input by the user.

In detail, when the user interface 650 includes a touch pad and the user touches a certain point on the UI image, the user interface 650 senses the touched point. Then, the user interface 650 may transmit sensed information to the image reconstructor 620. Then, the image reconstructor 620 may recognize a user's request or command in correspondence with a menu shown on the sensed point and may perform tomography image reconstruction according to the recognized request or command.

The memory 660 may store the data acquired according to the tomography scan. In detail, the memory 660 may store at least one selected from among projection data and a sinogram, which are raw data. The memory 660 may also store any of various kinds of data, programs, and the like necessary for reconstructing a tomography image, and also a finally-reconstructed tomography image. The memory 660 may also store various pieces of data needed for acquisition of the first information and the acquired first information.

The memory 660 may include at least one storage medium selected from among a flash memory type storage medium, a hard disk type storage medium, a multimedia card micro type storage medium, card type memory (for example, a secure digital (SD) or extreme digital (XD) memory), random access memory (RAM), static random access memory (SRAM), read-only memory (ROM), electrically erasable programmable ROM (EEPROM), programmable ROM (PROM), magnetic memory, a magnetic disk, and an optical disk.

The communicator 670 may perform communication with any of an external device, an external medical apparatus, and/or the like. For example, the communicator 670 may be connected to an external tomography system or apparatus and may receive the first image and the second image therefrom. Alternatively, the communicator 670 may receive raw data necessary for reconstructing the first image and the second image. In this case, the data acquirer 610 may receive the first image and the second image or the raw data necessary for reconstructing the first image and the second image, via the communicator 670. When the data acquirer 610 may receive the raw data, the image reconstructor 620 may reconstruct the first and second images based on the received raw data.

As described above, when an object moves as fast as the heart, motion artifacts are typically present within a reconstructed tomography image. An operation of the tomography apparatus 600 capable of increasing the quality of an image by minimizing occurrence of motion artifacts within a reconstructed tomography image will now be described in detail with reference to FIGS. 7-24.

In the tomography apparatuses 500 and 600 according to exemplary embodiments, the first image and the second image may be acquired according to any of a variety of scan modes. In the tomography apparatuses 500 and 600 according to exemplary embodiments, the X-ray generator 106 which generates X-rays that are emitted in any of a variety of shapes may be employed.

The image reconstruction method, the scan mode, and the radiation shape of X-rays which are applicable to the tomography apparatuses 500 and 600 will now be described in detail with reference to FIGS. 7-9B.

Figure 7:
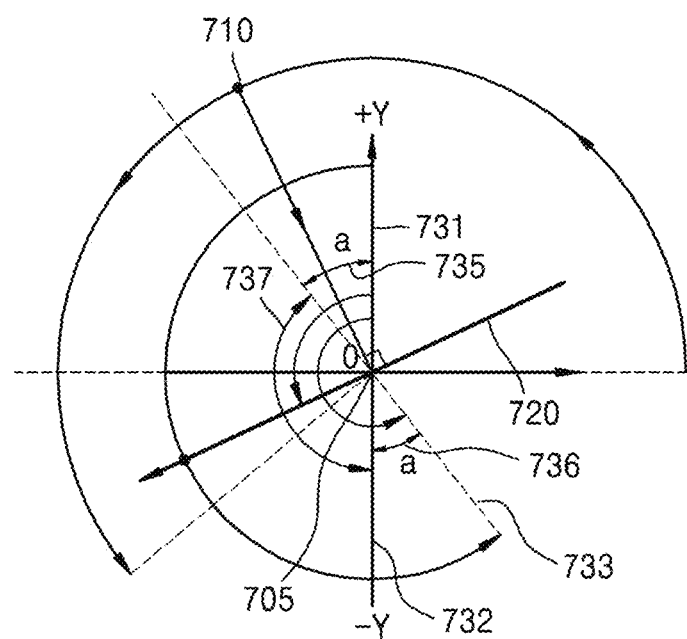
FIG. 7 is a view which illustrates reconstruction of a tomography image according to a half reconstruction method.

FIG. 7 is a view which illustrates a reconstruction of a tomography image according to the half reconstruction method.

Referring to FIG. 7, when the X-ray generator 106 projects a cone beam having a fan shape at a predetermined position, the X-ray generator 106 may perform a tomography scan while rotating by an angle equivalent to an angle of 180°+(fan angle×2) in the half reconstruction method, and may reconstruct a tomography image by using raw data acquired at the angle of 180°+(fan angle×2). When a reconstruction operation is performed by converting the fan beam to a parallel beam, or when the X-ray generator 106 projects a parallel beam, a tomography image may be reconstructed by using raw data corresponding to the angular section having an angle of 180°+fan angle in the half reconstruction method. In particular, when a cone beam is used, the amount of raw data required increases as the fan angle increases, as compared with a case of reconstructing a tomography image by using the raw data acquired by using the parallel beam.

Figure 9A:
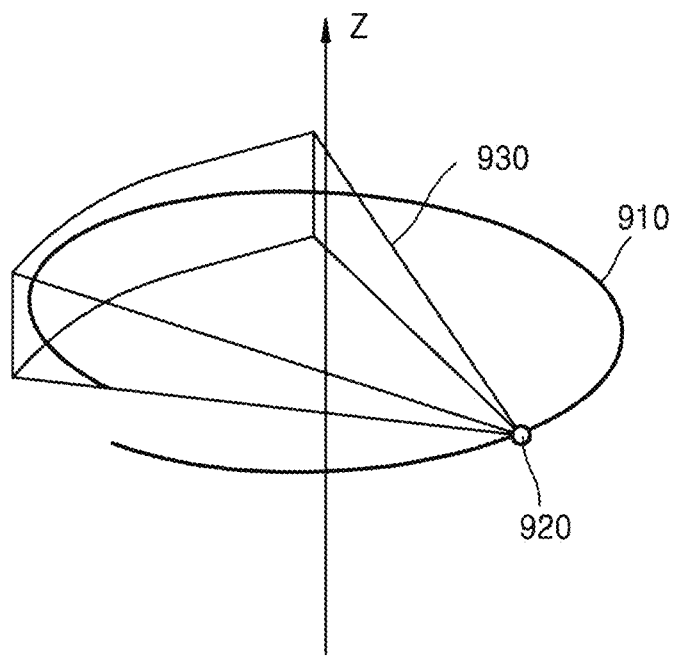
FIGS. 9A and 9B are views which illustrate a shape of an X-ray beam projected toward an object.
Figure 9B:
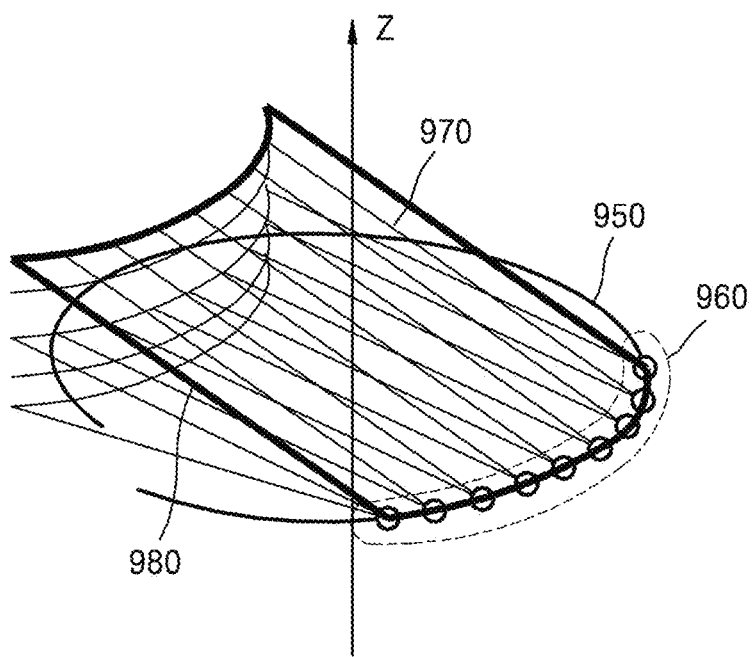

In detail, when a beam is not a cone beam but a parallel beam as described in FIG. 9B, the angle for additional rotation is decreased to be less than the fan angle "a" for the case of a cone beam, and the X-ray generator 106 rotates by an angle of 180°+a as one cycle. For example, when the fan angle is 60°, the raw data acquired in the angular section of 300° (180°+2a) is needed for a case of using a cone beam, and the raw data acquired in the angular section of 240° (180°+a) is needed for a case of using a parallel beam. Accordingly, when a parallel beam is used, the half reconstruction method may be performed at an angle 240° (180°+a) as one cycle.

FIG. 7 illustrates a case of using a parallel beam, in which the half reconstruction method is performed by using raw data acquired in the angular section of, for example, 180°+fan angle "a".

Referring to FIG. 7, when the X-ray generator 106 at a beam position 710 projects X-rays toward an object 705, the X-ray detector 108 detects the X-rays on a detection plane 720. The beam position 710 rotates around the object 705 as a center by an angle of 180°+a, which is one cycle. The detection plane 720 rotates in correspondence with the beam position 710. In detail, the beam position 710 moves by 180° from a +Y axis to a −Y axis and further moves by the fan angle equivalent to "a", to a position 733.

In the half reconstruction method, one cross-sectional tomography image is reconstructed by using pieces of projection data acquired in a first "a" angular section 735, an intermediate angular section 737, and a last "a" angular section 736.

As the time taken to acquire raw data necessary for reconstructing a cross-sectional tomography image decreases, an image having reduced motion artifacts may be reconstructed.

In addition, as the time taken to acquire raw data necessary for reconstructing one cross-sectional tomography image decreases, a temporal resolution may be increased. Accordingly, when the X-ray generator 106 rotates at a predetermined speed, a tomography image reconstructed according to the half reconstruction method may have a higher temporal resolution than a tomography image reconstructed according to the full reconstruction method.

Moreover, the tomography apparatuses 500 and 600 according to exemplary embodiments may acquire the first image and the second image by performing a tomography scan according to any of a variety of scan modes. Examples of the scan modes used for a tomography scan may include a prospective mode and a retrospective mode, which will be described below in detail with reference to FIGS. 8A and 8B. The tomography apparatuses 500 and 600 according to exemplary embodiments may perform a tomography scan according to any of a variety of scanning methods. Examples of the scanning methods used for a tomography scan include an axial scanning method and a helical scanning method, which will now be described in detail with reference to FIGS. 8A and 8B.

Figure 8A:
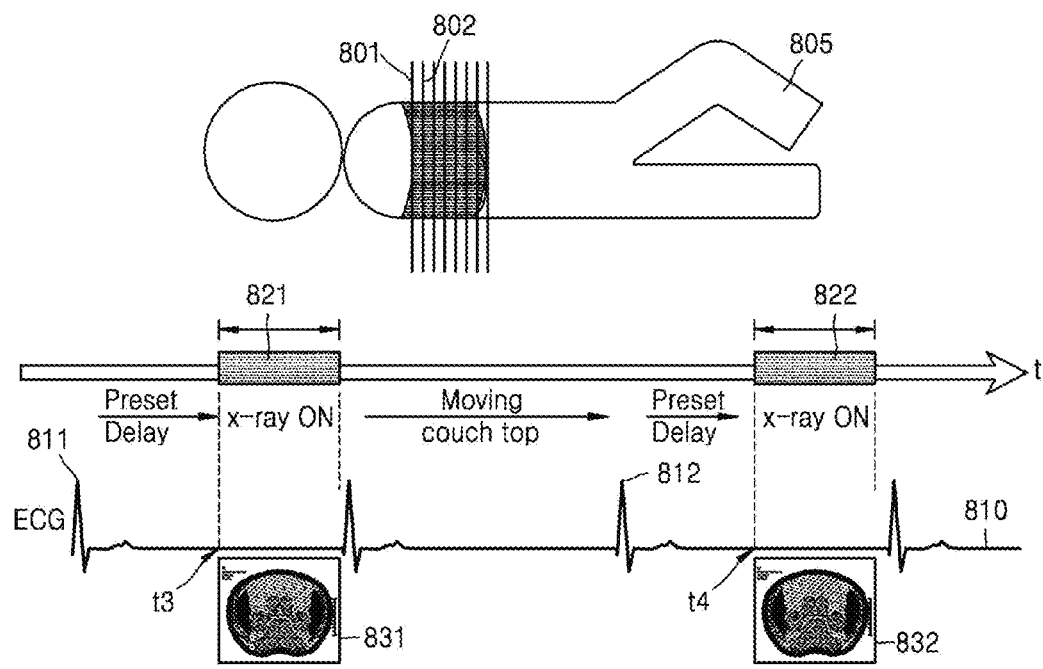
FIGS. 8A and 8B are views which illustrate a scan mode and a scanning method that are applied to a tomography scan.
Figure 8B:
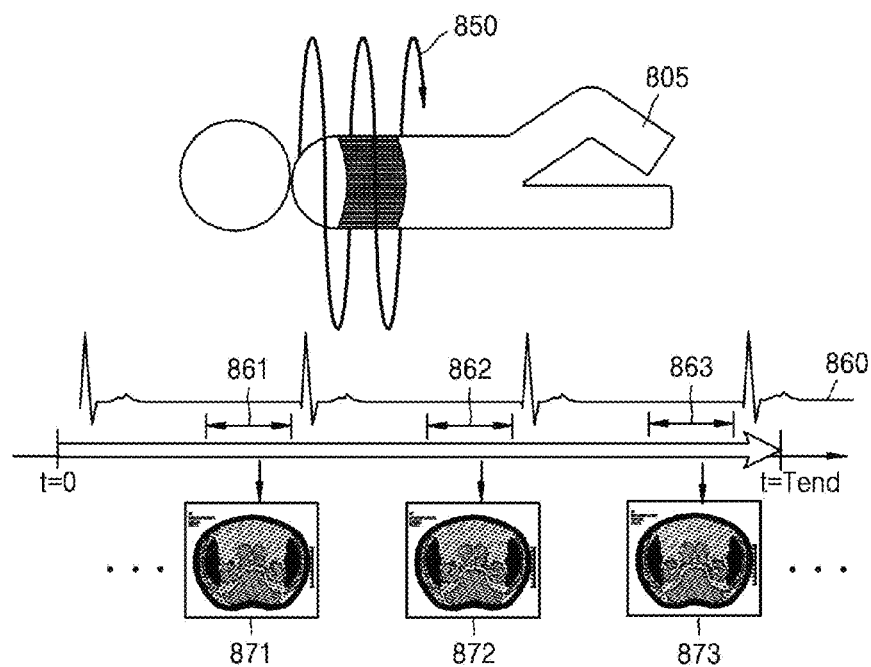

FIGS. 8A and 8B are views which illustrate a scan mode and a scanning method that are applied to a tomography scan. In detail, FIG. 8A is a view which illustrates a tomography scan according to an axial scanning method. Additionally, FIG. 8A is a view which illustrates a tomography scan according to a prospective mode. FIG. 8B is a view which illustrates a tomography scan according to a helical scanning method. Additionally, FIG. 8B is a view which illustrates a tomography scan according to a retrospective mode.

The scan mode may be determined according to whether or not a heartbeat rate of a patient that is subject to imaging is constant. Electrocardiographic (ECG) gating may be used to acquire raw data that is used for reconstruction of an image. In FIGS. 8A and 8B, while a tomography scan is performed, the table 105 of FIG. 3 is moved in an axial direction of a patient 805.

Referring to FIG. 8A, the axial scanning method is a tomography method in which X-rays are projected for scanning while the table 105 of FIG. 3 is stopped, the table 105 is moved by a predetermined interval from 801 to 802, and then X-rays are projected for a predetermined section 822, thereby obtaining raw data. The tomography apparatuses 500 and 600 according to the present exemplary embodiments may perform a tomography scan by using the axial scanning method and thus acquire at least one selected from the first image, the second image, the third image, and the final third image.

Referring to FIG. 8A, for a person having a constant heart beat rate, an ECG signal 810 is regularly gated by employing a prospective mode. In the prospective mode, a predetermined section 821, which is at a time point t3 spaced apart from an R peak 811 by a predetermined time period, is automatically selected. X-rays are applied to the object 805 during the gated predetermined section 821 in order to acquire raw data. In the prospective mode, the predetermined section 822, which is at a time point t4 spaced apart from an R peak 812 by a predetermined time period, is automatically selected. At this time, X-rays are projected for scanning while the table 105 of FIG. 3 is stopped, the table 105 is moved by the predetermined interval from 801 to 802, and then X-rays are projected for the predetermined section 822, thereby obtaining raw data. A method for performing a tomography scan by moving in an axial direction of an object as illustrated in FIG. 8A is referred to as an axial reconstruction method. In detail, as a half reconstruction method, a method for performing a tomography scan by moving in an axial direction of an object as illustrated in FIG. 8A is referred to as an axial half reconstruction method. The tomography apparatuses 500 and 600 according to the present exemplary embodiments may employ the axial scanning method.

The data acquirer 610 reconstructs tomography images 831 and 832 by using the pieces of raw data acquired in the gated sections 821 and 822.

Referring to FIG. 8B, the helical scanning method is a tomography method in which X-rays are continuously projected for scanning while the table 105 of FIG. 3 is moved during a predetermined time period from t=0 to t=end. In detail, a tomography scan is performed by continuously moving, for a predetermined time period at a predetermined speed, the table 105 of FIG. 3 on which the patient 805 including the object is laid, and continuously projecting X-rays to an object while the table 105 is moving. Accordingly, a motion trajectory 850 of the X-rays may be in a helix form.

Referring to FIG. 8B, when a heartbeat rate of a patient is irregular, as in the case of an arrhythmia patient, regularity of a heart beat rate is degraded, and thus it may be impossible to uniformly detect the cycle as in the prospective mode. In this case, an ECG signal 860 is irregularly gated in the retrospective mode. In the retrospective mode, raw data is acquired by radiating X-rays in all cycles of ECG signals or in consecutive predetermined cycles of ECG signals, and then partial cycles for tomography image reconstruction are selected. In particular, in the retrospective mode, after a user individually sets partial cycles for use in image reconstruction to detect partial cycles 861, 862, and 863, the user uses pieces of raw data respectively acquired during the detected partial cycles 861, 862, and 863 in tomography image reconstruction.

In detail, in the retrospective mode, X-rays are continuously projected for a certain time period from t=0 to t=end, thereby performing a tomography scan. Since the table 105 of FIG. 3 continuously moves at a predetermined speed for a predetermined period time, the motion trajectory 850 of the X-rays is in a helix form.

A method for performing an X-ray scan by continuously projecting X-rays while the table is being moved such that the motion trajectory 850 has a helix form as illustrated in FIG. 8B is referred to as a helical reconstruction method. In detail, among half reconstruction methods, the method for performing an X-ray scan by continuously projecting X-rays while the table is being moved as illustrated in FIG. 8B is referred to as a helical half reconstruction method. The tomography apparatuses 500 and 600 according to the present exemplary embodiments may employ a helical half reconstruction method.

In a detailed example, for a patient having an irregular heart beat rate, a tomography scan may be performed by applying the retrospective mode to the helical scanning method. For a patient having a regular heart beat rate, a tomography scan may be performed by applying the prospective mode to the axial scanning method. However, exemplary embodiments are not limited thereto, and a tomography scan may be performed by applying the prospective mode to the helical scanning method or by applying the retrospective mode to the axial scanning method.

FIGS. 9A and 9B are views which illustrate a shape of an X-ray beam projected toward the object. In detail, FIG. 9A illustrates an example in which the X-ray generator 106 projects X-rays in the form of a cone beam. FIG. 9B illustrates an example in which the X-ray generator 106 projects X-rays in the form of a parallel beam.

Referring to FIG. 9A, when the X-ray generator 106 moves along a trajectory 910 and projects X-rays at a predetermined position 920, the X-rays are projected toward the object in a cone shape 930, as illustrated in FIG. 9A.

Referring to FIG. 9B, when the X-ray generator 106 moves along a trajectory 950 and projects X-rays at a predetermined position 960, the X-rays are projected toward the object in a parallel plane shape 970, as illustrated in FIG. 9B.

Referring to FIG. 9B, when the X-ray generator 106 projects X-rays in the form of a cone beam, the X-ray beams projected in the form of a cone are rearranged to be in parallel on a plane 980 that is formed by connecting the row of the X-ray detector 108 and the position 960 at which the X-ray generator 106 is positioned. In particular, the cone beam may be converted into a pseudo parallel-beam for use. When the cone beam is converted into a parallel beam for use, in the cone beam, the X-ray generator 106 needs to acquire raw data by further rotating the fan angle "a", as compared with the parallel beam. In detail, when the fan angle is "a", the X-ray generator 106 that projects a cone beam may acquire raw data which corresponds to the angular section having an angle of 180°+a which corresponds to the rebinned parallel beam, by using the raw data acquired in the angular section having an angle of 180°+2a.

As described above with reference to FIGS. 9A and 9B, the tomography apparatuses 500 and 600 according to the present exemplary embodiments may be applied to both of a tomography apparatus radiating a cone beam and a tomography apparatus radiating a parallel beam.

For convenience of explanation, in the half reconstruction method, an angular section except for 180° in the one-cycle angular section that is an angular section that the X-ray generator 106 rotates to acquire projection data needed for acquiring one cross-sectional tomography image will now be referred to as an additional angle. In the above-described example, when a rebinned parallel beam obtained by rebinning the cone beam projected from the X-ray generator 106 is used, the additional angle may be "2a". When a parallel beam projected from the X-ray generator 106 is used, the additional angle may be "a". When the rebinned parallel beam is used, the X-ray generator 106 acquires the projection data corresponding to the angular section having an angle of 180°+a by using the raw data acquired while rotating the angular section having an angle of 180°+2a. Assuming a section of the projection data acquired to reconstruct one cross-sectional tomography image to be the one-cycle angular section, the additional angle may signify an angular section obtained by subtracting 180° from the one-cycle angular section of the projection data. In the above-described example, when the X-ray generator 106 rotates the angular section having an angle of 180°+2a projecting a cone beam and thus the projection data corresponding to the angular section having an angle of 180°+a is acquired by using the rebinned parallel beam, the one-cycle angular section of the projection data may be 180°+a, and the additional angle in the one-cycle angular section of the projection data may be "a".

In addition, when the X-ray generator 106 performs a tomography scan by projecting a cone beam toward the object and acquires first information and a tomography image by using the rebinned parallel beam as in the above-described example, the one-cycle angular section for rotation of the X-ray generator 106 may be 180+2*fan angle (=180+2a), and the additional angle may be 2*fan angle (=2a).

When the tomography apparatuses 500 and 600 according to the present exemplary embodiments perform a CT scan, both a single slice CT method in which a CT scan is performed using a single slice and a multi-slice CT method in which a CT scan is performed using a plurality of slices may be applied. The tomography apparatuses 500 and 600 according to the present exemplary embodiments may be applied to both a single source single detector (or a single source tomography apparatus) that uses one light source and one detector to perform a CT scan, and to a two source two detector (or a dual source tomography apparatus) that uses two light sources and two detectors to perform a CT scan. The light source denotes the X-ray generator 107 and the detector denotes the X-ray detector 108.

Figure 10:
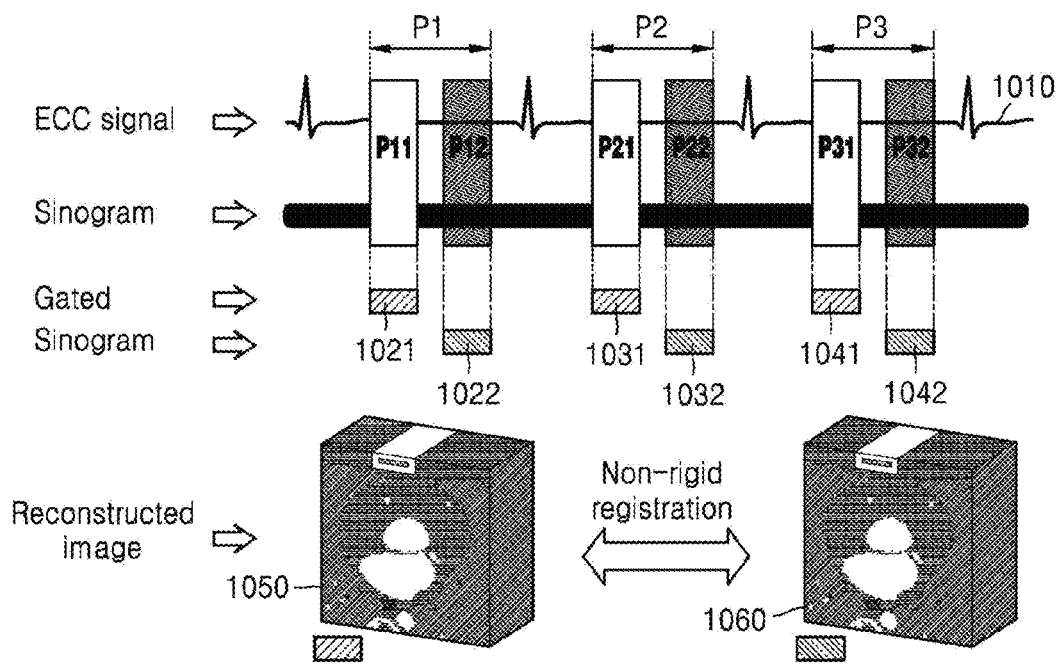
FIG. 10 is a schematic diagram which illustrates an operation of the tomography apparatus of FIG. 6.

FIG. 10 is a schematic diagram which illustrates an operation of the tomography apparatus 600, according to an exemplary embodiment.

The data acquirer 610 acquires a first image which corresponds to a first time point and a second image which corresponds to a second time point. In detail, the first image and the second image are acquired by performing a tomography scan on the same object at different time points. A sinogram which includes a plurality of pieces of projection data will now be exemplified as raw data, and a case in which the first and second images are 3D tomography images will now be described.

In detail, when a user desires to reconstruct a tomography image of an object at a time point included in a predetermined time section, the first time point may correspond to a lower limit of the predetermined time section, and the second time point may correspond to an upper limit of the predetermined time section. For example, when a user wants to reconstruct a tomography image of a heart at a time point included in a time section between t1 and t2, the first time point may be t1 and the second time point may be t2. The time section between t1 and t2 is referred to as a total time section, and the total time section is P1, P2, or P3. For example, the time section between t1 and t2 may correspond to a beat rate of a heart.

Referring to FIG. 10, the data acquirer 610 may acquire a sinogram 1021 at a first time section P11 corresponding to the first time point t1 and a sinogram 1022 at a second time section P12 corresponding to the second time point t2. The data acquirer 610 may reconstruct a first image 1050 by using the sinogram 1021 and reconstruct a second image 1060 by using the sinogram 1022. For example, the first time point t1 may be a middle point of the first time section P11 and the second time point t2 may be a middle point of the second time section P12.

Any of various reconstruction methods may be used to reconstruct a tomography image. For example, as a method for reconstructing a tomography image in the tomography apparatuses 500 and 600, any of a back projection method, a filtered back-projection method, an iterative method, a matrix inversion method, an analytical method, or the like may be used.

According to the back projection method, an image is reconstructed by back-projecting projection data acquired in a plurality of views to a pixel plane and summing the back-projected data. In detail, the back projection method may entail acquiring an image similar to a real image by using multiple pieces of projection data in a plurality of directions. Further, filtering may be additionally performed in order to remove artifacts existing in a reconstructed image and to improve image quality.

The filtered back-projection method is an improvement to the back projection method and removes blurring or artifacts that may occur in the back projection method. According to the filtered back-projection method, raw data is filtered before back projection is performed, and the filtered raw data is back projected, thereby reconstructing a tomography image.

The filtered back-projection method is generally widely used for reconstruction of a tomography image, is a method that may be simply embodied, and is effective in terms of a calculation amount for image reconstruction. The filtered back-projection method is a method that mathematically induces a reverse transformation from a Radon transformation, which is a process of acquiring a sinogram from a 2D image. According to the filtered back-projection method, it is relatively simple to extend a 2D image to a 3D image. In detail, in the filtered back-projection method, an image is reconstructed by performing back projection after filtering projection data by using a Shepp and Logan filter that is a type of high pass filter.

In the following description, a case of reconstructing a tomography image by using a filtered back projection method is described as an example.

In detail, the data acquirer 610 gates a plurality of first time sections P11, P21, and P31 for generating the first image 1050 at a plurality of cycles of an ECG signal. Sinograms 1021, 1031, and 1041 are respectively acquired in the first time sections P11, P21, and P31. The data acquirer 610 also gates a plurality of second time sections P12, P22, and P32 for generating the second image 1060 at the plurality of cycles of the ECG signal. Sinograms 1022, 1032, and 1042 are respectively acquired in the second time sections P12, P22, and P32. The data acquirer 610 may reconstruct the first image 1050 by back-projecting the sinograms 1021, 1031, and 1041, and may reconstruct the second image 1060 by back-projecting the sinograms 1022, 1032, and 1042.

Then, the data acquirer 610 may generate first information by comparing the first image 1050 with the second image 1060. The generation of the first information will be described below in more detail with reference to FIGS. 12A, 12B, and 12C.

Although FIG. 10 illustrates a case in which sinograms acquired in a plurality of time sections are used to reconstruct the first image 1050 and the second image 1060, the first image 1050 and the second image 1060 may be reconstructed by using a sinogram acquired in a single time section.

Reconstruction of the first image 1050 and the second image 1060 via ECG gating will now be described in detail with reference to FIGS. 11A and 11B.

Figure 11A:
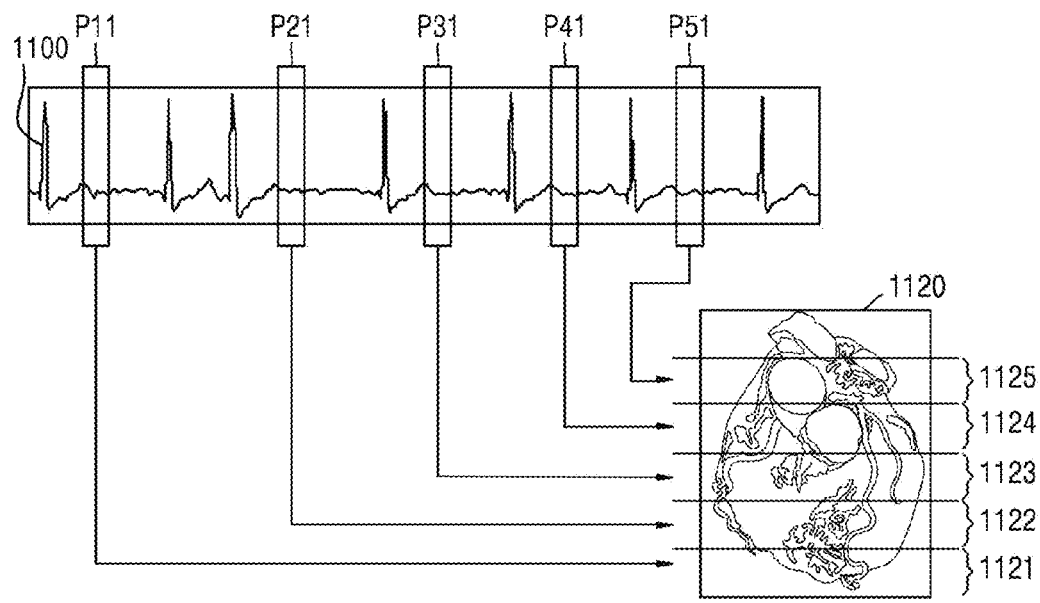
FIGS. 11A and 11B are schematic diagrams which illustrate reconstructions of a first image and a second image, according to an exemplary embodiment.
Figure 11B:
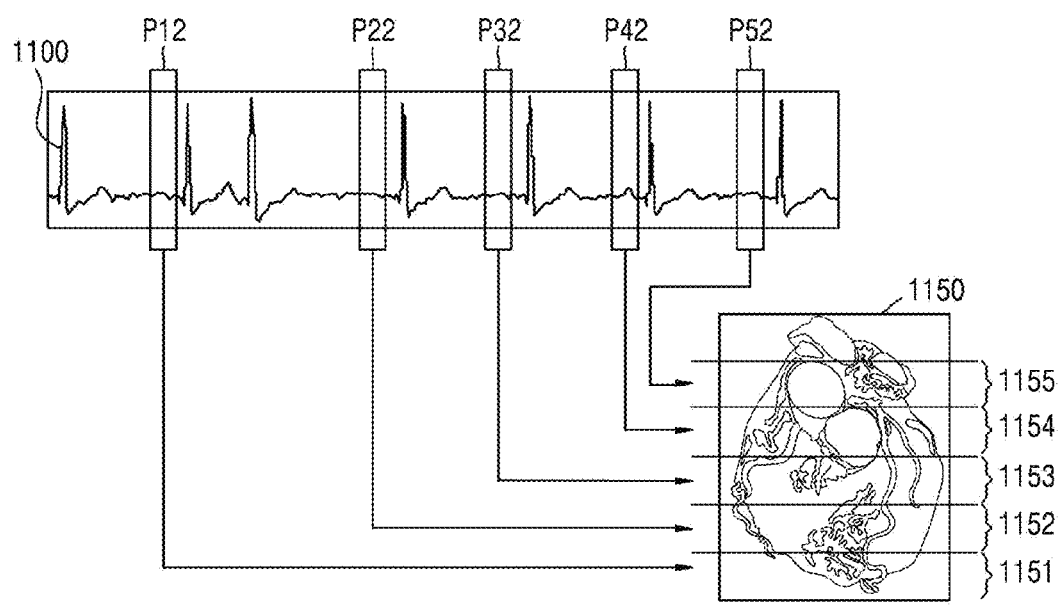

FIGS. 11A and 11B are schematic diagrams which illustrate a reconstruction of a first image 1120 and a second image 1150 according to an exemplary embodiment. In detail, FIG. 11A is a view which illustrates a generation of the first image 1120. FIG. 11B is a view which illustrates a generation of the second image 1150. The first image 1120 and the second image 1150 identically correspond to the first image 1050 and the second image 1060 of FIG. 10, respectively.

FIGS. 11A and 11B illustrate a case in which the first and second images 1120 and 1150 are 3D tomography images that express a heart three-dimensionally. The 3D tomography images may be reconstructed to represent any of various views such as a sagittal view, a coronal view, and a transaxial view. The first image and the second image reconstructed by the image reconstructor 620 may be 2D tomography images.

Referring to FIG. 11A, the data acquirer 610 extracts a plurality of time sections P11, P21, P31, P41, and P51 during which a motion of a heart is minimized, by gating an ECG signal 1100. A plurality of image sections 1121, 1122, 1123, 1124, and 1125 are reconstructed using sinograms respectively acquired in the plurality of time sections P11, P21, P31, P41, and P51. In FIG. 11A, the time sections P11, P21, and P31 identically correspond to the time sections P11, P21, and P31 of FIG. 10, respectively.

In detail, the data acquirer 610 reconstructs the first image section 1121 by using the sinogram acquired during the time section P11, reconstructs the second partial image section 1122 by using the sinogram acquired during the time section P21, and reconstructs the third image section 1123 by using the sinogram acquired during the time section P31. The data acquirer 610 reconstructs the fourth image section 1124 by using the sinogram acquired during the time section P41 and reconstructs the fifth image section 1125 by using the sinogram acquired during the time section P51.

The first image 1120 may be reconstructed by synthesizing the plurality of image sections 1121, 1122, 1123, 1124, and 1125.

Referring to FIG. 11B, the data acquirer 610 extracts a plurality of time sections P12, P22, P32, P42, and P52 during which a motion of a heart is minimized, by gating the ECG signal 1100. A plurality of image sections 1151, 1152, 1153, 1154, and 1155 are reconstructed using sinograms respectively acquired in the plurality of time sections P12, P22, P32, P42, and P52. In FIG. 11B, the time sections P12, P22, and P32 identically correspond to the time sections P12, P22, and P32 of FIG. 10, respectively.

In detail, the data acquirer 610 reconstructs the first image section 1151 by using the sinogram acquired during the time section P12, reconstructs the second image section 1152 by using the sinogram acquired during the time section P22, and reconstructs the third image section 1153 by using the sinogram acquired during the time section P32. The data acquirer 610 reconstructs the fourth image section 1154 by using the sinogram acquired during the time section P42 and reconstructs the fifth image section 1155 by using the sinogram acquired during the time section P52.

The second image 1150 may be reconstructed by synthesizing the plurality of image sections 1151, 1152, 1153, 1154, and 1155.

Figure 12A:
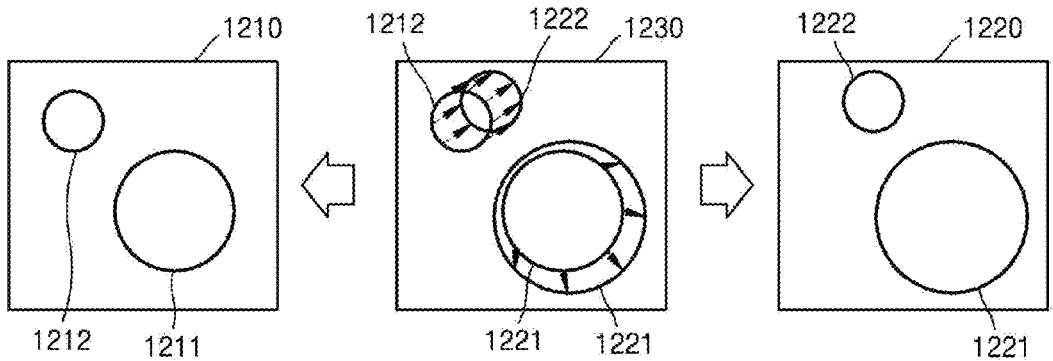
FIGS. 12A, 12B, and 12C are views which illustrate an operation of acquiring first information by measuring motion of an object.
Figure 12B:
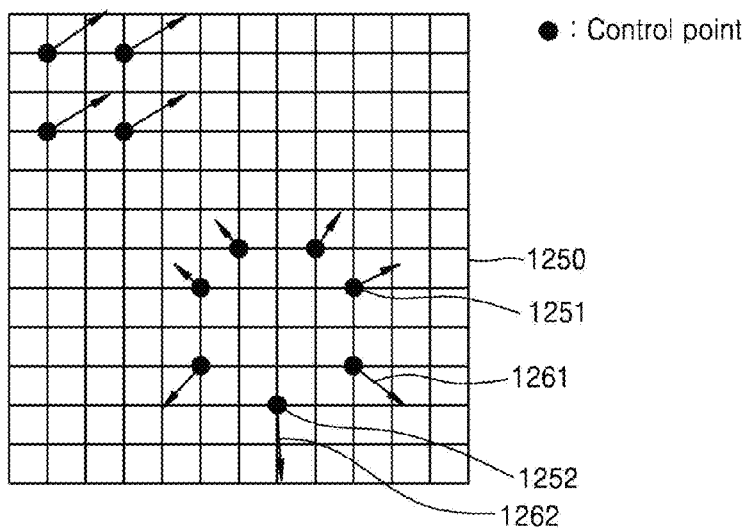
Figure 12C:
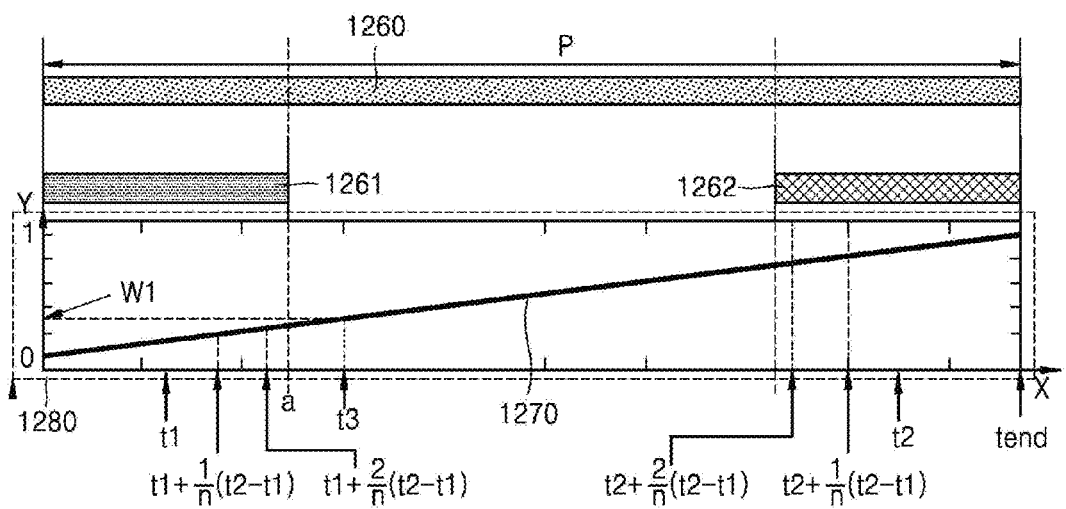

FIGS. 12A, 12B, and 12C are views which illustrate an operation of acquiring first information by measuring a motion of an object. An operation in which the image reconstructor 620 acquires the first information will now be described in detail with reference to FIGS. 10-12C. In detail, FIG. 12A is a view which illustrates a comparison between a first image 1210 and a second image 1220. FIG. 12B is a view which illustrates a motion amount between the first image 1210 and the second image 1220. FIG. 12C is a view which illustrates first information 1280.

Referring to FIG. 12A, the first image 1210 and the second image 1220 identically correspond to the first image 1050 and the second image 1060 of FIG. 10, respectively. However, for convenience of explanation, FIG. 12A simply illustrates the first image 1210 and the second image 1220.

A case in which the first image 1210 and the second image 1220 are 2D images and the surface of an object is shown as an edge within an image will now be described.

Referring to FIG. 12A, the first image 1210 and the second image 1220 are schematic illustrations of tomography images obtained by scanning a moving object. In FIG. 12A, at least one object, namely, objects 1211 and 1212 or objects 1221 and 1222 included in one image, is expressed as a circular object.

In detail, in order to compare the respective amounts of motions of the objects, the objects 1211 and 1212 included in the first image 1210 are compared with the objects 1221 and 1222 included in the second image 1220, respectively. According to a result of the comparison, the motion amount of each of the objects may be obtained as illustrated in a comparative image 1230.

Referring to FIG. 12B, the surfaces indicating the same portions of the objects included in the first and second images 1210 and 1220 may be compared with each other, and thus, motion vectors which indicate positional difference values and directions between the compared surfaces may be obtained. The motion vector may be used as a representation of the amount of the motion of the object. Information that includes motion vectors and indicates a motion amount of a predetermined portion of the object may include a motion vector field (MVF). In particular, the MVF indicates a motion amount of a surface forming the object.

The MVF is information acquired for extraction of motion of the object, and the motion amount of the object may be measured by using non-rigid registration. The motion amount of the object may be measured by using any of a variety of motion measurement techniques, such as rigid registration, an optical flow technique, and a feature matching technique.

In the following description, a case of using the non-rigid registration to acquire the MVF is described as an example.

In detail, a plurality of control points are set in an image grid of the first image 1210 or the second image 1220, and an optimal motion vector is calculated at each control point. The motion vector is a vector which includes the direction and the magnitude of the motion. The respective motion vectors at the control points are interpolated to obtain the MVF which indicates motion vectors in all voxels. For example, a B-spline free form deformation method may be used as a motion vector interpolation method. An optimization technique may be used as a method for calculating an optimal motion vector at each control point. In detail, according to the optimization technique, the MVF is updated by repeatedly updating the motion vectors at each of the plurality of control points, the first image 1210 or the second image 1220 is warped based on the updated MVF, and then a warped first or second image is compared with the second image 1220 or the first image 1210 before warping. When a degree of similarity between an image before warping and an image after warping is sufficiently high, the repetition is terminated and an optimal motion vector is calculated. The degree of similarity may be indicated by using a negative value of a sum of squared differences of brightness values of two images to be compared.

In another method, the motion vectors may be obtained by setting a plurality of control points on a surface of the object and comparing the control points indicating the same positions in the objects in the first image 1210 and the second image 1220. In detail, a relative difference between the control points is obtained by matching the control points of the object in the first image 1210 to the control points of the object in the second image 1220. The relative difference value may be used as a motion vector at a current control point. Then, the respective motion vectors at the control points are interpolated to obtain the MVF which indicates motion vectors in all voxels. Similarly as in the above-described example, a B-spline free form deformation method may be used as a motion vector interpolation method.

Referring to FIG. 12C, a total time section 1260, a first time section 1261, and a second time section 1262 identically correspond to the total time section (e.g., P1), the first time section P11, and the second time section P12 of FIG. 10, respectively.

In FIG. 12C, which is a graph that depicts the first information 1280, an x-axis denotes a total time section, and a y-axis denotes a motion amount. In detail, when the amount of motion of an object within an MVF is represented by values between zero (0) and one (1), the Y axis denotes a quantized motion amount of the object. For example, when the absolute values of motion vectors within the MVF are equivalent to the motion amounts of the object, the absolute values of the motion vectors may be converted into the values between 0 and 1.

In detail, the first information 1280 may include information which indicates a relationship between a motion amount of the object in the MVF between the first image 1210 and the second image 1220 and a corresponding time amount. The time amount may be based on a time section set by a user or the like. The time amount may also be based on a time section between the first time point t1 and the second time point t2. For example, if a user wants to observe a motion of an object for two seconds, the user may set the total time section 1260 to be equivalent to two seconds. When two time points when motion of the object is the smallest are set to be the first time point t1 and the second time point t2, the time section between the first time point t1 and the second time point t2 may be set as the total time section 1260.

When a motion amount of the second image 1220, which has been reconstructed by using a sinogram acquired in the second time section 1262, is measured by using the first image 1210, which has been reconstructed by using a sinogram acquired in the first time section 1261, which is a start section of the total time section 1260, as a reference image, the motion amount of the first image 1210 may have a 0% motion value and the motion amount of the second image 1220 may have a 100% motion value.

In detail, when the motion amount of the object and the corresponding time amount have a linear relationship, the data acquirer 610 may respectively match a zero MVF and the MVF that indicates a motion amount between the first and second images 1210 and 1220, with a minimum weighting value or 0% and a maximum weighting value or 100%. In detail, the zero MVF may correspond to a start point t=0 of the total time section 1260, and the MVF which indicates a motion amount between the first and second images 1210 and 1220 may correspond to an end point of the total time section 1260. In detail, when the MVF between the first and second images 1210 and 1220 has been calculated, the motion amount having 100% motion value may be a sum, an average, or the like of the absolute values of all motion vectors in the MVF between the first and second images 1210 and 1220. In the first information 1280, the motion amount may be expressed as a weighting value into which the motion amount calculated in the MVF is converted.

In FIG. 12C, the MVF corresponding to a motion amount between the first and second images 1210 and 1220 is quantified to have values between 0 and 1. A value of the Y axis corresponding to a motion amount of the object in the first information 1280 will now be referred to as a weighting value.

As illustrated in FIG. 12C, a relationship between the time amount and the weighting value in the first information 1280 may have linearity. For example, when the total time section 1260 is short, for example, about 0.2 seconds, the relationship between the time and the weighting value in the first information 1280 may have linearity. In detail, the weighting value and the time may be displayed as a graph 1270.

The shape of the graph 1270 representing the relationship between the weighting value and the time in the first information 1280 may correspond to a motion pattern of the object. For example, when the total time section 1260 is relatively long, for example, about 1 to 2 seconds, the relationship between the time and the weighting value in the first information 1280 may be determined according to a relationship that may be modeled by a quadratic equation or a relationship that may be modeled by statistical information.

For example, a motion pattern of the object may be statistically modeled. In detail, when the object is a heart, motion of the heart may be statistically modeled, and the shape of the graph 1270 in the first information 1280 may be set to correspond to the modeled motion of the heart.

In the first information 1280, the graph 1270 indicating the relationship between the weighting value and the time may have an initially set shape. In the first information 1280, the graph 1270 indicating the relationship between the weighting value and the time may have a shape that is set by a user via the user interface 650.

In the first information 1280, the shape of the graph 1270 indicating a motion pattern of the object may vary according to the object. For example, when the object is the entire heart, the shape of the graph 1270 in the first information 1280 may reflect a motion pattern of the entire heart. When the object is a coronary artery that is included in the heart, the shape of the graph 1270 of the first information 1280 may reflect a motion pattern of the coronary artery. Even when the object is the coronary artery included in the heart, the motion pattern may vary according to the position of the coronary artery in the heart, and thus the shape of the graph 1270 of the first information 1280 may be set to vary according to the position of the coronary artery. When the object is a mitral valve (MV) that is included in the heart, the shape of the graph 1270 of the first information 1280 may reflect the motion pattern of the MV.

Further, the motion pattern may vary according to each partial area of the object to be tomography scanned. In this case, the first information 1280 may be acquired for each partial area to reflect a different motion pattern for each partial area. A target image which indicates the entire object may be reconstructed by performing motion correction for each partial area by using the first information that is acquired separately for each partial area. For example, when the object is a heart, the left ventricle, the right ventricle, the left atrium, and the right atrium may have different motion patterns. In this case, the first information may be individually acquired for each of the left ventricle, the right ventricle, the left atrium, and the right atrium, motion correction is performed on a partial image of each of the left ventricle, the right ventricle, the left atrium, and the right atrium, and the motion-corrected partial images are synthesized in order to reconstruct a target image which indicates the heart.

The center of the first time section 1261 may be the first time point t1, and the center of the second time section 1262 may be the second time point t2.

The user interface 650 may produce a UI image (not shown) which relates to selecting the first time point t1 and the second time point t2. Then, a user may select and input the first time point t1 and the second time point t2 via the UI image. For example, the UI image may display an ECG signal of a patient, and the user may select predetermined time points of the ECG signal as the first time point t1 and the second time point t2 from the UI image.

Figure 13A:
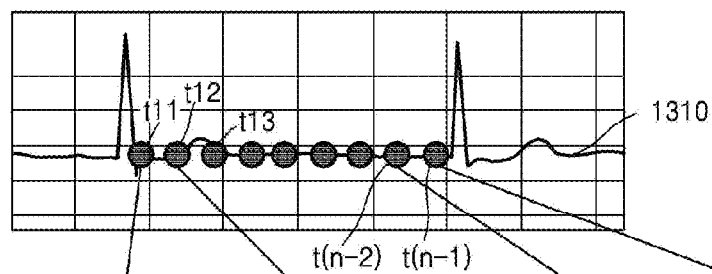
FIGS. 13A, 13B, and 13C are schematic diagrams which illustrate an operation of the tomography apparatus of FIG. 6.
Figure 13B:
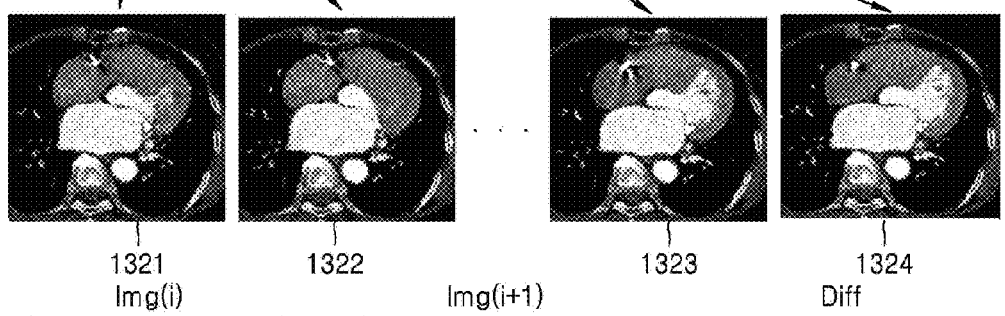
Figure 13C:
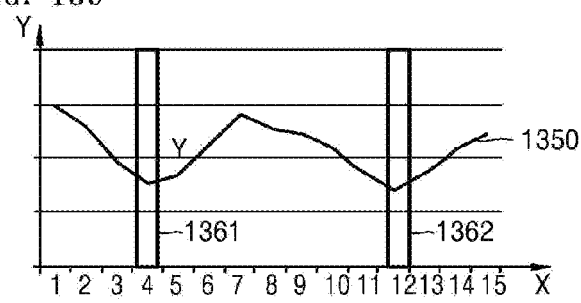

The data acquirer 610 may select the two time points when motion of an object is minimized within a predetermined time section as the first time point t1 and the second time point t2. The setting of the first and second time points t1 and t2 will be described in detail later with reference to FIGS. 13A, 13B, 13C, 14A, and 14B. The predetermined time section may be an R-R section between an R peak of the ECG signal and a subsequent R peak thereof. FIGS. 13A, 13B, and 13C are schematic diagrams which illustrate an operation of the tomography apparatus 600, according to another exemplary embodiment.

The data acquirer 610 may reconstruct an image at intervals of a second time period within a predetermined time section, measure a difference between an image reconstructed at one time point and an image reconstructed at another time point adjacent to the one time point, and select two time points when motion of an object is minimized as a first time point and a second time point based on the measured difference.

Referring to FIG. 13A, the data acquirer 610 reconstructs images at intervals of a predetermined time from an ECG signal 1310. For example, referring also to FIG. 13B, the data acquirer 610 reconstructs a tomography image 1321 by using a sinogram gated in a time section corresponding to a time point t11 and reconstructs a tomography image 1322 by using a sinogram gated in a time section corresponding to a time point t12. For example, the data acquirer 610 reconstructs a tomography image 1323 by using a sinogram gated in a time section corresponding to a time point t(n−2) and reconstructs a tomography image 1324 by using a sinogram gated in a time section corresponding to a time point t(n−1).

Referring to FIG. 13C, the data acquirer 610 generates an image which corresponds to a difference value 1343 by comparing two images 1341 and 1342, which correspond to two adjacent time points i and (i+1), with each other. Then, the data acquirer 610 generates a graph 1350 which depicts respective difference values as a function of time.

Referring to the graph 1350 of FIG. 13C, the X axis may represent time, and the Y axis may represent the difference values.

The data acquirer 610 may acquire two time sections 1361 and 1362, where the values of the Y axis are minimal, from the graph 1350, and select time points which respectively correspond to the two time sections 1361 and 1362 as the first time point t1 and the second time point t2. A smallest difference between two images corresponding to two adjacent time points means that motion of an object is the smallest between the two adjacent time points. Thus, the motion of the object is the smallest between the time sections 1361 and 1362 where the values of the Y axis are minimal. Accordingly, the data acquirer 610 may acquire a time section during which a motion of a heart is the most static and the most stable.

Figure 14A:
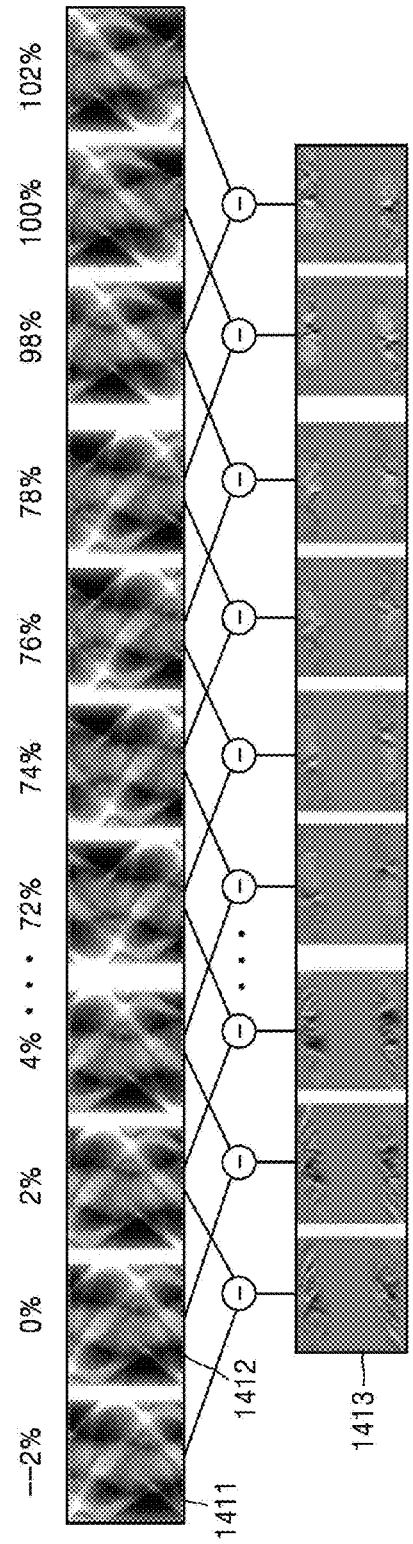
FIGS. 14A and 14B are schematic diagrams which illustrate an operation of the tomography apparatus of FIG. 6.
Figure 14B:
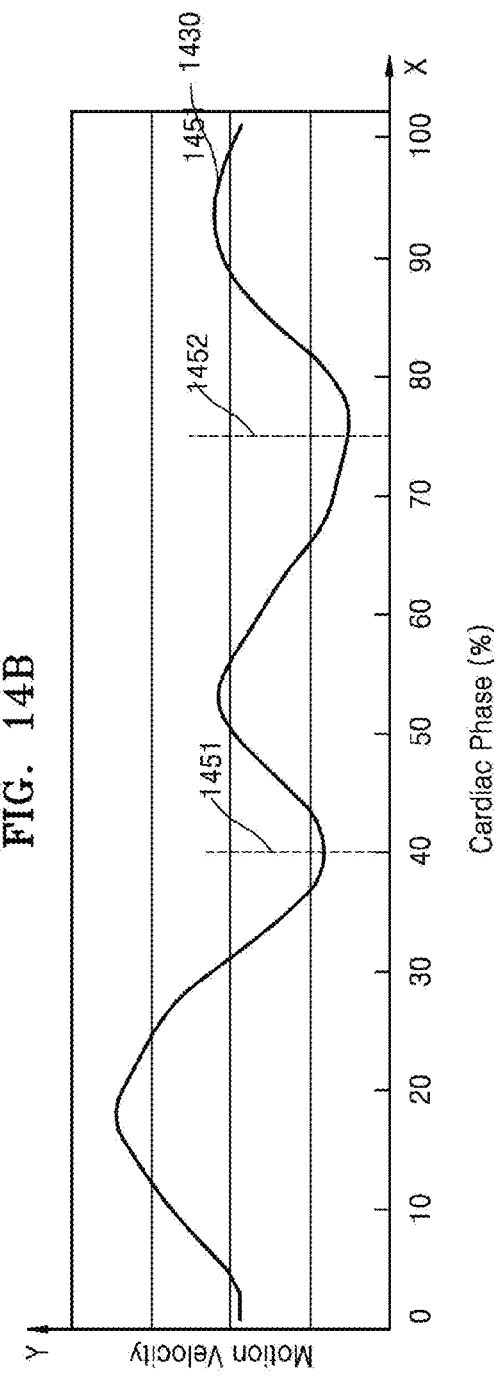

FIGS. 14A and 14B are schematic diagrams which illustrate an operation of the tomography apparatus 600, according to another exemplary embodiment.

Referring to FIG. 14A, the data acquirer 610 acquires projection data at intervals of a second time period within a predetermined time section, and measures a difference between projection data acquired in a time section corresponding to one time point and projection data acquired in a time section corresponding to another time point adjacent to the one time point. Then, the data acquirer 610 may select two time points when a motion of an object is minimized as a first time point and a second time point, based on the measured difference.

Referring to FIG. 14A, a cardiac phase representing one R-R cycle is expressed as 100% and is divided into 50 sections. Thus, one section is expressed as 2%.

The data acquirer 610 acquires projection data at intervals of 2%. Then, the data acquirer 610 measures a difference value 1413 between a sinogram 1411 obtained by accumulating pieces of projection data acquired in a time section corresponding to one time point and a sinogram 1412 obtained by accumulating pieces of projection data acquired in a time section corresponding to another time point adjacent to the one time point. For example, the sinogram 1411 may be a sinogram acquired during a time interval between −2% and 0%, and the sinogram 1412 may be a sinogram acquired during a time interval between 0% and 2%. Then, the data acquirer 610 generates a graph 1430 which depicts the respective difference values 1413.

Referring to the graph 1430 of FIG. 14B, the X axis represents the cardiac phase representing one R-R cycle, and the Y axis represents a value corresponding to the difference value 1413.

The data acquirer 610 may acquire two time points 1451 and 1452, when the values of the Y axis, which are difference values, are minimal, from the graph 1430 and select the two time points 1451 and 1452 as the first time point t1 and the second time point t2. Accordingly, the data acquirer 610 may acquire a time section during which motion of a heart is the most static and the most stable.

As illustrated in FIGS. 13A, 13B, 13C, 14A, and 14B, the first time point t1 and the second time point t2 when motion of an object is the smallest may be selected, and the time section between the first time point t1 and the second time point t2 may be set as the total time section 1260.

The image reconstructor 620 may compare data predicted by using first information at a third time point t3 other than the first and second time points t1 and t2 within the total time section 1260, with data which corresponds to the third time point t3, and correct the first information such that a difference between the two pieces of data decreases. In detail, the image reconstructor 620 may correct the first information at each of a plurality of time points that are apart from each other at regular or irregular intervals within the time section between the first and second time points t1 and t2.

In detail, the image reconstructor 620 may divide the time section between the first and second time points t1 and t2 by n, and may correct the first information at each of a plurality of time points that are apart from each other at intervals of a first time period that is a quotient of the division, starting from at least one of the first and second time points t1 and t2. In detail, the image reconstructor 620 may correct the first information at a third time point t3, which is a time point apart from the first time point t1 toward the second time point t2 by the first time period. The image reconstructor 620 may also correct the first information at a third time point t3, which is a time point apart from the second time point t2 toward the first time point t1 by the first time period.

For example, when the time section between the first time point t1 and the second time point t2 is divided by n, a time interval is (t2−t1)/n. Accordingly, the image reconstructor 620 may correct the first information at a time point (t1+(1/n)*(t2−t1)) apart from the first time point t1 by one time interval, and may also correct the first information at a time point (t1+(2/n)*(t2−t1)) apart from the time point (t1+(1/n)*(t2−t1)) by one time interval. As described above, the image reconstructor 620 may repeatedly correct the first information at each of a plurality of time points that are apart from each other at regular or irregular intervals within the time section between the first and second time points t1 and t2.

The image reconstructor 620 may correct the first information at a time point (t2−(1/n)*(t2−t1)) apart from the second time point t2 by one time interval, and may also correct the first information at a time point (t2−(2/n)*(t2−t1)) apart from the time point (t2−(1/n)*(t2−t1)) by one time interval. As described above, the image reconstructor 620 may repeatedly correct the first information at each of a plurality of time points that are apart from each other at regular or irregular intervals within the time section between the first and second time points t1 and t2.

The image reconstructor 620 may acquire second information by correcting the first information at the third time point t3, which is a time point apart from the first time point t1 toward the second time point t2, by the first time period. The image reconstructor 620 may acquire third information by correcting the first information at a third time point t3, which is a time point apart from the second time point t2 toward the first time point t1 by the first time period. The image reconstructor 620 may generate corrected first information, based on the first information and the second information. In detail, the image reconstructor 620 may generate the corrected first information by averaging the first information and the second information.

A case in which the image reconstructor 620 corrects the first information at the time point t3 within the time section between the first and second time points t1 and t2 will now be described.

Figure 15:
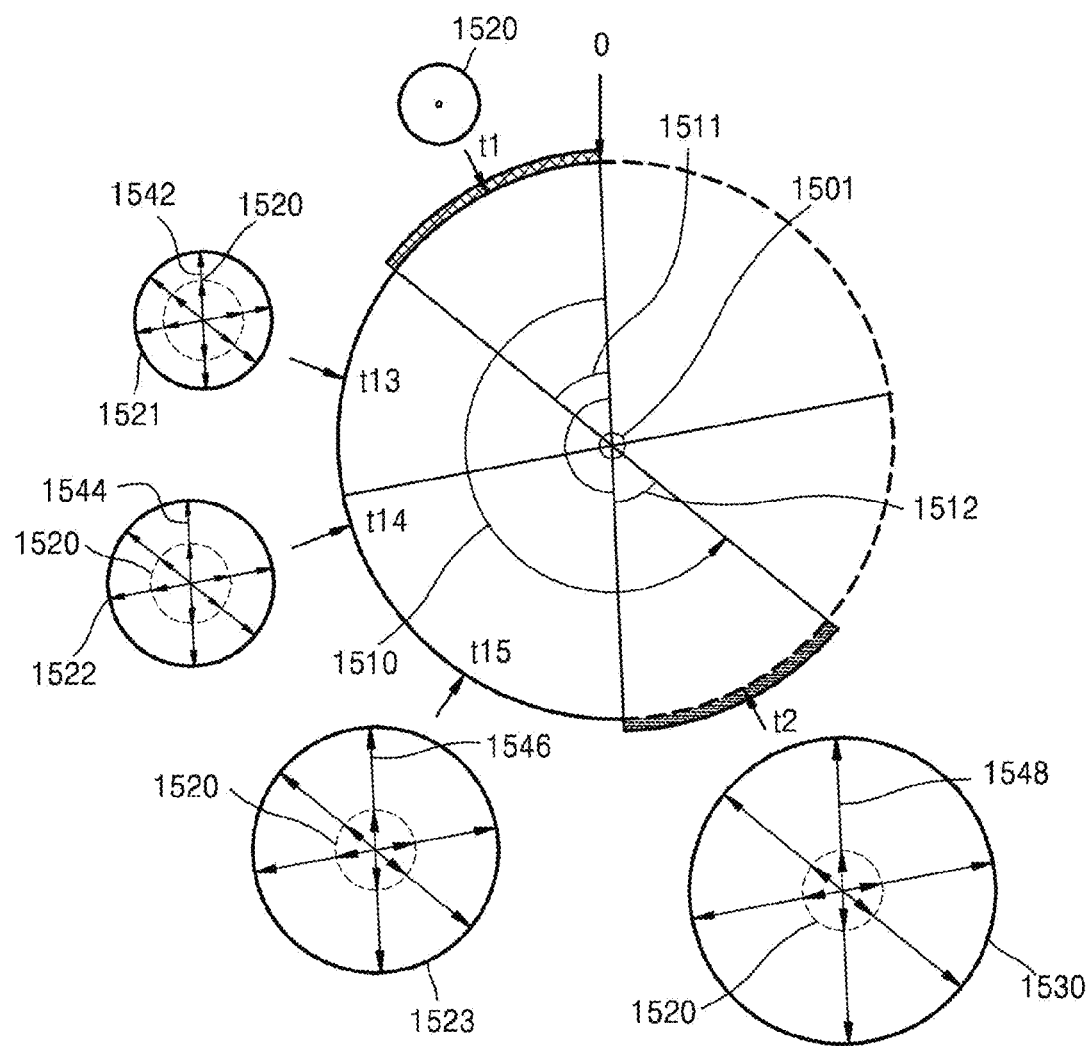
FIG. 15 is a view which illustrates a motion change of an object.

FIG. 15 is a view which illustrates a motion change of the object.

An object 1501 of FIG. 15 may identically correspond to any one of the objects (e.g., 1211) illustrated in FIG. 12A.

When an object included in a first image which corresponds to a first time point t1 and an object included in a second image which corresponds to a second time point t2 are compared with each other, and thus a motion amount of the object and the first information are acquired, a change in the size of the object in a total time section 1510 may be predicted by using the first information.

Referring to FIG. 15, the object included in the first image which corresponds to the first time point t1 may have a first size 1520, and the object included in the second image which corresponds to the second time point t2 may have a second size 1530.

For example, when a weighting value which corresponds to a motion amount of the object and the time amount in the first information are in a linear relationship as illustrated in FIG. 12C, the size of the object 1501 linearly increases.

Accordingly, as illustrated in FIG. 15, it may be expected that the size of the object at a third time point t13 is changed by a first change amount 1542 to be larger than the first size 1520. Accordingly, it may be expected that the size of the object at the third time point t13 may have a third size 1521.

It may also be expected that the size of the object 1501 at a fourth time point t14 is changed by a second change amount 1544 to be larger than the first size 1520. Accordingly, it may be expected that the size of the object 1501 at the fourth time point t14 may have a fourth size 1522. It may also be expected that the size of the object 1501 at a fifth time point t15 is changed by a third change amount 1546 to be larger than the first size 1520. Accordingly, it may be expected that the size of the object 1501 at the fifth time point t15 may have a fifth size 1523.

The size of the object 1501 at the third time point t13, the fourth time point t14, and the fifth time point t15 may be predicted by contracting the object having the second size 1530 based on the first information.

In particular, a size change amount at the third time point t13 may be predicted by using the first information, and an image of the object at the third time point t13 may be acquired based on the predicted size change amount. In detail, the image reconstructor 620 may acquire a predicted image by warping at least one selected from among the first image, the second image, and raw data corresponding to the third time point t13 based on the first information. The warping signifies an adjustment of the size of the object included in the image to fit to an expected size of the object via expanding or contracting of the object included in the image.

In detail, referring to FIG. 12C, a weighting value W1 which corresponds to the third time point t3 in the first information 1280 is used to predict an image at the third time point t3 in the total time section 1260. The weighting value W1 which corresponds to the third time point t3 is acquired from the first information 1280, and the first image may be warped using a motion amount which corresponds to the weighting value W1, or the second image may be warped using a motion amount which corresponds to a weighting value (1−W1). The image which corresponds to the third time point t3 may be predicted by using at least one selected from among a warped first image and a warped second image. Alternatively, a predicted third image may be acquired by warping the raw data which corresponds to the third time point t13, based on the first information.

A predicted image predicted at the third time point t3 by using the first information is hereinafter referred to as a predicted third image. The above-described predicted data which corresponds to the third time point may be the predicted third image or projection data or a sinogram which corresponds to the predicted third image.

The image reconstructor 620 corrects the first information by using the predicted third image and measured data that is acquired at the third time point t3. The measured data denotes actually measured projection data or an actually measured sinogram, or an image reconstructed by back-projecting the actually measured projection data or the actually measured sinogram. The correction of the first information by the image reconstructor 620 will now be described in detail with reference to FIGS. 16 and 17.

Figure 16:
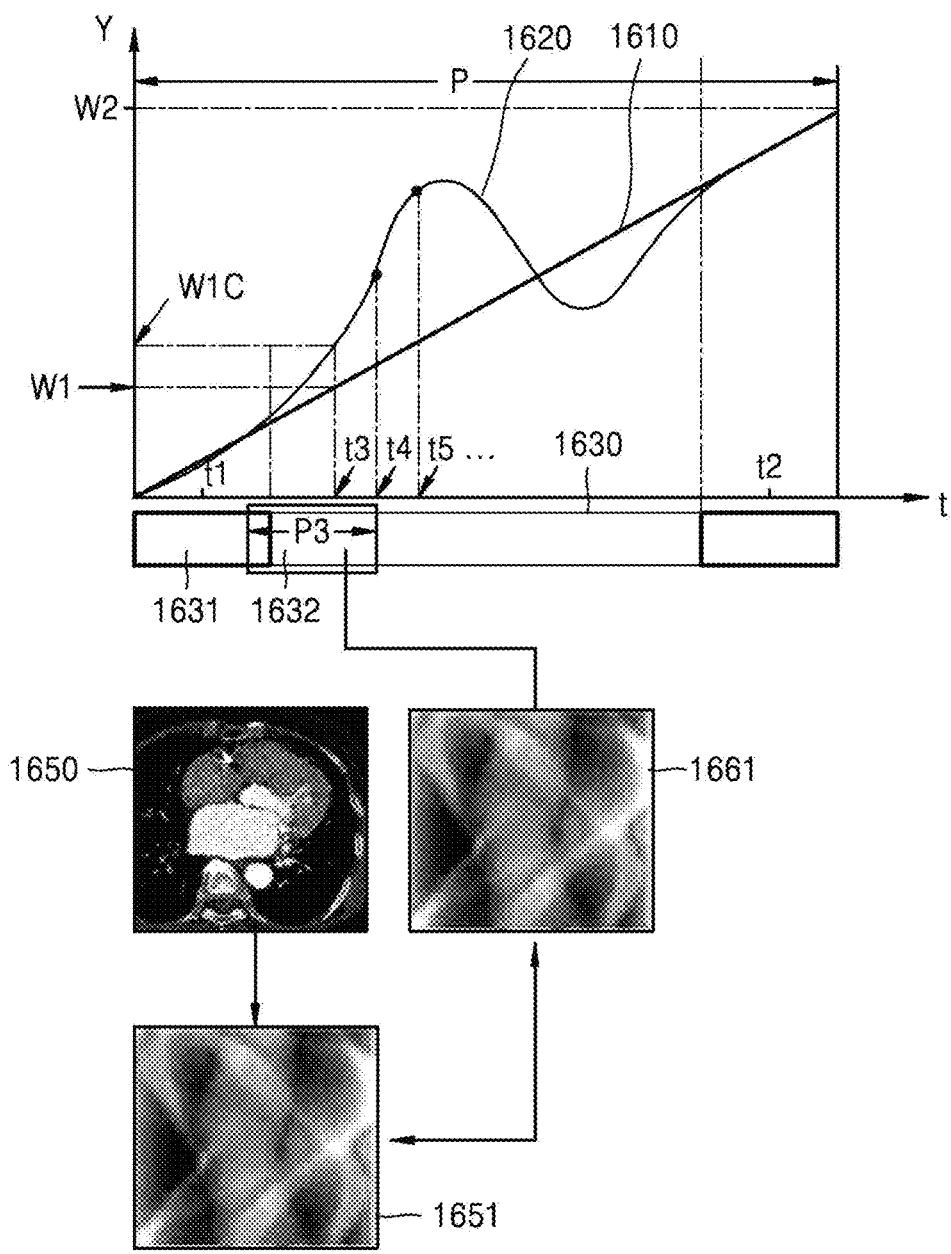
FIG. 16 is a view which illustrates a correction of first information.

FIG. 16 is a view which illustrates a correction of first information.

Referring to FIG. 16, a graph 1610 represents first information before correction, and a graph 1620 represents first information after correction. FIG. 16 illustrates a sinogram 1630 acquired according to the time in a total time section P. The sinogram 1630 is acquired via a tomography scan during the total time section P. In particular, the sinogram 1630 refers to data acquired by converting sensed X-rays during the tomography scan, and thus represents a measured data value. The sinogram 1630 may be acquired by performing a tomography scan during the total time section P in a retrospective mode. The sinogram 1630 may also be acquired by performing a tomography scan according to a helical scanning method.

A sinogram necessary for reconstructing an image which corresponds to the third time point t3 is a sinogram 1632 acquired during a time section which corresponds to the third time point t3 and may be displayed as an image 1661. For example, when projection data is acquired using a rebinned parallel beam, to reconstruct an image which corresponds to the third time point t3, a sinogram acquired in a time section P3 which corresponds to an angular section having an angle of 180°+additional angle by including the third time point t3 is needed.

The image reconstructor 620 may compare a predicted sinogram 1651 acquired by forward projecting a predicted third image 1650 acquired using the first information with the measured sinogram 1661 acquired at the third time point t3 and may correct the first information such that a difference between the predicted sinogram 1651 and the measured sinogram 1661 decreases. In detail, the image reconstructor 620 may correct the first information so that the predicted sinogram 1651 has the same value as the measured sinogram 1661.

For example, if a difference between the measured sinograms 1632 and 1661 and the predicted sinogram 1651 decreases when the Y axis value at the third time point t3 in the first information 1610 before correction increases, a weighting value at the third time point t3 in the first information 1610 may be increased from W1 to W1C.

Similarly, the image reconstructor 620 may correct a weighting value of the first information 1610 at a fourth time point t4 that elapsed from the third time point t3 by a predetermined time interval, and may correct a weighting value of the first information 1610 at a fifth time point t5 that elapsed from the fourth time point t4 by the predetermined time interval.

As described above, when a predicted sinogram and a measured sinogram at a predetermined time point are compared and first information is corrected based on a difference between the predicted sinogram and the measured sinogram, corrected first information 1620 may be obtained by correcting first information within the total time section P. The corrected first information 1620 more accurately reflects the motion pattern of the object. Thus, when motion correction is performed based on the corrected first information 1620 in order to accurately reflect a state of the object at the third time point t3, the image which corresponds to the third time point t3 may be accurately reconstructed. In detail, when the image which corresponds to the third time point t3 is accurately reconstructed by warping raw data acquired to reconstruct the image which corresponds to the third time point t3 or an image acquired by back-projecting the acquired raw data, an image which corresponds to a predetermined time point may be easily and accurately reconstructed.

Figure 17:
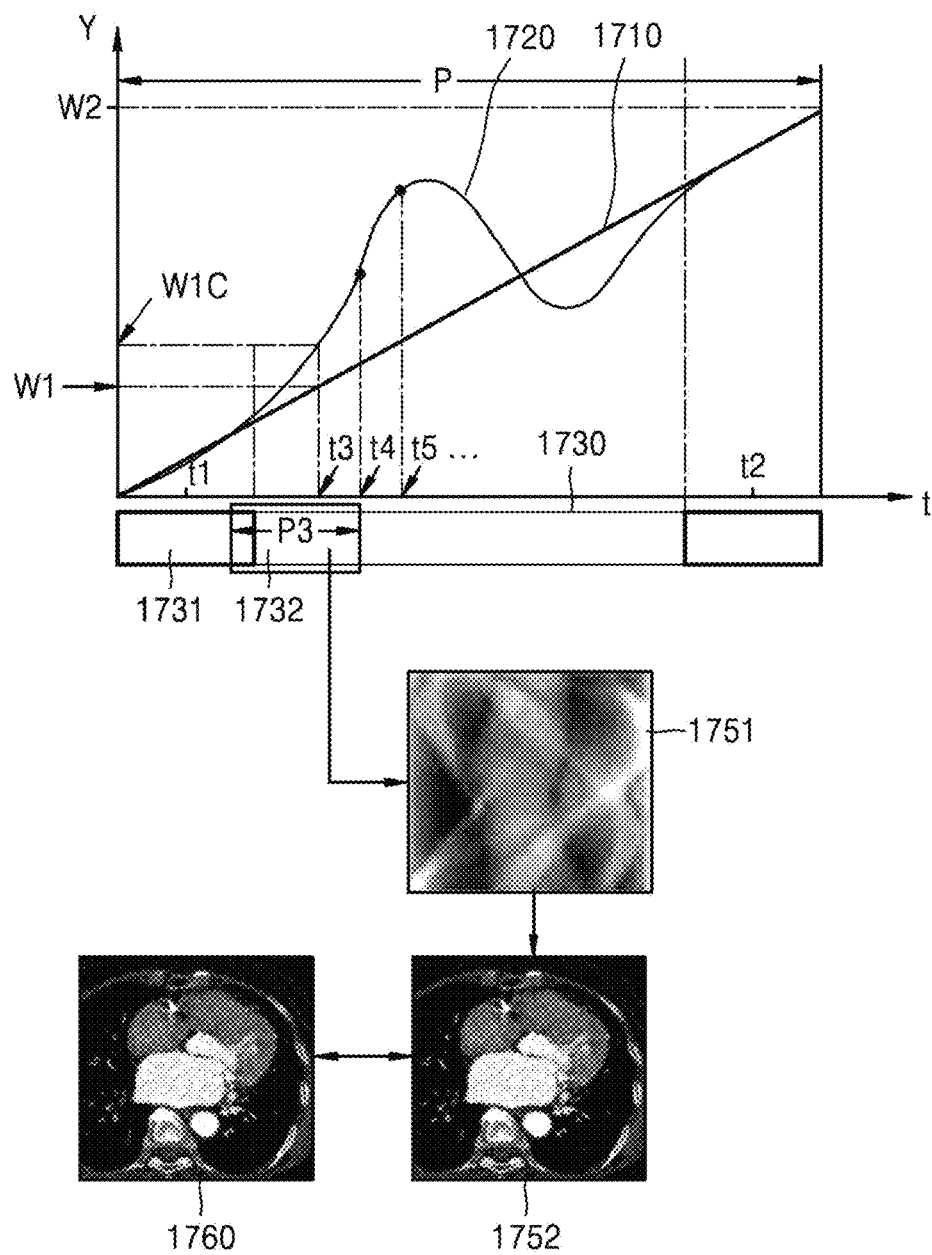
FIG. 17 is a view which illustrates a correction of first information.

FIG. 17 is a view which illustrates a correction of first information.

The image reconstructor 620 may compare a measured image obtained by back-projecting measured data acquired at a third time point t3 with a predicted image, and correct the first information such that a difference between the measured image and the predicted image decreases.

Referring to FIG. 17, a graph 1710 represents first information before correction, and a graph 1720 represents first information after correction. FIG. 17 illustrates a sinogram 1730 acquired in a total time section P. The sinogram 1730 is acquired via a tomography scan during the total time section P. In particular, the sinogram 1730 is a data value measured via a tomography scan. A sinogram necessary for reconstructing an image which corresponds to the third time point t3 may be displayed as an image 1751.

Referring to FIG. 17, the image reconstructor 620 compares a measured image 1752 produced by back projecting the sinogram 1751 acquired during the time period P3 which corresponds to the third time point t3 with a predicted image 1760 produced by warping at least one of first and second images by using the first information 1710 before correction. The image reconstructor 620 may correct the first information such that a difference between the measured image 1752 and the predicted image 1760 decreases.

For example, if the difference between the measured image 1752 and the predicted image 17601 decreases when the Y axis value at the third time point t3 in the first information 1710 before correction increases, a weighting value at the third time point t3 in the first information 1710 may be increased from W1 to W1C.

Similarly, the image reconstructor 620 may correct a weighting value of the first information 1710 at a fourth time point t4 that elapsed from the third time point t3 by a predetermined time interval and may correct a weighting value of the first information 1710 at a fifth time point t5 that elapsed from the fourth time point t4 by the predetermined time interval.

The third time point t3, which corresponds to a third image that is to be reconstructed using corrected first information, may be a time point elapsed by a predetermined time interval from at least one of the first and second time points t1 and t2 as described above with reference to FIGS. 16 and 17. The third time point t3 may be set via the user interface 650. In detail, the display 630 may display a UI image (not shown) which relates to selecting the third time point t3 from the time section between the first time point t1 and the second time point t2. Then, a user may select the third time point t3 via the user interface 650.

As described above, the corrected first information 1720 more accurately reflects the motion pattern of the object. Thus, similarly as illustrated in FIG. 16, when motion correction is performed based on the corrected first information 1720 to accurately reflect a state of the object at the third time point t3, the image which corresponds to the third time point t3 may be accurately reconstructed.

Figure 18:
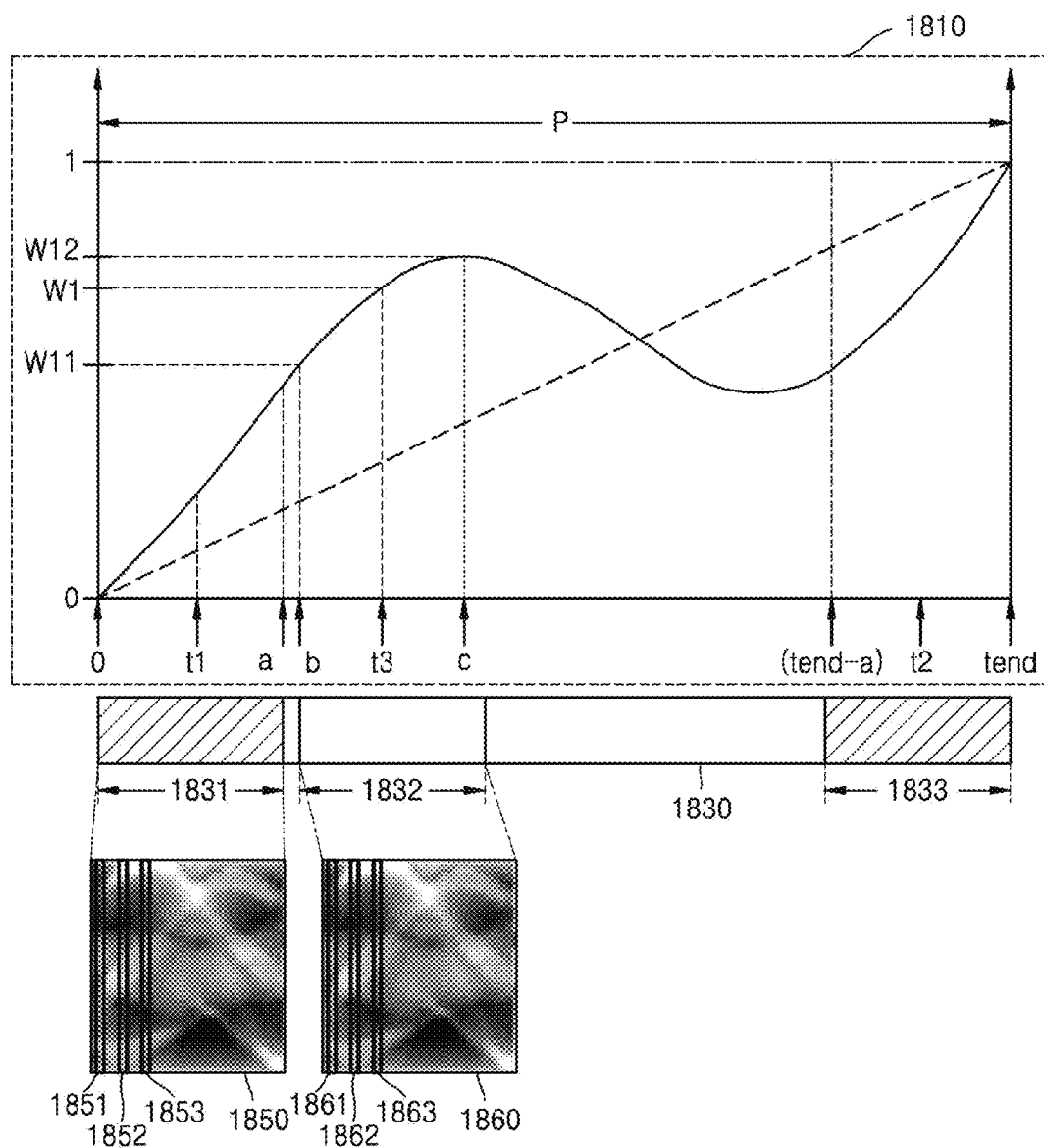
FIG. 18 is a schematic diagram which illustrates a tomography image reconstruction that is performed by the tomography apparatus of FIG. 6, according to an exemplary embodiment.

FIG. 18 is a schematic diagram which illustrates a tomography image reconstruction that is performed by the tomography apparatus 600, according to an exemplary embodiment.

Referring to FIG. 18, corrected first information 1810 and raw data 1830 that is acquired in the total time section P are illustrated. The raw data 1830 may include a collection of a plurality of pieces of projection data acquired in correspondence to a plurality of consecutive views. The raw data 1830 may include a sinogram obtained in the total time section P. Since the corrected first information 1810 identically corresponds to the first information of FIG. 12C and the first information 1620 and 1720 described above with reference to FIGS. 16 and 17, repeated descriptions thereof will be omitted.

Referring to FIG. 18, the image reconstructor 620 may reconstruct a tomography image which corresponds to a predetermined time point included in the total time section P, based on the corrected first information 1810 representing a motion amount of the object within the total time section P.

A case in which the image reconstructor 620 performs image reconstruction according to the half reconstruction method and the image reconstruction is performed using a rebinned parallel beam will now be described. Accordingly, a case in which one tomography image is acquired using raw data acquired in an angular section having an angle of 180°+a(=fan angle) will now be described.

In detail, in order to reconstruct a tomography image of an object at a first time point t1, raw data 1831 that corresponds to the first time point t1 and is acquired in the angular section having an angle of 180°+a(=fan angle) is needed. The raw data 1831 may include a sinogram 1850 acquired a time section from 0 to a in correspondence with the angular section having an angle of 180°+a(=fan angle). The sinogram 1850 may be formed of a plurality of projection data 1851, 1852, and 1853 in correspondence with a plurality of consecutive views. In order to reconstruct a tomography image of the object at a third time point t3, raw data 1832 that corresponds to the third time point t3 and is acquired in a time section between time points b and c that corresponds to the angular section having an angle of 180°+a(=fan angle) is needed. The raw data 1832 may include a sinogram 1860 acquired in the angular section having an angle of 180°+a (=fan angle). The sinogram 1860 may be formed of a plurality of projection data 1861, 1862, and 1863 in correspondence with a plurality of consecutive views.

In detail, in order to reconstruct a final third image which corresponds to the third time point t3, the tomography image which corresponds to the third time point t3 may be reconstructed by back-projecting the sinogram 1860, which is measured data, and the reconstructed tomography image may be warped based on corrected first information. Warping is performed to correct motion of a moving object, and the warping will now be described in more detail with reference to FIGS. 19A through 24.

Figure 19B:
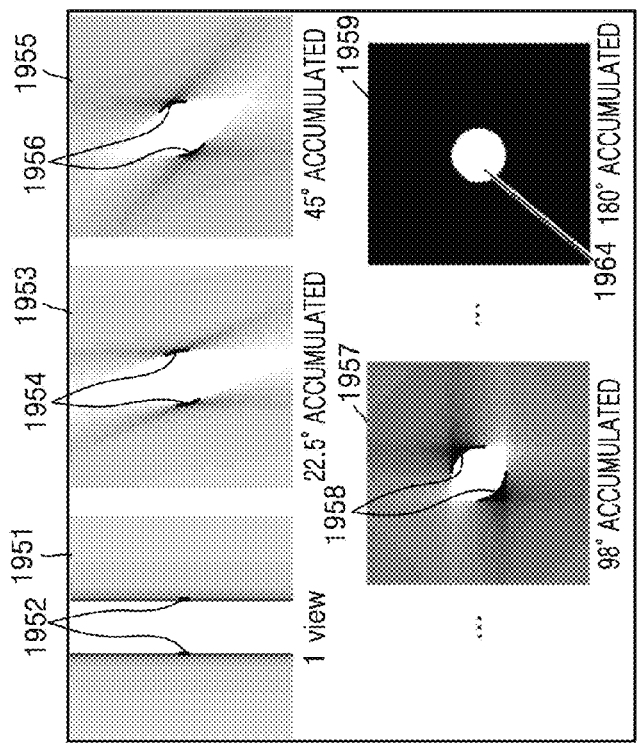
FIGS. 19A and 19B are views which illustrate tomography image reconstruction according to a half reconstruction method, for a non-moving object.
Figure 19A:
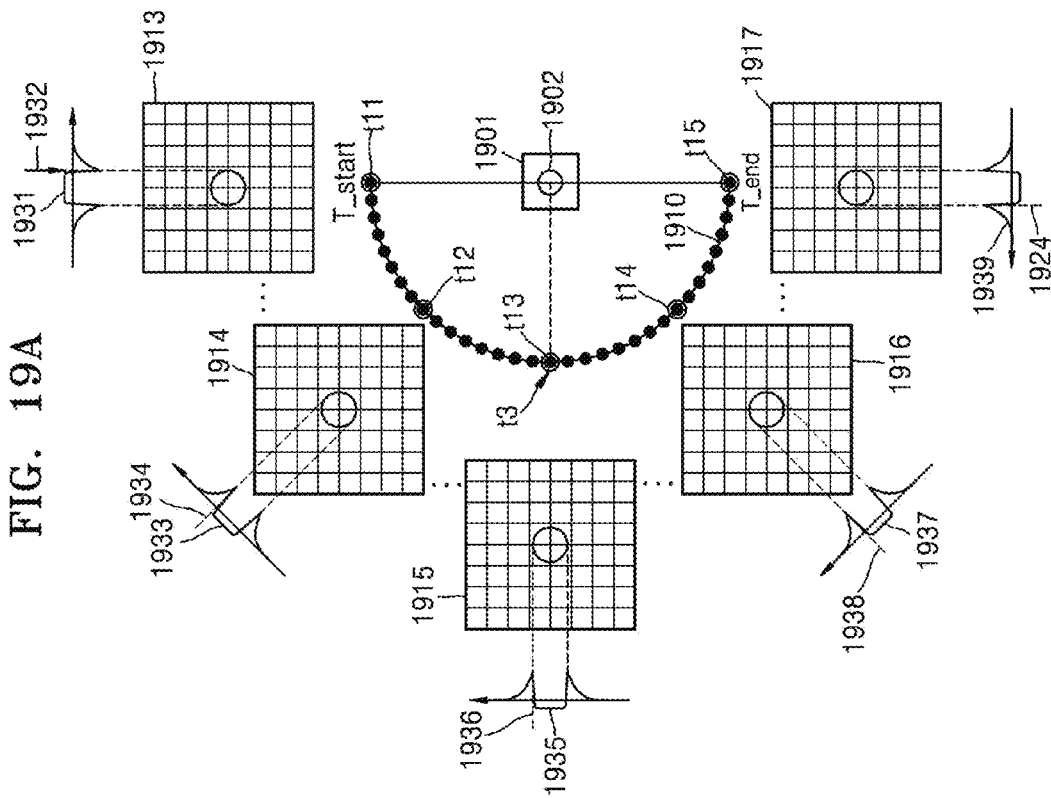

FIGS. 19A and 19B are views which illustrate a tomography image reconstruction according to the half reconstruction method, according to an exemplary embodiment. FIG. 19A is a view which illustrates a reconstruction of a target image which indicates an object that does not move. In detail, FIG. 19A illustrates that the X-ray generator 106 performs a tomography scan while rotating around an object 1901. FIG. 19B illustrates an operation of performing back-projection on pieces of projection data acquired by filtering raw data acquired via a tomography scan.

In FIGS. 19A and 19B, a case in which the X-ray generator 106 rotates around the object 1901 and performs a tomography scan and a tomography image is reconstructed by a filtered back-projection method is described as an example. Further, a case in which the object 1901 includes a circular target 1902 as illustrated in FIG. 19A is described as an example. A one-cycle angular section necessary for reconstructing one tomography image according to the half reconstruction method is an angle of 180°+fan angle that is a section of projection data. However, in FIG. 19A, a case in which a tomography scan is performed using raw data acquired while rotating 180° is described as an example, for convenience of explanation.

Referring to FIG. 19A, as the X-ray generator 106 projects X-rays toward the object 1901 at each of a plurality of positions having a predetermined angular interval while moving along a source trajectory 1910 that is circular, projection data is acquired. The projection data is filtered, and thus filtered projection data is acquired. In FIG. 19A, a plurality of points located on the source trajectory 1910 indicate the positions where the X-ray generator 106 is located to project X-rays. For example, while moving at a predetermined angular interval such as 0.5°, 1°, or 3°, the X-ray generator 106 may project X-rays toward the object 1901. Rotation starts at a time point t11 and stops at a time point t15. Accordingly, the time point t11 corresponds to a rotation angle 0° and the time point t15 corresponds to a rotation angle 180°.

Pieces of projection data acquired by rotating from the time point t11 to the time point t15 may correspond to the raw data 1831, 1832, or 1833 described above with reference to FIG. 18, which are necessary for reconstructing one cross-sectional tomography image.

In detail, when the X-ray generator 106 projects X-ray toward the object 1901 at the time point t11, the X-rays projected in an X-ray projection direction 1932 propagate through an object 1913, and thus a signal 1931 may be acquired. A value of the signal 1931 may vary on a surface of the object 1913 due to a difference in transmissivity of the X-ray according to a material of the object 1913. In detail, the value of the signal 1931 may vary on a surface arranged in a direction parallel to the X-ray projection direction 1932.

When the X-ray generator 106 projects X-rays toward the object 1901 at the time point t12, the X-rays projected in an X-ray projection direction 1934 propagate through an object 1914, and thus a signal 1933 may be acquired. The value of the signal 1933 may vary on a surface arranged in a direction parallel to the X-ray projection direction 1934.

When the X-ray generator 106 projects X-rays toward the object 1901 at the time point t13, the X-rays projected in an X-ray projection direction 1936 propagate through an object 1915, and thus a signal 1935 may be acquired. The value of the signal 1935 may vary on a surface arranged in a direction parallel to the X-ray projection direction 1936.

When the X-ray generator 106 projects X-rays toward the object 1901 at the time point t14, the X-rays projected in an X-ray projection direction 1938 propagate through an object 1916 and thus a signal 1937 may be acquired. The value of the signal 1937 may vary on a surface arranged in a direction parallel to the X-ray projection direction 1938.

When the X-ray generator 106 projects X-rays toward the object 1901 at the time point t15, the X-rays projected in an X-ray projection direction 1924 propagate through an object 1917 and thus a signal 1939 may be acquired. The value of the signal 1939 may vary on a surface arranged in a direction parallel to the X-ray projection direction 1924.

Since the signal 1931 includes information about the surface that is arranged in the X-ray projection direction 1932, an image 1951 acquired by performing filtered back-projection on the signal 1931 contributes to imaging of the surface arranged in the X-ray projection direction 1932. Since the signal 1933 includes information about the surface that is arranged in the X-ray projection direction 1934, projection data which corresponds to the signal 1933 contributes to imaging of the surface arranged in the X-ray projection direction 1934. In particular, the projection data acquired at each view contributes to imaging of a surface of the object in correspondence with each view. This may be explained by using a Fourier slice theorem that shows a relationship between a frequency component of an image and a value of the projection data acquired by projection a parallel beam toward the object 1901. The "view" corresponds to a direction, position, and/or rotation angle when the X-ray generator 106 projects X-rays toward the object.

The DAS 116 of FIG. 3 may acquire a signal, for example, the signal 1931. The image processing unit 126 of FIG. 3 may process the signal 1931 and generate filtered projection data. The filtered projection data is back-projected, thereby acquiring the image 1951.

In detail, when the X-ray generator 106 rotates and projects X-rays at a plurality of positions or views and thus a plurality of pieces of filtered projection data are acquired, the pieces of filtered projection data are accumulated and back-projected, thereby reconstructing a tomography image. In particular, an image which represents the object may be acquired via a back-projection process in which the filtered projection data is reflected to image pixels.

Referring to FIG. 19B, a surface of the circular target 1902 included in the object 1901 at the time point t11 appears in the back-projected image 1951 which corresponds to the time point t11. The pieces of filtered projection data are accumulated and back-projected with respect to the respective views acquired as the X-ray generator 106 rotates in a counterclockwise direction.

For example, a back-projected image 1953 is acquired by accumulating and back-projecting the pieces of filtered projection data acquired in an angular section having an angle of 22.5°. A partial surface 1954 of the circular target 1902 in the object 1901 appears in the back-projected image 1953.

Next, a back-projected image 1955 is acquired by accumulating and back-projecting the pieces of filtered projection data acquired in an angular section having an angle of 45°. A partial surface 1956 of the circular target 1902 in the object 1901 appears in the back-projected image 1955.

Next, a back-projected image 1957 is acquired by accumulating and back-projecting the pieces of filtered projection data acquired in an angular section having an angle of 98°. A partial surface 1958 of the circular target 1902 in the object 1901 appears in the back-projected image 1957.

Next, a back-projected image 1959 is acquired by accumulating and back-projecting the pieces of filtered projection data acquired in an angular section having an angle of 180°. An entire surface 1964 of the circular target 1902 in the object 1901 appears in the back-projected image 1959.

For an object that does not move, a state, for example, at least one of the size, position, and shape, of the object 1901 is unchanged when referring to each of the time points t11, t12, t13, t14, and t15, which are a plurality of time points included in the one-cycle angular section.

Accordingly, in the reconstruction of a tomography image by accumulating the pieces of filtered back-projected data of the pieces of projection data which respectively correspond to the plurality of views included in the one-cycle angular section, since the respective states of the object 1901 at the plurality of views are the same as one another, no blurring due to motion artifacts is generated in the back-projected image 1959 that is finally reconstructed.

Figure 20B:
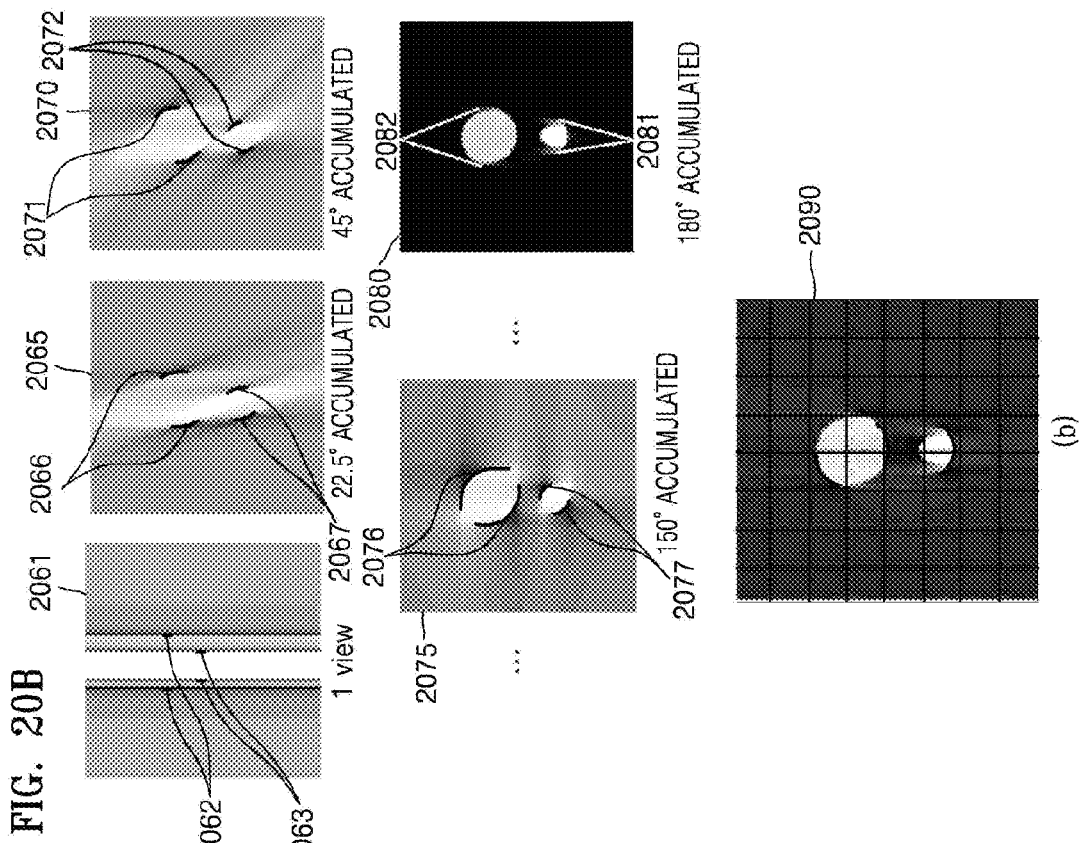
FIGS. 20A and 20B are views which illustrate tomography image reconstruction according to the half reconstruction method, for a moving object.
Figure 20A:
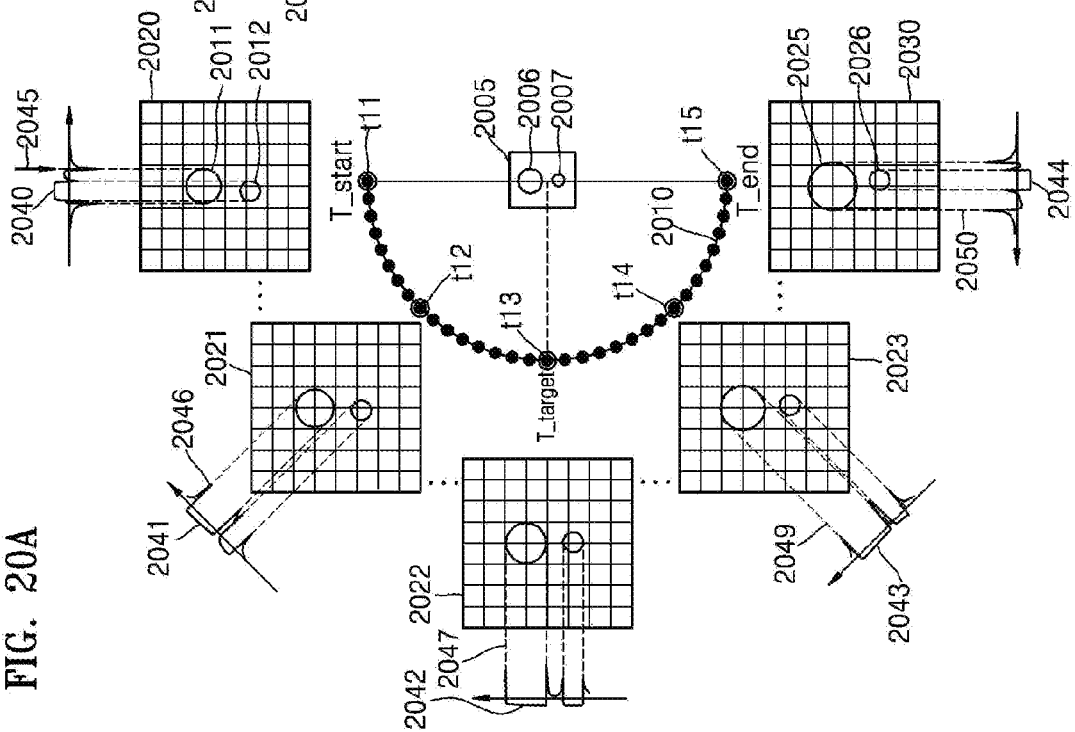

FIGS. 20A and 20B are views which illustrate a tomography image reconstruction according to the half reconstruction method, according to another exemplary embodiment. In detail, FIG. 20A illustrates that the X-ray generator 106 performs a tomography scan while rotating around an object 2005. FIG. 20B illustrates an operation of performing back-projection on pieces of projection data acquired by filtering raw data acquired via a tomography scan. In FIG. 20B, a case of reconstructing a tomography image by using a filtered back projection method is described as an example. Further, a case in which the object 2005 includes two circular targets 2006 and 2007 as illustrated in FIG. 20A is described as an example. In the following description, for convenience of explanation, an upper circular target 2006 of the object 2005 is referred to as a first target 2006 and a lower circular target 2007 of the object 2005 is referred to as a second target 2007. As described above, a one-cycle angular section in half reconstruction is an angle of 180+fan angle. However, in FIG. 20A, for convenience of explanation, a case of performing a tomography scan while rotating by 180° is described as an example.

Referring to FIG. 20A, as the X-ray generator 106 projects X-rays toward the object 2005 at each of a plurality of positions having a predetermined angular interval while moving along a source trajectory 2010 that is circular, projection data is acquired. The projection data is filtered, and thus filtered projection data is acquired. In FIG. 20A, a plurality of points located on the source trajectory 2010 indicate the positions where the X-ray generator 106 is located to project X-rays. For example, while moving at a predetermined angular interval such as 0.5°, 1°, or 3°, the X-ray generator 106 may project X-rays toward the object 2005. Rotation starts at a time point t11 and stops at a time point t15. Accordingly, the time point t11 corresponds to a rotation angle 0° and the time point t15 corresponds to a rotation angle 180°.

The object 2005 may move like an object 2020, an object 2021, an object 2022, an object 2023, and object 2030, respectively, at the time point t11, the time point t12, the time point t13, the time point t14, and the time point t15. In detail, the size of the first target 2006 included in the object 2005 expands without changing its position, whereas the second target 2007 does not expand but may move from the left to the right.

In detail, when the X-ray generator 106 projects X-rays toward the object 2005 at the time point t11, the X-rays projected in an X-ray projection direction 2045 propagate through the object 2020, and thus a signal 2040 may be acquired. A value of the signal 2040 may vary on a surface of the object 2020 due to a difference in transmissivity of the X-ray according to a material of the object 2020. In detail, the value of the signal 2040 may vary on a surface arranged in a direction parallel to the X-ray projection direction 2045.

When the X-ray generator 106 projects X-rays toward the object 2005 at the time point t12, the X-rays projected in an X-ray projection direction 2046 propagate through the object 2021, and thus a signal 2041 may be acquired. The value of the signal 2041 may vary on a surface arranged in a direction parallel to the X-ray projection direction 2046.

When the X-ray generator 106 projects X-rays toward the object 2005 at the time point t13, the X-rays projected in an X-ray projection direction 2047 propagate through the object 2022, and thus a signal 2042 may be acquired. The value of the signal 2042 may vary on a surface arranged in a direction parallel to the X-ray projection direction 2047.

When the X-ray generator 106 projects X-rays toward the object 2005 at the time point t14, the X-rays projected in an X-ray projection direction 2049 propagate through the object 2023, and thus a signal 2043 may be acquired. The value of the signal 2043 may vary on a surface arranged in a direction parallel to the X-ray projection direction 2049.

When the X-ray generator 106 projects X-rays toward the object 2005 at the time point t15, the X-rays projected in an X-ray projection direction 2050 propagate through the object 2030, and thus a signal 2044 may be acquired. The value of the signal 2044 may vary on a surface arranged in a direction parallel to the X-ray projection direction 2050.

Since the signal 2040 includes information about the surface that is arranged in the X-ray projection direction 2045, an image 2061 acquired by performing filtered back-projection on the signal 2040 contributes to imaging of the surface arranged in the X-ray projection direction 2045. Since the signal 2041 includes information about the surface that is arranged in the X-ray projection direction 2046, projection data which corresponds to the signal 2041 contributes to imaging of the surface arranged in the X-ray projection direction 2046. In particular, the projection data acquired at each view contributes to imaging of a surface of the object in correspondence with each view. The "view" corresponds to a direction, position, and/or rotation angle when the X-ray generator 106 projects X-rays toward the object.

The DAS 116 of FIG. 3 may acquire a signal, for example, the signal 2040. The image processing unit 126 of FIG. 3 may process the signal 2040 and generate filtered projection data. The filtered projection data is back-projected, thereby acquiring the image 2061.

In detail, when the X-ray generator 106 rotates and projects X-rays at a plurality of positions or views and thus a plurality of pieces of filtered projection data are acquired, the pieces of filtered projection data are accumulated and back-projected, thereby reconstructing a tomography image. In particular, an image which represents the object may be acquired through a back-projection process in which the filtered projection data is reflected to image pixels.

Referring to FIG. 20B, a surface 2062 of the first target 2006 and a surface 2063 of the second target 2007 at the time point t11 appear in the back-projected image 2061 which corresponds to the time point t11. The pieces of filtered projection data are accumulated and back-projected with respect to the respective views acquired as the X-ray generator 106 rotates counterclockwise.

For example, a back-projected image 2065 is acquired by accumulating and back-projecting the pieces of filtered projection data acquired in an angular section having an angle of 22.5°. A partial surface 2066 of the first target 2006 and a partial surface 2067 of the second target 2007 appear in the back-projected image 2065.

Next, a back-projected image 2070 is acquired by accumulating and back-projecting the pieces of filtered projection data acquired in an angular section having an angle of 45°. A partial surface 2071 of the first target 2006 and a partial surface 2072 of the second target 2007 appear in the back-projected image 2070.

Next, a back-projected image 2075 is acquired by accumulating and back-projecting the pieces of filtered projection data acquired in an angular section having an angle of 150°. A partial surface 2076 of the first target 2006 and a partial surface 2077 of the second target 2007 appear in the back-projected image 2075.

Next, a back-projected image 2080 is acquired by accumulating and back-projecting the pieces of filtered projection data acquired in an angular section having an angle of 180°. An entire surface 2082 of the first target 2006 and an entire surface 2081 of the second target 2007 appear in the back-projected image 2080.

In FIG. 20B, an image 2090 is a tomography image which shows a finally reconstructed object as a results of the back-projection process.

However, due to motion of the object, pieces of surface information of the pieces of filtered projection data acquired at each view do not match with one another. Accordingly, when a plurality of pieces of filtered projection data acquired in the one-cycle angular section are accumulated, as illustrated in FIG. 20B, the surface does not clearly appear and thus blurrings 2081 and 2082 are generated.

According to one or more exemplary embodiments, even when the object includes various materials, surfaces, and/or shapes as in the object 2005 of FIGS. 20A and 20B, motion of the object 2005 may be traced and the motion of the object 2005 may be accurately estimated without limiting the object which is to be tomography scanned. Accordingly, an image that is motion corrected according thereto may be reconstructed. Reconstruction of a final third image by using corrected first information will now be described in detail with reference to FIGS. 21, 22, 23, and 24.

Figure 21:
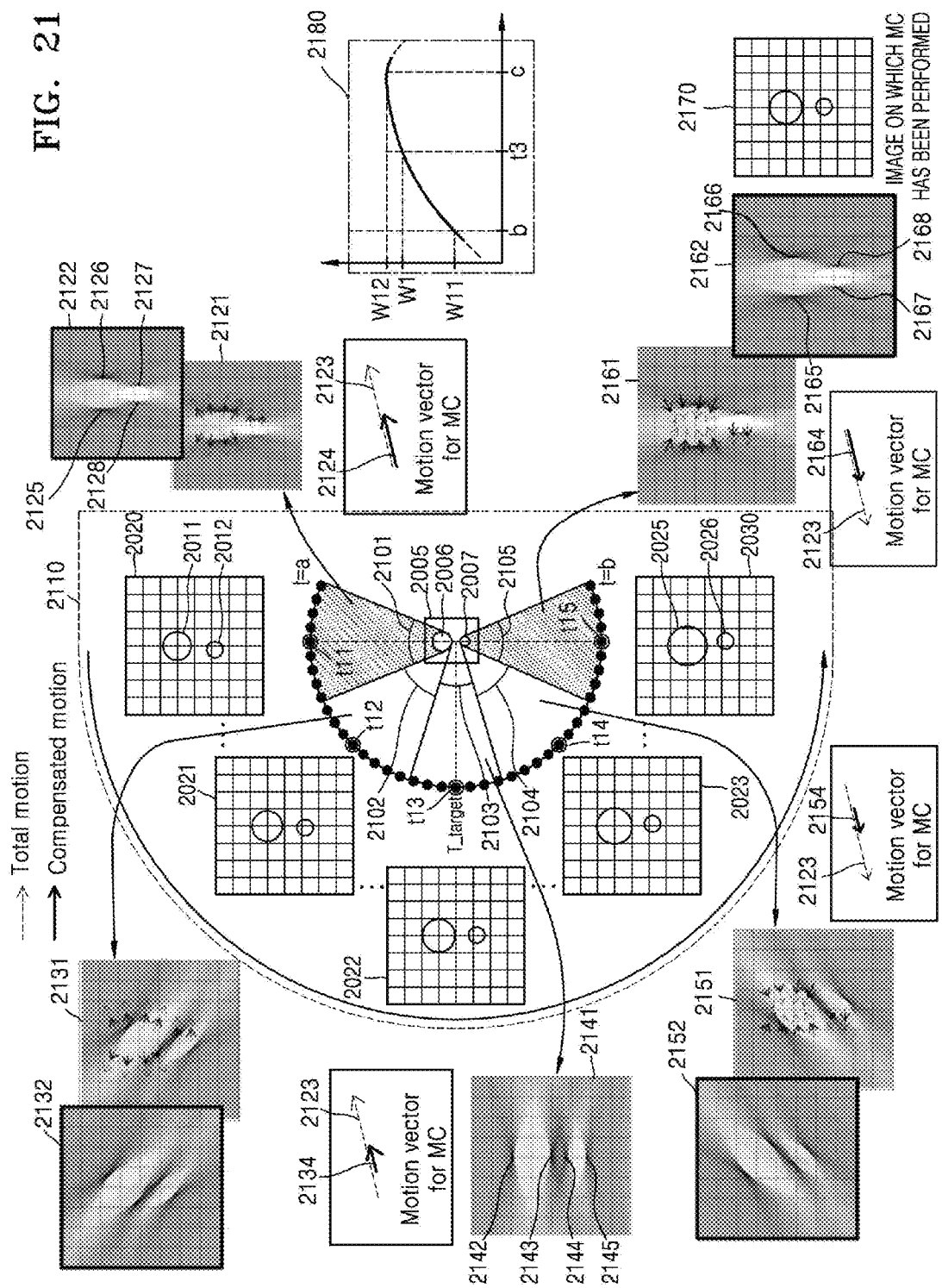
FIG. 21 is a view which illustrates the operation of reconstructing a motion-corrected tomography image.

FIG. 21 is a view which illustrates the operation of reconstructing a motion-corrected tomography image.

The image reconstructor 620 reconstructs an image of an object at a target time point T_target by using information which indicates motion of the object, for example, the MVF.

The target time point T_target is a time point when image reconstruction is desired to be performed. In FIG. 18, a target time point T_target of a third image that is desired to be reconstructed by using the raw data 1832 is the third time point t3.

An operation of generating a final third time point which is a motion-corrected image obtained by correcting motion of a third image by using corrected first information 2180 will now be described in detail. In FIG. 21, a case in which the target time point T_target is the third time point t3 and a final third image of an object that is an image at the third time point t3 is reconstructed will be described as an example. In FIGS. 18 and 21, the third time point t3, which is the target time point T_target, is a center of the one-cycle angular section.

As described above with respect to FIGS. 12A, 12B, and 12C, the first information 1280 may be acquired by using an MVF 1250. Referring to FIG. 21, the corrected first information 2180 represents a motion amount of the object in the one-cycle angular section necessary for reconstructing the final third image. In detail, the corrected first information 2180 is the information which represents the motion amount of the object in the time section between the time points b and c described above with reference to FIG. 18. Accordingly, the time section between the time points b and c in the corrected first information 2180 of FIG. 21 corresponds to the time section between the time points b and c in the corrected first information 1810 of FIG. 18.

A degree of motion of the object 2005 at the target time point T_target may be estimated by using the corrected first information 2180. Alternatively, a state which includes at least one of the size, shape, and position of the object 2005 at the target time point T_target may be estimated by using the corrected first information 2180.

As described above in FIG. 20, the projection data acquired in each view or a predetermined angular section included in the one-cycle angular section contributes to imaging of different surfaces and/or different areas of the object 2005.

In the reconstruction of a target image, the image reconstructor 620 may perform motion correction, by using the first information, with respect to a surface portion or an area of the object 2005 that is imaged by using the pieces of projection data acquired at time points other than the target time point T_target, except for a surface portion or area of the object 2005 that is imaged by using the projection data acquired at the target time point T_target.

In FIG. 21, for convenience of explanation, the one-cycle angular section, which is an angular section of pieces of projection data necessary for reconstructing one cross-sectional image, is divided into five angular sections 2101, 2102, 2103, 2104, and 2105, and images obtained by back-projecting projection data acquired in each of the five angular sections 2101, 2102, 2103, 2104, and 2105 are illustrated. In detail, a partial image 2121 is acquired by back-projecting the projection data acquired in the first angular section 2101. A partial image 2131 is acquired by back-projecting the projection data acquired in the second angular section 2102. A partial image 2141 is acquired by back-projecting the projection data acquired in the third angular section 2103. A partial image 2151 is acquired by back-projecting the projection data acquired in the fourth angular section 2104. A partial image 2161 is acquired by back-projecting the projection data acquired in the fifth angular section 2105.

Referring to FIG. 21, a start time point t=a and an end time point t=b of the one-cycle angular section are respectively the same as the start time point b and the end time point c, in the angular section corresponding to the raw data 1832 of FIG. 18. Referring to FIG. 21, a case in which the target time T_target is set to be a middle of the one-cycle angular section is described as an example. As described above with reference to FIG. 20, when the projection data acquired in an angular section adjacent to the target time T_target are back-projected, only surfaces 2142, 2143, 2144, and 2145 arranged in a horizontal direction are imaged in the partial image 2141. Surfaces that are not imaged in the partial image 2141 are imaged by using the pieces of projection data acquired in angular sections other than the third angular section 2103 which includes the target time T_target in the one-cycle angular section.

In the imaging of the surfaces that are not imaged in the partial image 2141, the image reconstructor 620 may perform motion correction by using the corrected first information 2180 in order to reduce blurring.

In detail, surfaces or partial areas shown in the partial image 2121 acquired in the first angular section 2101 are corrected based on the corrected first information 2180. In particular, referring to the corrected first information 2180, it is assumed that an amount W of motion of the object 2005 at the time point b is W11, and an amount W of motion of the object 2005 at the time point c is W12. For convenience of explanation, it is assumed that an amount W of motion of the object 2005 at the time point t11 in the first angular section 2101 is W11 likewise at the time point b, and an amount W of motion of the object 2005 at the time point t15 in the fifth angular section 2105 is W12 likewise at the time point c. It is also assumed that an amount W of motion of the object 2005 at the third time point t3, which is the target time point T_target, is W1. Then, the surface of the object 2005 at the third time point t3 may be accurately acquired by warping the object 2005 included in the partial image 2121 corresponding to the first angular section 2101 by a motion amount (W1−W11). Accordingly, a corrected partial image 2122 is generated by performing motion correction on the partial image 2121, based on a motion amount 2124 which is generated from the time point a to the third time point t3 and compared to a total motion amount (W12−W11) generated in the one-cycle angular section. A total motion amount 2123 may correspond to the total motion amount (W12−W11) generated in the one-cycle angular section, and the motion amount 2124 may correspond to a difference (W1−W11) between the motion amount W11 at the time point t=a and the motion amount W1 at the third time point t3, which is the target time point T_target. In detail, the total motion amount 2123 may be a value which corresponds to an MVF between an image at the time point a and an image at the time point b. For example, the total motion amount 2123 may be a value obtained by converting a sum of the absolute values of all motion vectors included in the MVF between the image at the time point a and the image the time point b into a weighting value.

Motion correction is performed on the other angular sections in the same manner as in the first angular section. In detail, the corrected partial image 2122 is generated by performing motion correction on the partial image 2131 obtained by back-projecting the projection data acquired in the second angular section 2102, based on a motion amount 2134 generated from the time point t12 to the third time point t3, which is the target time point T_target, as compared with the total motion amount 2123.

A corrected partial image 2162 is generated by performing motion correction on a partial image 2161 obtained by back-projecting the projection data acquired in the fifth angular section 2105, based on a motion amount 2164 generated from the end time point t=b to the third time point t3, which is the target time point T_target, compared to the total motion amount 2123. A corrected partial image 2152 is generated by performing motion correction on a partial image 2151 obtained by back-projecting the projection data acquired in the fourth angular section 2104, based on a motion amount 2154 generated from the time point t14 to the third time point t3, which is the target time point T_target, as compared with the total motion amount 2123.

The motion correction using the projection data acquired at a time point prior to the target time point T_target and the motion correction using the projection data acquired at a time point after the target time point T_target may be performed in opposite directions. In detail, referring to the corrected first information 2180, the motion correction prior to the target time T_target 2081 is performed in a direction 2185 in which the motion amount W increases, and the motion correction after the target time point T_target 2081 is performed in a direction 2186 in which the motion amount W decreases. Accordingly, the direction of the total motion amount 2123 at the time point t11 and the direction of the total motion amount 2123 at the time point t15 are illustrated to be opposite to each other.

The final third image which corresponds to the third time point t3, which is the target time point T_target, may be reconstructed by using the corrected partial images 2122, 2132, 2152, and 2162 and the partial image 2141 acquired in the third angular section 2103 which includes the target time point T_target. Since the corrected partial images 2122, 2132, 2152, and 2162 accurately reflect a motion state of the object 2005 at the third time point t3, generation of motion artifacts may be reduced in the final third image which is reconstructed by performing motion correction using the corrected first information 2180.

When an image is reconstructed by tomography scanning a moving object without performing motion correction, blurring may be severely generated in a surface portion due to the projection data acquired at a time point that is far from the target time point T_target. In detail, surfaces extending in the horizontal direction are imaged in the partial image 2141 acquired in the third angular section 2103 which includes the target time point T_target, and surfaces extending in a vertical direction that are not imaged in the partial image 2141 are imaged in the partial image 2121 and the partial image 2161 which respectively correspond to the time point t1 and the time point t15 that are located farthest from the target time point T_target. Due to the motion of the object 2005, the surfaces imaged in partial image 2121 acquired in the first angular section 2101 that is a start angular section and the partial image 2161 acquired in the fifth angular section 2105 that is an end angular section are considerably different in their positions and sizes. In particular, blurring is most severely generated in an image which is finally reconstructed by using the projection data acquired in the start angular section and the projection data acquired in the end angular section. Accordingly, the surfaces extending in the vertical direction in the target image are blurred due to the surfaces having different positions and sizes and imaged in the partial image 2121 and the partial image 2161.

In an exemplary embodiment, the image reconstructor 620 may generate a target image 2170 by performing motion correction on the plurality of partial images acquired in the one-cycle angular section by using the first information, and thus motion artifacts may be reduced.

Further, when the target time point T_target is set to be the middle of the one-cycle angular section from the first time point t11 and the end time point t15, motion artifacts in the reconstructed image may be reduced. Accordingly, the target time point T_target may be set to be the middle time of the one-cycle angular section, and motion correction is performed by using corrected first information, and thus a target image having an optimized image quality may be reconstructed.

Although FIG. 21 illustrates a case in which the one-cycle angular section is divided into a plurality of angular sections and motion correction is performed for each of a plurality of back-projected images which respectively correspond to the plurality of angular sections, the motion correction may be performed on a partial image obtained by back-projecting the projection data acquired in each view included in the one-cycle angular section. Alternatively, the motion correction may be performed in a process of back-projecting the projection data acquired in each view. The motion correction may be performed on a partial image obtained by back-projecting the projection data acquired in a view group including several views. Alternatively, the motion correction may be performed in a process of back-projecting the projection data acquired in the view group.

Although FIG. 21 illustrates a case of performing motion correction on the partial images, motion correction may be performed on projection data which corresponds to each view, and the target image may be reconstructed by performing filtered back-projection on the corrected projection data which corresponds to each view.

Figure 22:
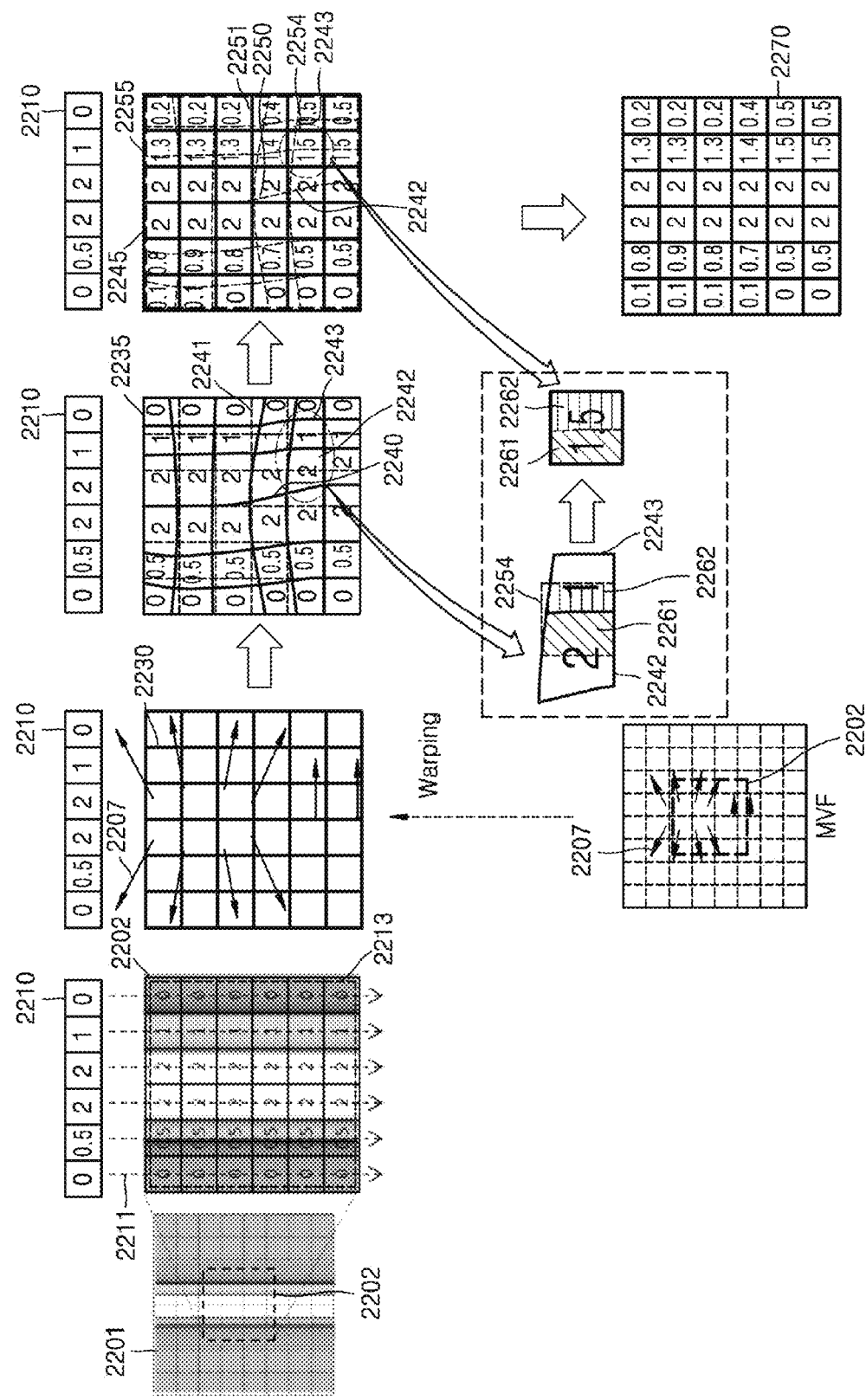
FIG. 22 is a view which illustrates a warping operation used to reconstruct a tomography image.

FIG. 22 is a view which illustrates a warping operation used to reconstruct a tomography image.

To reconstruct a target image, the image reconstructor 620 performs back-projection, that is, reflects the filtered projection data acquired at a plurality of views included in the one-cycle angular section in an image domain 2201 which indicates the object. In the following description, the back-projection is performed on a partial area 2202 included in the image domain 2201. The area 2202, as illustrated in FIG. 22, may include image data which includes pixel values or an image represented by pixel values. Further, the area 2202 may include an image space for imaging the object. In FIG. 22, a case in which filtered projection data 2210 acquired as X-rays are projected in a direction 2211 at the first time t11 in FIG. 21 that is the start time point of the one-cycle angular section is back-projected is described as an example. The image data included in the area 2202 may be referred to as back-projected projection data.

Referring to FIG. 22, the image reconstructor 620 may warp an image grid formed of a plurality of pixels for imaging the object according to a motion amount of the object at the target time point T_target based on the first information, and may reconstruct the target image by using a warped image grid.

In detail, referring to FIG. 22, the filtered projection data 2210 is reflected to the image grid included in the area 2202. The reflection of the filtered projection data 2210 to the image grid that includes an image space is referred to as back-projection.

Accordingly, the area 2202 is filled with pixel values 2213, as illustrated in FIG. 22. When no motion is generated by the object, motion artifacts may not be generated in a reconstructed target image, even if an image is imaged while the filtered projection data 2210 according to each view is accumulatively reflected to the image grid. However, when motion is generated by the object during the one-cycle angular section, a difference between surfaces which indicate the same portion of the object is generated in a plurality of pieces of the filtered projection data respectively acquired at a plurality of views. Accordingly, when the filtered projection data 2210 according to each view is accumulatively reflected to the image grid to image the image, motion artifacts may be generated in a reconstructed target image.

In the present exemplary embodiment, in order to reduce motion artifacts of a moving object, motion correction is performed as described above with reference to FIG. 21. In the following description, warping of the image grid of the image reconstructor 620 for motion correction is described in detail.

The image reconstructor 620 warps an image grid 2230 for imaging the same portion as the area 2202 according to the MVF indicating a motion amount of the object toward the target time point T_target in the area 2202, by using corrected first information which indicates motion of the object. For example, the upper left area in the image grid 2230 may be warped according to vectors in the MVF 2207. The MVF 2207 indicates a motion amount of a surface of the object.

Accordingly, an image grid 2240 warped from the image grid 2230 is generated. The image reconstructor 620 reflects pixel values included in the filtered projection data 2210 to the image grid 2240 that is warped. Accordingly, the pixel values are included in an area 2235 which identically corresponds to the area 2202, as illustrated in FIG. 22. In the area 2235, a rectangular image grid 2241 represented as a dotted grid indicates a general image grid that is not warped.

Next, the image reconstructor 620 resamples the area 2235 which includes the pixel values according to the warped image grid 2240 to an area 2245 which includes pixel values according to the rectangular image grid 2241. In detail, the pixel values according to the warped image grid 2240 are interpolated by using a quadratic image pixel matrix and are thus transformed to pixel values according to Cartesian coordinates.

In the following description, a case of resampling pixel values of pixels 2242 and 2243 included in the warped image grid 2240 to a pixel value of a pixel 2254 included in the rectangular image grid 2241 is described as an example. The pixel 2242 included in the warped image grid 2240 has a signal value "2" and the pixel 2243 has a signal value "1". In this aspect, since an image signal value included in the entire area of the pixel 2242 is 2, the signal value "2" is included in the pixel 2242 by being distributed at an area ratio of the pixel 2242. Accordingly, a signal value "1" may be included in a partial area 2261 which corresponds to the half of the entire area of the pixel 2242. Since an image signal value included in the entire area of the pixel 2243 is 1, the signal value "1" is included in the pixel 2243 by being distributed at an area ratio of the pixel 2243. Accordingly, a signal value "0.5" may be included in a partial area 2262 which corresponds to the half of the entire area of the pixel 2242. A signal value "1.5" that is a sum of the signal value "1" of the partial area 2261 and the signal value "0.5" of the partial area 2262 may be included in the pixel 2254 according to the rectangular image grids 2241 and 2251 which include the partial area 2261 and the partial area 2262.

Accordingly, pixel values 2255 are arranged in the area 2245 that is resampled, according to the rectangular image grid 2251. Accordingly, the pixel values 2255 included in the area 2245 may be generated by resampling all pixel values included in the area 2235.

In addition to the above method, any of various methods may be employed as the method for transforming the pixel values arranged according to a warped image grid to the pixel values arranged according to a rectangular image grid.

Motion correction may be performed by using warping with respect to each of all pieces of back-projected projection data which respectively correspond to a plurality of views included in the one-cycle angular section. The final third image, which is the target image, may be reconstructed by accumulating the back-projected projection data on which motion correction is performed.

The motion correction achieved via warping of an image grid may not be performed for each view, but the motion correction may be performed for each predetermined angular section or for each group into which a plurality of views are divided.

As in the above-described example, the image reconstructor 620 may generate motion-corrected image data 2270 by using an image grid warped based on the first information.

Figure 23:
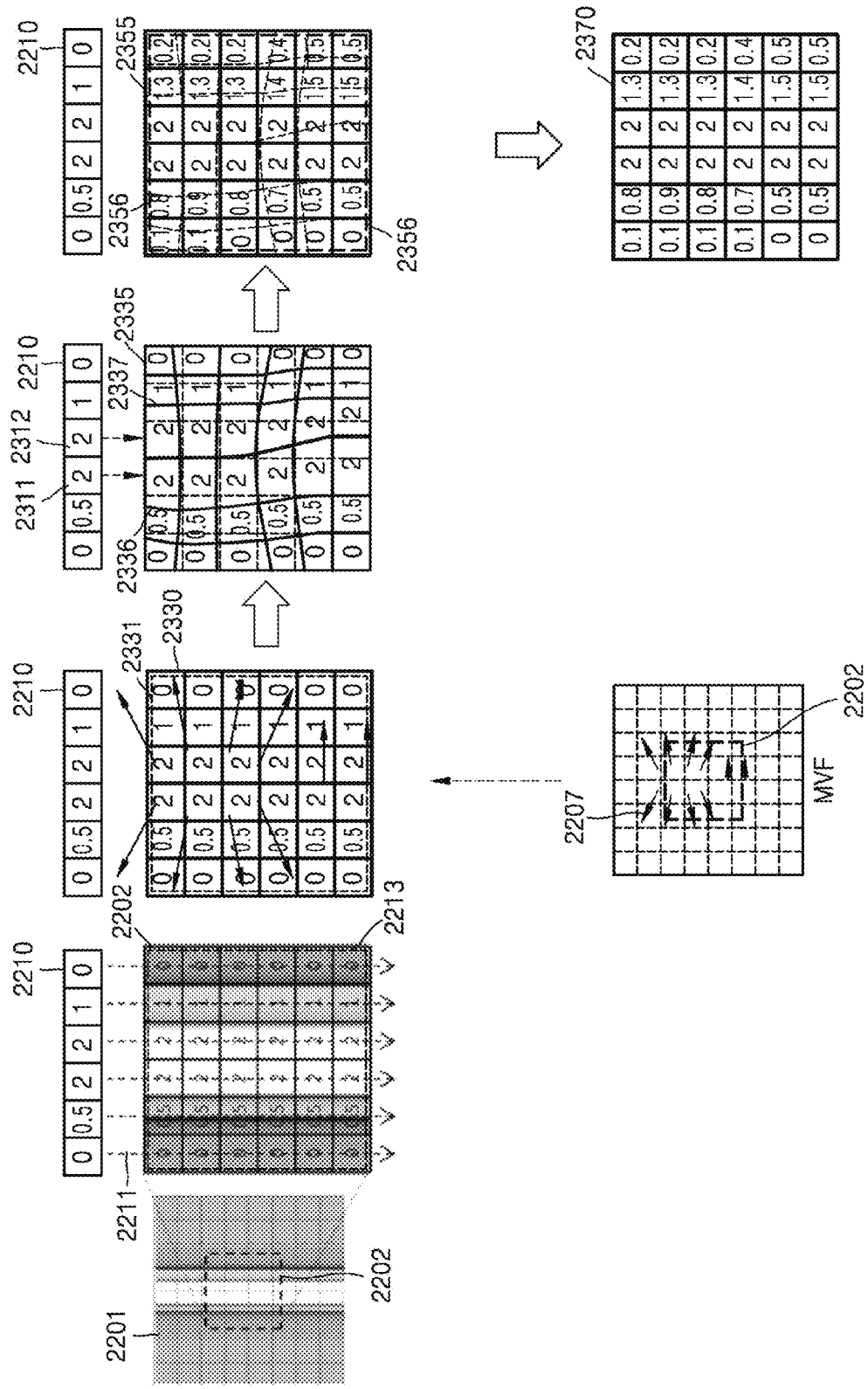
FIG. 23 is another view which illustrates a warping operation used to reconstruct a tomography image.

FIG. 23 is another view which illustrates a warping operation used to reconstruct a tomography image. A repeated description of matters described above with reference to FIG. 22 is omitted herein.

In detail, the image reconstructor 620 may generate a motion-corrected target image by warping the back-projected image according to the first information. In detail, in the back-projection process, the image reconstructor 620 may reconstruct the target image by warping the pixel which corresponds to the data acquired via a tomography scan based on the first information. In detail, the image reconstructor 620 may warp the pixel according to a motion amount of the object at the target time point T_target.

Referring to FIG. 23, pixels of an image (or image data) 2330 generated by back-projecting the filtered projection data 2210 are warped based on the MVF 2207 which indicates a motion amount of the corrected first information. Accordingly, pixel values of pixels 2331 included in the image 2330 are generated into a warped image 2335 which corresponds to a motion of the object at the target time point T_target based on the MVF 2207. In detail, a pixel value "2" of filtered projection data 2311 corresponds to pixel values "2" of pixels 2336 in third column of the warped image 2335. A pixel value "2" of filtered projection data 2312 corresponds to pixel values "2" of pixels 2337 in the fourth column of the warped image 2335.

The warped image 2335 generates a motion-corrected image 2355 by performing resampling in the method described above with reference to FIG. 22. Pixel values of pixels 2356 included in the motion-corrected image 2355 accurately reflect motion of the object at the target time point T_target. Accordingly, motion artifacts in a final third image, which is a finally reconstructed target image, may be reduced.

Figure 24:
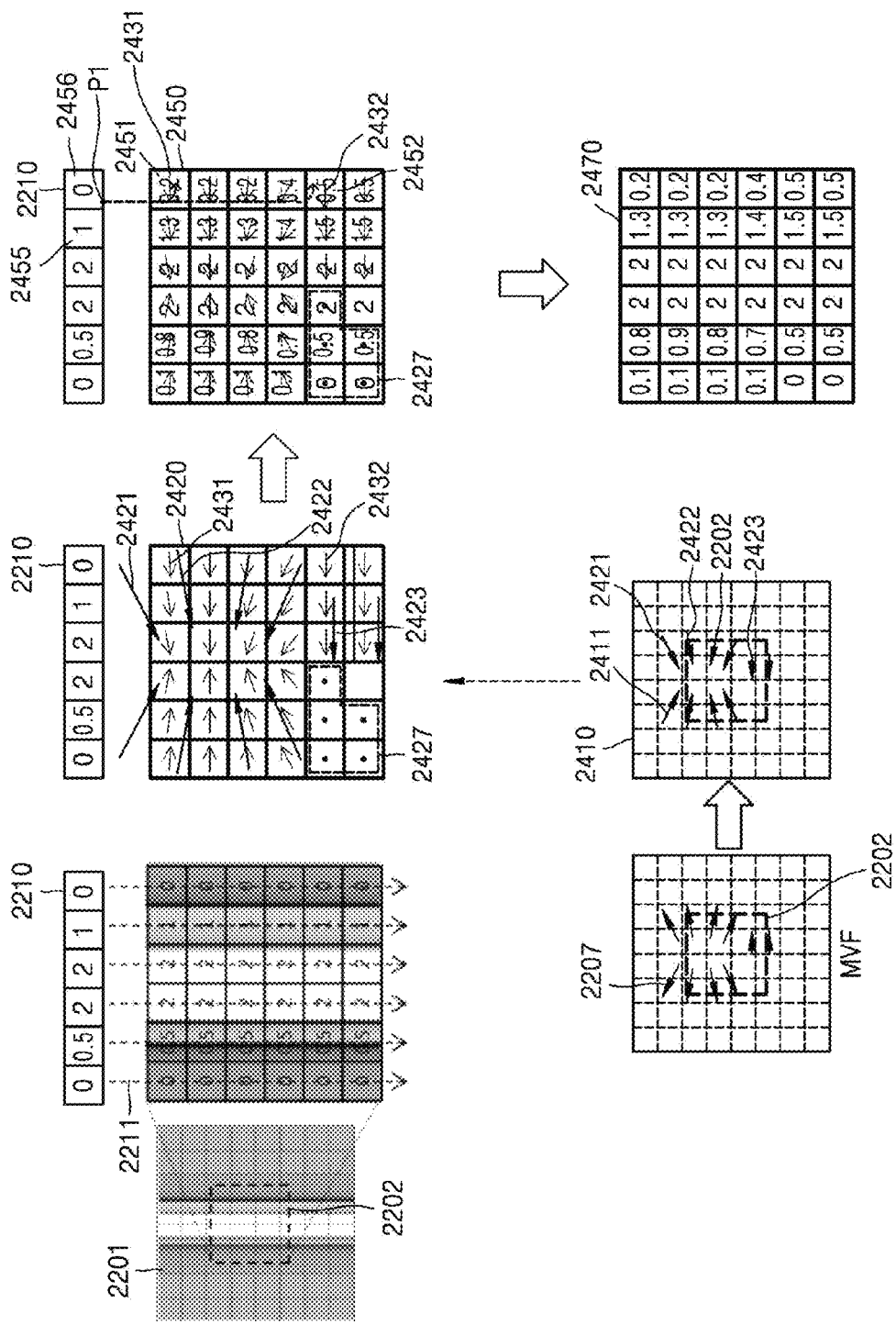
FIG. 24 is another view which illustrates a warping operation used to reconstruct a tomography image.

FIG. 24 is another view which illustrates a warping operation used to reconstruct a tomography image.

A repeated description of matters described above with reference to FIGS. 22 and 23 is omitted herein. The image reconstructor 620 may perform motion correction in the back-projection process based on the first information. In detail, the image reconstructor 620 may warp the center of a voxel which indicates the object based on the first information, and may reconstruct a target image by back-projecting the position of a warped voxel and/or the position of a warped center of a voxel. The voxel indicates one unit space in a virtual 3D grid space which is used for imaging the object. In FIG. 24, a case in which the virtual 3D grid space used for imaging the object is illustrated with pixels that form a 2D grid space instead of voxels that form a 3D grid space is illustrated as an example.

In detail, the image reconstructor 620 may find which of values of pixels in a detector array should be referred to, by using the MVF from the third time point, which is the target time point T_target, to each time point when a pixel value at a predetermined position in an image to be reconstructed is affected by a motion at each time point. In view of the voxel which indicates the object at the target time point T_target, in order to back-project the filtered projection data at a view other than the target time point T_target toward a voxel, a destination of a voxel where a voxel moves at a corresponding time point needs to be calculated by reflecting motion of the object. The motion amount of a voxel to correct motion of the object may be calculated by using an inverse MVF of the MVF from a corresponding time point to the target time point T_target. The value of the pixel in the detector array to be used after the position of a voxel is moved according to a calculated correction amount may be calculated.

In detail, referring to FIG. 24, the image reconstructor 620 performs field inversion on the MVF which indicates the motion amount of the object at the target time point T_target, which is indicated by the corrected first information, and generates a field-inverted MVF 2410. The position of each pixel in a back-projected image 2420 is moved by using the field-inverted MVF 2410.

For example, the positions of the pixels in the back-projected image 2420 are moved based on motion vectors 2411, 2421, 2422, and 2423 included in the field-inverted MVF 2410. In detail, a pixel in the first row and sixth column in the back-projected image 2420 is moved as an arrow 2431 based on the vector 2421 and the vector 2422. A pixel in the fifth row and sixth column in the back-projected image 2420 is moved as an arrow 2432 based on the motion vector 2423. The position of a pixel in an area 2427 of the field-inverted MVF 2410 where no motion is detected remains the same.

Next, the image reconstructor 620 calculates which position of the detector array corresponds to a pixel value in a particular pixel when the pixel value of the particular pixel is projected based on a moved pixel position, and takes the filtered projection data 2210 at a calculated position in order to accumulate a value in the particular pixel (voxel), thereby acquiring the back-projected image 2420.

For example, considering the moved position 2431, the center of a pixel 2451 in the first row and sixth column in the back-projected image 2450 is acquired by using a pixel value at a position P1 in the filtered projection data 2210. The position P1 is not located at the center of a pixel 2456 in the first row and sixth column in the filtered projection data 2210, but instead is located close to a pixel 2455 in the first row and fifth column, thereby being affected by the pixel 2456 and the pixel 2455. Accordingly, the pixel 2451 may have a value "0.2" by being affected by the pixel 2456 having a value "0" and the pixel 2455 having a value "1", as illustrated in FIG. 24.

Similarly, the center of a pixel 2452 in the fifth column and the sixth column in the back-projected image 2450 is located on a surface of the pixel 2452 and a pixel 2457 that neighbor each other according to a motion 2432 of the pixel, as illustrated in FIG. 24. Accordingly, the pixel 2451 is affected by the pixel 2456 and the pixel 2455. Accordingly, the pixel 2451 may have a value "0.5" that is a middle value between the pixel 2456 having a value "0" and the pixel 2455 having a value "1".

As described above, the image reconstructor 620 may acquire a motion-corrected target image 2470 that is a motion-corrected back-projected image by warping a voxel by using a field-inverted MVF, rather than by using the warping described above with reference to FIGS. 22 and 23.

The image reconstructor 620 may perform motion correction on the first and second images based on the corrected first information, similarly as performing motion correction on the object and reconstructing the final third image by using the corrected first information. In addition, the image reconstructor 620 may reacquire the first information by using motion-corrected first and second images. The image reconstructor 620 may update the corrected first information with the reacquired first information. In detail, when motion correction is performed on the first and second images based on the corrected first information, motion-corrected first and second images may be acquired by more accurately reflecting respective states of the object at the first and second time points. When the MVF is reacquired by using the motion-corrected first and second images, a motion amount between the first and second time points may be more accurately measured. Therefore, the first information may be updated by being reacquired to have a more accurate value.

The image reconstructor 620 may predict the third image which corresponds to the third time point t3 between the first and second time points t1 and t2 based on the reacquired first information, and correct the reacquired first information by using the predicted third image and measured data which corresponds to the third time point t3, thereby acquiring corrected first information.

As described above, when motion correction is performed on the first and second images based on the corrected first information and then the MVF is acquired using the motion-corrected first and second images, the first information may be more accurately acquired.

Figure 25A:
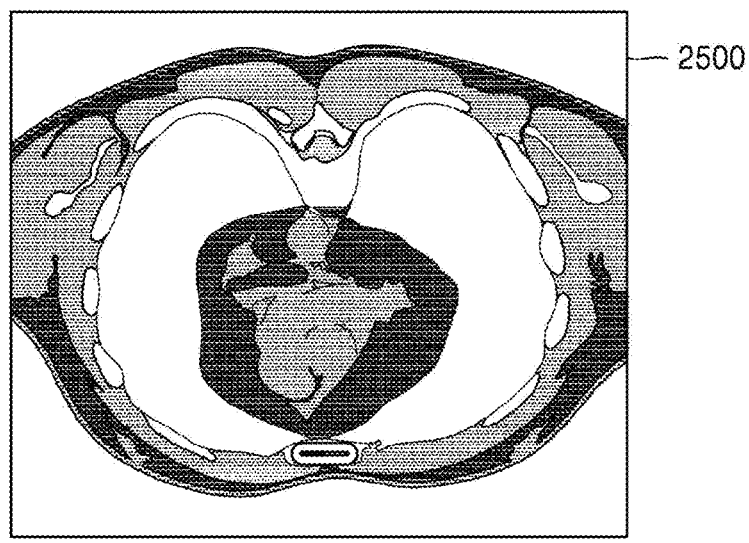
FIGS. 25A and 25B illustrate screen images displayed on the tomography apparatus of FIG. 6.
Figure 25B:
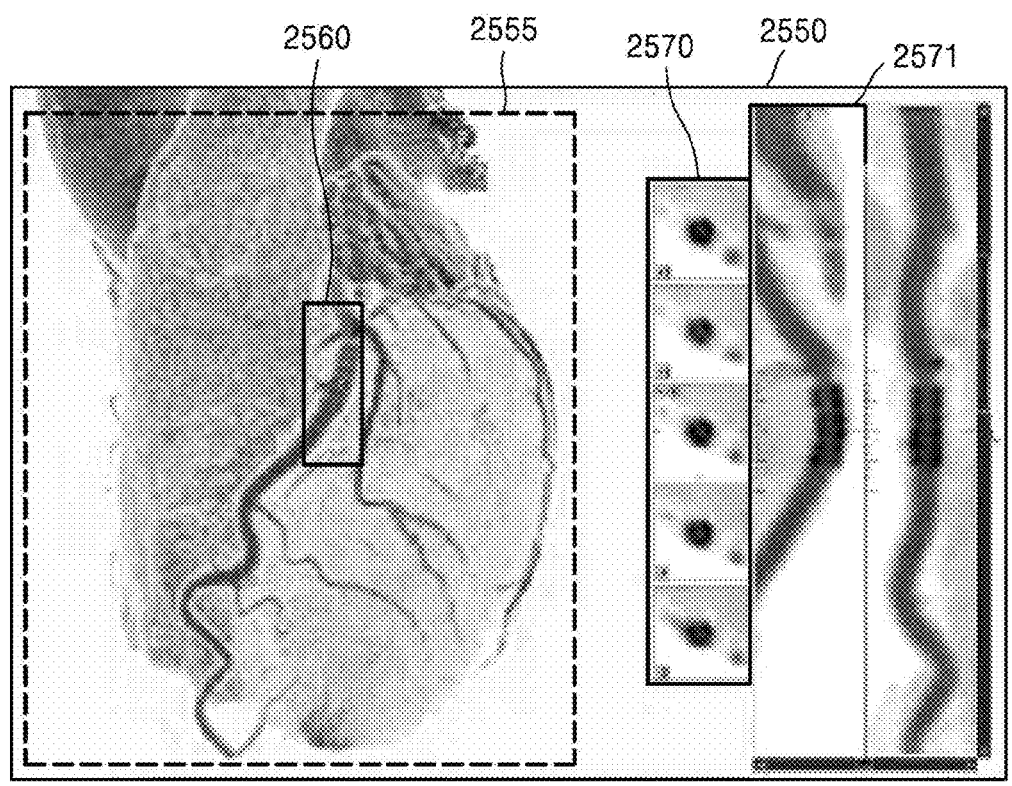

FIGS. 25A and 25B illustrate screen images displayed on the tomography apparatus 600 of FIG. 6. In detail, FIG. 25A illustrates a 2D tomography image 2500 reconstructed by using the corrected first information. FIG. 25B illustrates a 3D tomography image 2550 reconstructed by using the corrected first information.

Referring to FIG. 25A, the display 630 may display the 2D tomography image 2500 reconstructed by using the corrected first information.

In detail, a user may select a target time point (e.g., the third time point t3) within the total time section at which image reconstruction is desired to be performed, via the user interface 650. Then, the image reconstructor 620 may reconstruct the 2D tomography image 2500 which corresponds to the selected target time point (e.g., the third time point t3) by warping at least one of the first and second images, by using the corrected first information. The reconstructed 2D tomography image 2500 may be displayed on the display 630.

Referring to FIG. 25B, the display 630 may display the 3D tomography image 2550 reconstructed by using the corrected first information. In FIG. 25B, the 3D tomography image 2550 represents a heart three-dimensionally.

The user interface 650 may receive information which indicates a region of interest (ROI) 2560 from a user. When the ROI 2560 is set, the 3D tomography image 2550 may include at least one selected from an image 2555 which represents the entire portion of the heart, which is an object, and partial images 2570 and 2571 which respectively represent the ROI 2560 in detail. For example, the partial image 2570 may be a blood vessel cross-sectional image in the ROI 2560, and the partial image 2571 may be an image obtained by magnifying the object included in the ROI 2560.

Figure 26:
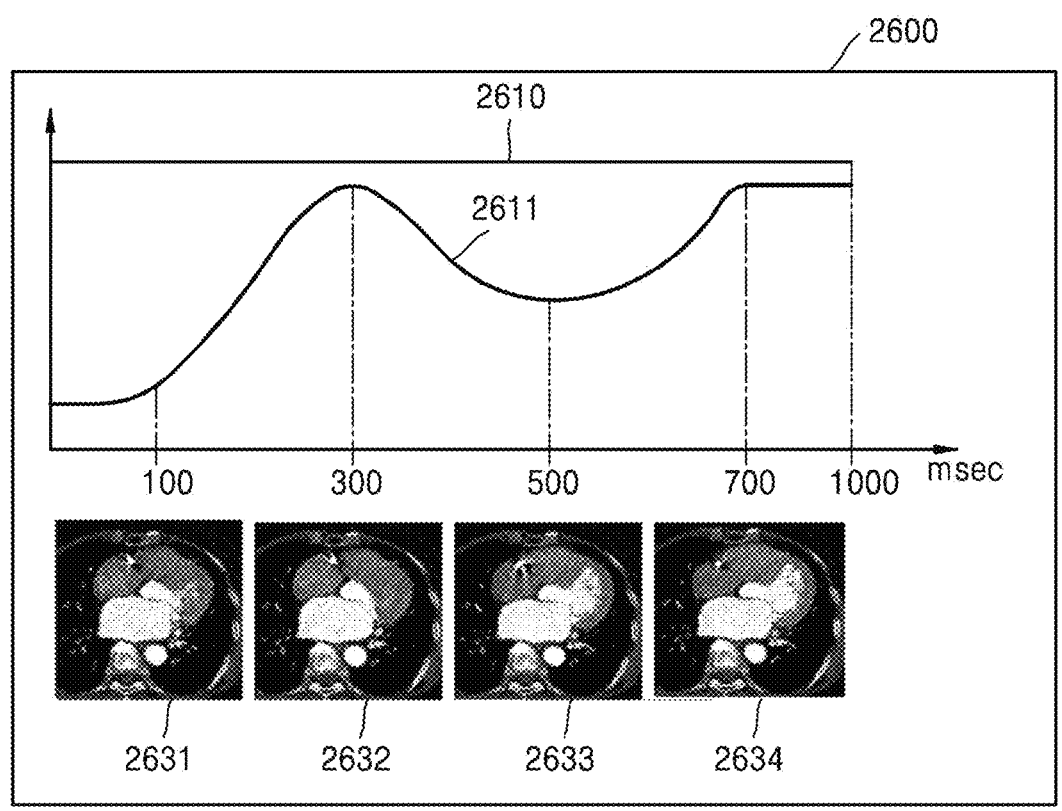
FIG. 26 illustrates a screen image displayed on the tomography apparatus of FIG. 6.

FIG. 26 illustrates a screen image 2600 displayed on the tomography apparatus 600 of FIG. 6.

The image reconstructor 620 may reconstruct a plurality of images which respectively correspond to a plurality of time points between the first and second time points t1 and t2. The plurality of time points between the first and second time points t1 and t2 may be automatically set by the image reconstructor 620, or may be manually set via the user interface 650. For example, when the plurality of time points between the first and second time points t1 and t2 may be automatically set by the image reconstructor 620, the image reconstructor 620 may divide a time section between the first and second time points t1 and t2 at regular intervals in order to obtain a plurality of time points, and may reconstruct the plurality of images respectively in correspondence with the plurality of time points.

The display 630 may display a screen image which includes a plurality of images produced by the image reconstructor 620.

Referring to FIG. 26, the screen image 2600 may include a plurality of images 2631, 2632, 2633, and 2634 which respectively correspond to the plurality of time points between the first and second time points t1 and t2.

The screen image 2600 may include a UI screen image, and may display corrected first information 2611. A user may select some time points from the corrected first information 2611. Then, the image reconstructor 620 may reconstruct images which respectively correspond to the selected time points and control the reconstructed images to be displayed on the screen image 2600.

In FIG. 26, a case where 100 msec, 300 msec, 500 msec, and 700 msec are selected as the time points of the images desired to be reconstructed is illustrated as an example. Accordingly, as illustrated in FIG. 26, the screen image 2600 may include an image 2631 corresponding to 100 msec, an image 2632 corresponding to 300 msec, an image 2633 corresponding to 500 msec, and an image 2634 corresponding to 700 msec.

Figure 27:
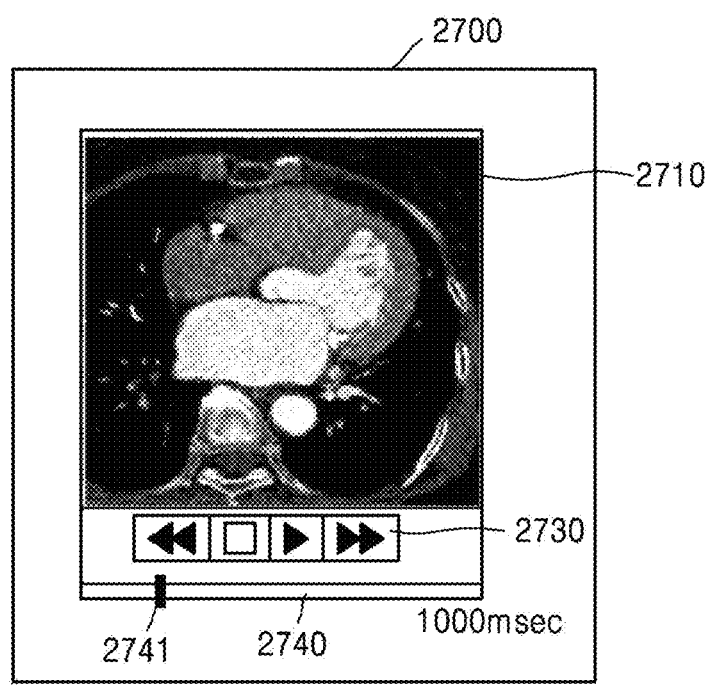
FIG. 27 illustrates a screen image displayed on the tomography apparatus of FIG. 6.

FIG. 27 illustrates a screen image displayed on the tomography apparatus 600 of FIG. 6.

The image reconstructor 620 may reconstruct a plurality of images which respectively correspond to a plurality of time points between the first and second time points t1 and t2 and produce a moving picture 2710 that sequentially reproduces the reconstructed images in chronological order.

The display 630 may display a UI screen image 2700 which relates to reproducing the moving picture 2710.

Referring to FIG. 27, the UI screen image 2700 includes a moving picture reproducing menu image 2730 which relates to reproducing the moving picture 2710. The moving picture 2710 sequentially reproduces the plurality of images which respectively correspond to the plurality of time points between the first and second time points t1 and t2 in chronological order. The UI screen image 2700 may further include a menu 2740 which represents a total time section, and a menu 2741 which displays a time point which corresponds to an image that is currently being reproduced.

As described above, by sequentially displaying images which correspond to a plurality of time points included in the total time section, a motion change of the object according to the elapsement of time may be easily ascertained.

FIGS. 28A and 28B are views which illustrate motion artifacts existing in a reconstructed tomography image. In detail, FIG. 28A illustrates tomography images reconstructed by the tomography apparatuses 500 and 600 according to one or more exemplary embodiments. FIG. 28B illustrates tomography images reconstructed by a tomography apparatus of the related art according to the back-projection method.

Referring to a block 2810 of FIG. 28A, a plurality of reconstructed images 2821, 2822, 2823, 2824, and 2825 reconstructed by using corrected first information and at least one of the first and second images are illustrated. The plurality of reconstructed images 2821, 2822, 2823, 2824, and 2825 are tomography images which respectively correspond to a plurality of time points within a total time section.

Referring to a block 2850 of FIG. 28B, a plurality of tomography images 2861, 2862, 2863, 2864, and 2865 reconstructed according to the back-projection method are illustrated. The plurality of reconstructed images 2861, 2862, 2863, 2864, and 2865 may be tomography images which respectively correspond to a plurality of time points within the total time section.

When the images of FIG. 28A are compared with those of FIG. 28B, the images 2821 and 2861 are images reconstructed at the same time point, and the images 2822 and 2862 are images reconstructed at the same time point. The images 2823 and 2863 are images reconstructed at the same time point, the images 2824 and 2864 are images reconstructed at the same time point, and the images 2825 and 2865 are images reconstructed at the same time point.

When the images 2822 and 2862 are compared with each other, an edge within a partial area 2871 is inaccurately reconstructed due to motion artifacts present in the image 2862, whereas an edge within a partial area 2811 which corresponds to the partial area 2871 is accurately reconstructed in the image 2822.

When the images 2823 and 2863 are compared with each other, an edge within a partial area 2872 is inaccurately reconstructed due to motion artifacts present in the image 2863, whereas an edge within a partial area 2812 which corresponds to the partial area 2872 is accurately reconstructed in the image 2823.

When the images 2824 and 2864 are compared with each other, an edge within a partial area 2873 is inaccurately reconstructed due to motion artifacts present in the image 2864, whereas an edge within a partial area 2813 which corresponds to the partial area 2873 is accurately reconstructed in the image 2824.

Figure 29A:
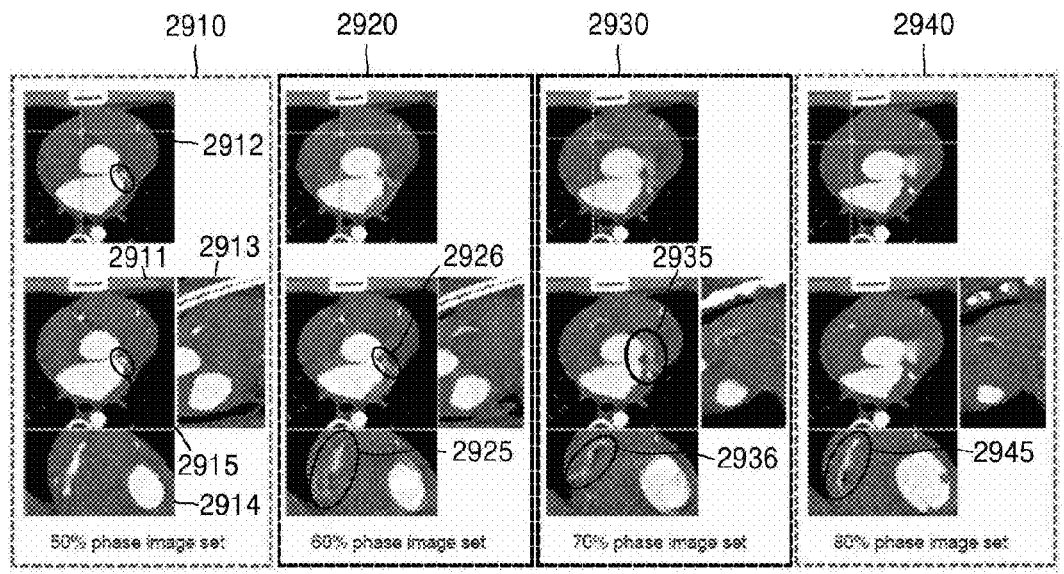
FIGS. 29A and 29B are views which illustrate motion artifacts existing in a reconstructed tomography image.
Figure 29B:
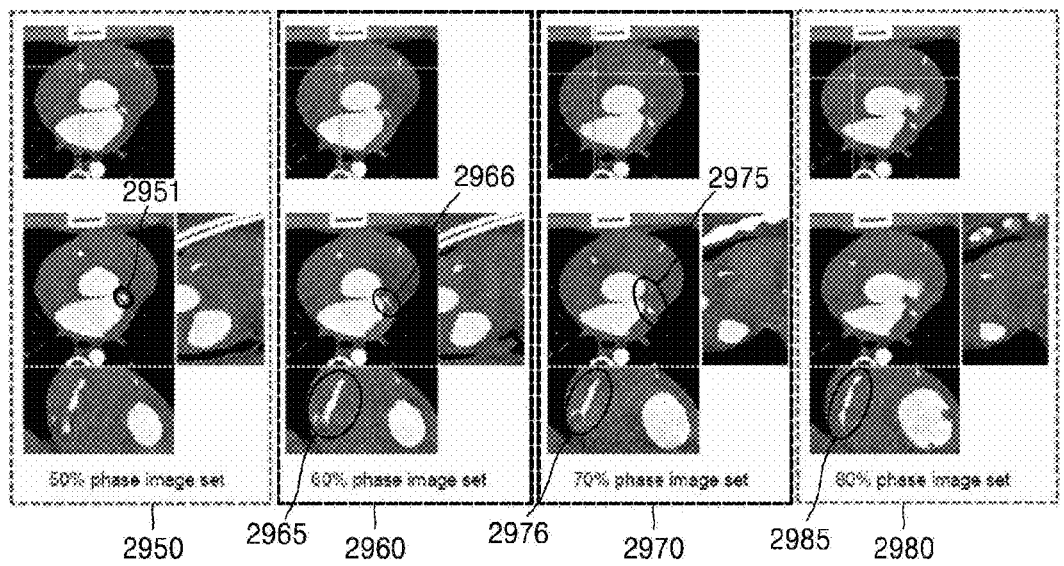

FIGS. 29A and 29B are views which illustrate motion artifacts existing in a reconstructed tomography image.

In detail, FIG. 29A illustrates heart tomography images reconstructed by a tomography apparatus of the related art according to the back-projection method. In detail, FIG. 29B illustrates heart tomography images reconstructed by the tomography apparatuses 500 and 600 according to one or more exemplary embodiments.

Referring to FIG. 29A, a plurality of image sets 2910, 2920, 2930, and 2940 reconstructed according to the back-projection method are illustrated. The plurality of image sets 2910, 2920, 2930, and 2940 are tomography images which respectively correspond to a plurality of time points within the R-R time section.

Referring to FIG. 29B, a plurality of image sets 2950, 2960, 2970, and 2980 reconstructed by using corrected first information and at least one of the first and second images are illustrated. The plurality of image sets 2950, 2960, 2970, and 2980 are tomography images which respectively correspond to a plurality of time points within the R-R time section.

In each image set (e.g., 2910), an image 2912 at the upper portion and an image 2911 on the left side of the center portion are images which represent a transaxial cross-section of the abdomen, an image 2913 on the right side of the center portion is an image which represents a sagittal cross-section of the abdomen, and an image 2914 at the lower portion is an image which represents a coronal cross-section of the abdomen.

The images sets 2910 and 2950 are sets of reconstructed images which represent a time point which corresponds to 50% of the R-R time section, and the images sets 2920 and 2960 are sets of reconstructed images which represent a time point which corresponds to 60% of the R-R time section. The images sets 2930 and 2970 are sets of reconstructed images which represent a time point which corresponds to 70% of the R-R time section, and the images sets 2940 and 2980 are sets of reconstructed images which represent a time point which corresponds to 80% of the R-R time section.

When the images sets 2910 and 2950 are compared with each other, a plurality of partial areas, namely, partial area 2915, where motion artifacts are present noticeably appear in the reconstructed images within the image set 2910, whereas motion artifacts are remarkably reduced in the image set 2950. In detail, an edge of the object is clearly reconstructed due to a rare presence of motion artifacts within an area 2951 which corresponds to an area 2915 which represents a coronary artery within the heart.

When the images sets 2920 and 2960 are compared with each other, a plurality of partial areas, namely, partial areas 2925 and 2926, where motion artifacts are present noticeably appear in the reconstructed images within the image set 2920, whereas motion artifacts are remarkably reduced in the image set 2960. In detail, an edge of the coronary artery is clearly reconstructed due to a rare presence of motion artifacts within areas 2965 and 2966 which respectively correspond to the areas 2925 and 2926.

When the images sets 2930 and 2970 are compared with each other, a plurality of partial areas, namely, partial areas 2935 and 2936, where motion artifacts are present noticeably appear in the reconstructed images within the image set 2930, whereas motion artifacts are remarkably reduced in the image set 2970. In detail, an edge of the coronary artery is clearly reconstructed due to a rare presence of motion artifacts within areas 2975 and 2976 which respectively correspond to the areas 2935 and 2936.

When the images sets 2940 and 2980 are compared with each other, a plurality of partial areas, namely, partial area 2945, where motion artifacts are present noticeably appear in the reconstructed images within the image set 2940, whereas motion artifacts are remarkably reduced in the image set 2980. In detail, an edge of the coronary artery is clearly reconstructed due to a rare presence of motion artifacts within an area 2985 which corresponds to the area 2945.

In a conventional apparatus and method of reconstructing a tomography image, when a tomography scan is performed on a moving object, an image of the object is not clearly reconstructed due to motion artifacts. For example, when the entire heart is scanned, even when a section during which motion of the heart is minimal is found from the R-R time section via ECG gating and then a tomography image is reconstructed, motion artifacts are present within the reconstructed tomography image due to periodic heart beating of the heart. At other time points during which ECG gating is not performed in the R-R time section, it is difficult to reconstruct an accurate image due to an increase in motion artifacts.

To address this problem, in the related art, a tomography image is reconstructed at an end time point of systole or an end time point of diastole. To minimize motion artifacts which are caused due to motion of the heart, a beta blocker is injected into a patient so that the heartbeat of the patient decreases, and then a tomography scan is performed. However, in conventional tomography image reconstruction, it is difficult to prevent motion artifacts which are caused due to motion of the heart.

As described above, in one or more exemplary embodiments, first information which represents a motion of an object is corrected to more accurately reflect the motion of the object, and thus the first information may more accurately reflect a motion change of the object. Moreover, image reconstruction is performed using the corrected first information, and thus an image having a high temporal resolution may be reconstructed and an image in which motion artifacts are minimized may be reconstructed. Therefore, a user may more accurately diagnose a disease by using a tomography image in which motion artifacts are minimized.

Figure 30:
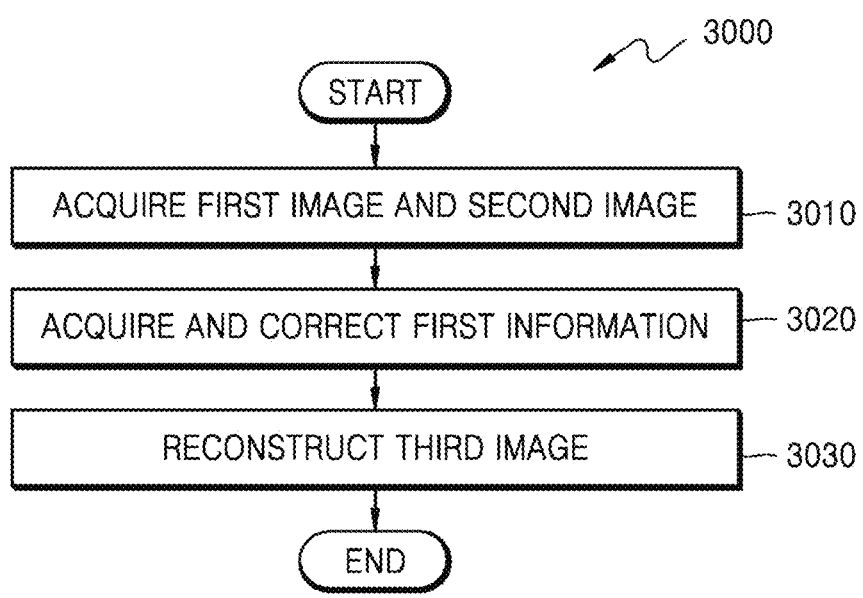
FIG. 30 is a flowchart of a tomography image reconstructing method, according to an exemplary embodiment.

FIG. 30 is a flowchart of a tomography image reconstructing method 3000, according to an exemplary embodiment. The operations included in the tomography image reconstructing method 3000 are the same as the operations performed in the tomography apparatuses 500 and 600 described above with reference to FIGS. 1A-29B. Accordingly, descriptions of the tomography image reconstructing method 3000 that are the same as those made with reference to FIGS. 1A-29B are not repeated herein.

Referring to FIG. 30, a first image which corresponds to a first time point and a second image which corresponds to a second time point are acquired by performing a tomography scan on an object, in operation 3010. The operation 3010 may be performed by the data acquirer 610 of the tomography apparatus 600.

First information which indicates a relationship between a motion amount of the object and a corresponding time amount is acquired based on a motion amount between the first image and the second image. Then, in operation 3020, a third image which corresponds to a third time point between the first and second time points is predicted based on the first information, and the first information is corrected based on obtained data which corresponds to the third time point and the predicted third image. The operation 3020 may be performed by the image reconstructor 620 of the tomography apparatus 600. The first information may be information which indicates a relationship between a motion amount of the object corresponding to an MVF between the first image and the second image and the corresponding time amount.

In operation 3030, the third image is reconstructed by using the corrected first information. The operation 3030 may be performed by the image reconstructor 620 of the tomography apparatus 600.

The exemplary embodiments can be written as computer programs and can be implemented in general-use digital computers that execute the programs using a transitory or non-transitory computer readable recording medium.

Examples of the computer readable recording medium include magnetic storage media (e.g., ROM, floppy disks, hard disks, etc.), optical recording media (e.g., CD-ROMs, or DVDs), etc.

It should be understood that the exemplary embodiments described above should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the present disclosure as defined by the following claims.

What is claimed is:

1. A tomography apparatus comprising:
a processor configured to:
acquire a first image corresponding to a first time point and a second image corresponding to a second time point by performing a tomography scan on an object;
acquire first information representing a relationship between time and a motion amount of the object based on a motion amount between the first image and the second image;
predict a third image corresponding to a third time point between the first time point and the second time point based on the first information;
correct the first information by using the predicted third image and measured data corresponding to the third time point; and
reconstruct a final third image corresponding to the third time point by using the corrected first information.

2. The tomography apparatus of claim 1, wherein the first information is information indicating a relationship between time and a motion amount of the object corresponding to a motion vector field (MVF) between the first image and the second image.

3. The tomography apparatus of claim 1, wherein the processor is further configured to correct the first information based on predicted data acquired by forward projecting the predicted third image and the measured data.

4. The tomography apparatus of claim 3, wherein the processor is further configured to compare the predicted data with the measured data and correct the first information so that a difference between the predicted data and the measured data decreases.

5. The tomography apparatus of claim 1, wherein the processor is further configured to compare a predicted sinogram acquired by forward projecting the predicted third image with a measured sinogram acquired by detecting X-rays that have been projected by the object within a time section corresponding to the third time point, and correct the first information so that a difference between the predicted sinogram and the measured sinogram decreases.

6. The tomography apparatus of claim 1, wherein the processor is further configured to compare a fourth image obtained by back-projecting measured data acquired at the third time point with the predicted third image, and correct the first information so that a difference between the predicted third image and the fourth image decreases.

7. The tomography apparatus of claim 1, wherein the processor is further configured to correct the first information at the third time point which is a time point apart from the first time point toward the second time point by a first time period.

8. The tomography apparatus of claim 1, wherein the processor is further configured to correct the first information at the third time point which is a time point apart from the second time point toward the first time point by a first time period.

9. The tomography apparatus of claim 1, wherein the processor is further configured to acquire second information by correcting the first information at a time point apart from the first time point toward the second time point by a first time period, acquire third information by correcting the first information at a time point apart from the second time point toward the first time point by the first time period, and generate corrected first information, based on the second information and the third information.

10. The tomography apparatus of claim 1, wherein the processor is further configured to warp a center of a voxel indicating the object based on the corrected first information, and reconstruct the final third image by back-projecting a position of the warped center of the voxel.

11. The tomography apparatus of claim 1, wherein the processor is further configured to select two time points at which a motion of the object is minimized within a predetermined time section, as the first time point and the second time point.

12. The tomography apparatus of claim 11, wherein the processor is further configured to reconstruct an image at intervals of a second time period within the predetermined time section, measure a difference between an image reconstructed at a fourth time point and an image reconstructed at a fifth time point which is adjacent to the fourth time point, and select two time points at which a motion of the object is minimized as the first time point and the second time point based on the measured difference.

13. The tomography apparatus of claim 11, wherein the processor is further configured to acquire projection data at intervals of a second time period within the predetermined time section, measure a difference between projection data reconstructed at a fourth time point and projection data reconstructed at a fifth time point which is adjacent to the fourth time point, and select two time points at which a motion of the object is minimized as the first time point and the second time point based on the measured difference.

14. The tomography apparatus of claim 1, further comprising a display configured to display a screen image including at least one from among the first image, the second image, the first information, the corrected first information, and the final third image.

15. The tomography apparatus of claim 14, wherein the display is further configured to display a user interface (UI) screen image for selecting the first time point, the second time point, and the third time point between the first and second time points.

16. The tomography apparatus of claim 1, wherein the processor is further configured to reconstruct a plurality of images respectively corresponding to a plurality of time points between the first time point and the second time point, by using the corrected first information.

17. The tomography apparatus of claim 16, further comprising a display configured to display a screen image including the plurality of images.

18. The tomography apparatus of claim 16, wherein the processor is further configured to generate a moving picture by using the plurality of images.

19. The tomography apparatus of claim 18, further comprising a display configured to display a user interface (UI) image for playing back the moving picture.

20. The tomography apparatus of claim 1, wherein the processor is further configured to perform motion correction with respect to the first image and the second image by using the corrected first information, and re-acquire the first information by using the motion-corrected first image and the motion-corrected second image.

21. A method for reconstructing a tomography image, the method comprising:
acquiring a first image corresponding to a first time point and a second image corresponding to a second time point by performing a tomography scan on an object;
acquiring first information representing to a relationship between a motion amount of the object and time based on a motion amount between the first image and the second image, predicting a third image corresponding to a third time point between the first time point and the second time point based on the first information, and correcting the first information by using the predicted third image and measured data corresponding to the third time point; and
reconstructing a final third image corresponding to the third time point by using the corrected first information.

22. The method of claim 21, wherein the first information is information indicating a relationship between a motion amount of the object corresponding to a motion vector field (MVF) between the first image and the second image and the time.

23. The method of claim 21, wherein the correcting the first information comprises correcting the first information, based on predicted data acquired by forward projecting the predicted third image and the measured data.

24. The method of claim 23, wherein the correcting the first information comprises comparing the predicted data with the measured data and correcting the first information so that a difference between the predicted data and the measured data decreases.

25. The method of claim 21, wherein the correcting the first information comprises:
comparing a predicted sinogram acquired by forward projecting the predicted third image with a measured sinogram acquired by detecting X-rays that have been projected by the object within a time section corresponding to the third time point; and
correcting the first information so that a difference between the predicted sinogram and the measured sinogram decreases.

26. The method of claim 21, wherein the correcting the first information comprises comparing a fourth image obtained by back-projecting measured data acquired at the third time point with the predicted third image and correcting the first information so that a difference between the predicted third image and the fourth image decreases.

27. The method of claim 21, wherein the correcting the first information comprises setting, as the third time point, a time point that is apart from the first time point toward the second time point by a first time period, and correcting the first information at the third time point.

28. The method of claim 21, wherein the correcting the first information comprises setting, as the third time point, a time point that is apart from the second time point toward the first time point by a first time period, and correcting the first information at the third time point.

29. The method of claim 21, wherein the correcting the first information comprises:
acquiring second information by correcting the first information at a time point apart from the first time point toward the second time point by a first time period;
acquiring third information by correcting the first information at a time point apart from the second time point toward the first time point by the first time period; and
generating corrected first information, based on the second information and the third information.

30. The method of claim 21, wherein the correcting the first information comprises warping a center of a voxel indicating the object based on the corrected first information and reconstructing the final third image by back-projecting a position of the warped center of the voxel.

31. The method of claim 21, wherein the acquiring the first image and the second image comprises:
selecting two time points at which a motion of the object is minimized within a predetermined time section as the first time point and the second time point; and
acquiring the first image and the second image at the selected first time point and the selected second time point, respectively.

32. The method of claim 21, further comprising displaying a user interface (UI) screen image for selecting the first time point and the second time point.

33. The method of claim 21, further comprising displaying a user interface (UI) screen image for selecting the third time point between the first time point and the second time point.

34. The method of claim 21, further comprising reconstructing a plurality of images respectively corresponding to a plurality of time points between the first time point and the second time point by using the corrected first information.

35. The method of claim 34, further comprising displaying a screen image including the plurality of images.

36. The method of claim 34, further comprising:
producing a moving picture by using the plurality of images; and
displaying a user interface (UI) screen image for playing back the moving picture.

37. The method of claim 21, further comprising performing motion correction on the first image and the second image by using the corrected first information and acquiring the first information by using the motion-corrected first image and the motion-corrected second image.

* * * * *